(12) United States Patent
Bhowmik et al.

(10) Patent No.: US 12,059,473 B2
(45) Date of Patent: Aug. 13, 2024

(54) HUMANIZED ANTI-PROSTATE -SPECIFIC MEMBRANE ANTIGEN (PSMA) ANTIBODY DRUG CONJUGATES

(71) Applicant: Ambrx, Inc., La Jolla, CA (US)

(72) Inventors: Shivarupam Bhowmik, La Jolla, CA (US); Jianing Wang, La Jolla, CA (US); Jinming Xia, La Jolla, CA (US); William Brady, La Jolla, CA (US); Feng Tian, La Jolla, CA (US)

(73) Assignee: Ambrx, Inc., La Jolla, CA (US)

( * ) Notice: Subject to any disclaimer, the term of this patent is extended or adjusted under 35 U.S.C. 154(b) by 339 days.

(21) Appl. No.: 17/042,838

(22) PCT Filed: Mar. 29, 2019

(86) PCT No.: PCT/US2019/025057
§ 371 (c)(1),
(2) Date: Sep. 28, 2020

(87) PCT Pub. No.: WO2019/191728
PCT Pub. Date: Oct. 3, 2019

(65) Prior Publication Data
US 2021/0015940 A1 Jan. 21, 2021

Related U.S. Application Data

(60) Provisional application No. 62/650,277, filed on Mar. 29, 2018.

(51) Int. Cl.
*A61K 47/68* (2017.01)
*A61K 45/06* (2006.01)
(Continued)

(52) U.S. Cl.
CPC .......... *A61K 47/6803* (2017.08); *A61P 35/00* (2018.01); *C07K 16/3069* (2013.01); *A61K 45/06* (2013.01)

(58) Field of Classification Search
None
See application file for complete search history.

(56) References Cited

U.S. PATENT DOCUMENTS

| 4,414,148 A | 11/1983 | Jansen et al. |
| 4,569,789 A | 2/1986 | Blattler et al. |

(Continued)

FOREIGN PATENT DOCUMENTS

| AU | 2015203742 B2 | 7/2015 |
| EP | 0188256 A2 | 7/1986 |

(Continued)

OTHER PUBLICATIONS

Axup et al. Synthesis of site-specific antibody-drug conjugates using unnatural amino acids. Proceedings of the National Academy of Sciences (40)109:16101-106 (2012) (Year: 2012).*

(Continued)

*Primary Examiner* — Scarlett Y Goon
*Assistant Examiner* — Audrey L Buttice

(57) ABSTRACT

The invention relates to prostate specific membrane antigen humanized antibodies (anti-PSMA) and anti-PSMA antibody drug conjugates. The invention also relates to methods and compositions for using anti-PSMA antibody drug conjugates in inhibiting, preventing or treating PSMA related diseases or cancers.

22 Claims, 8 Drawing Sheets

Specification includes a Sequence Listing.

(51) Int. Cl.
    *A61P 35/00*     (2006.01)
    *C07K 16/30*     (2006.01)

(56) References Cited

U.S. PATENT DOCUMENTS

| | | | |
|---|---|---|---|
| 4,659,839 | A | 4/1987 | Nicolotti et al. |
| 4,680,338 | A | 7/1987 | Sundoro |
| 4,699,784 | A | 10/1987 | Shih et al. |
| 7,807,619 | B2 | 10/2010 | Bertozzi et al. |
| 9,388,222 | B2 * | 7/2016 | Pastan ................ A61K 47/6851 |
| 10,800,856 | B2 | 10/2020 | Barnett et al. |
| 2003/0118592 | A1 | 6/2003 | Ledbetter et al. |
| 2003/0133939 | A1 | 7/2003 | Ledbetter et al. |
| 2015/0152190 | A1 * | 6/2015 | Barnett ................ A61P 35/00 530/300 |

FOREIGN PATENT DOCUMENTS

| | | |
|---|---|---|
| WO | WO1998/003873 A1 | 1/1998 |
| WO | 2005/074650 A2 | 8/2005 |
| WO | 2010/011735 A2 | 1/2010 |
| WO | 2012/166560 A1 | 12/2012 |
| WO | 2013/185117 A1 | 12/2013 |
| WO | WO2013/188740 A1 | 12/2013 |
| WO | WO2017/212250 A1 | 12/2017 |
| WO | 2018/033749 A1 | 2/2018 |

OTHER PUBLICATIONS

Liu, H et al., Monoclonal Antibodies to the Extracellular Domain of Prostate-Specific Membrane Antigen Also React with Tumor Vascular Endothelium:, Cancer Research, Proceedings: AACR 107th Annual Mtg., Apr. 16-20,; New Orleans, LA vol. 57, No. 17, Sep. 1, 1997, pp. 3629-3634, XP001080132, ISSN: 008-5472.
Maynard, J. & Georgiou, G., Annu. Rev. Biomed. Eng. 2:339-76, 2000.
Hu, S. et al., Cancer Research, 56, 3055-3061, 1996.
Bird, R.E. et al., Science 242:423-426, 1988.
Huston, J.S. et al., Proc. Natl. Acad. Sci. USA 85:5879-5883, 1988.
Riechmann, L. et al., Nature 332:323-327, 1988.
Jones, P.T. et al., Nature 321:522-525, 1986.
Queen, C. et al., Proc. Natl. Acad. USA 86:10029-10033, 1989.
Hudson, P.J., Curr. Opin. Biotechnol. 9:395-402, 1998.
Lobuglio, A. F. et al., Proc. Natl. Acad. Sci. (USA) 86:4220-4224, 1989.
Kettleborough, C. A. et al., Protein Engineering 4:773-783, 1991.
Co, M.S. et al., Proc. Natl. Acad. Sci. (USA) 88:2869-2873, 1991.
Carter, P. et al., Proc. Natl. Acad. Sci. (USA) 89:4285-4289, 1992.
Co, M.S. et al., J. Immunol. 148:1149-1154, 1992.
Batzer, M.A. et al., Nucleic Acid Res. 19:5081, 1991.
Ohtsuka, E. et al., J. Biol. Chem. 260:2605-2608, 1985.
Rossolini, G.M. et al., Mol. Cell. Probes 8:91-98, 1994.
Therasse, P. et al., J. Natl. Cancer Inst. 92(3):205-216, 2000.
Dubowchik, G.M. et al., Bioconjugate Chem. 13: 855-869, 2002.
Doronina, S.O. et al., Nature Biotechnology 21(7): 778-784, 2003.
Dipippo, V.A. et al., The Prostate 15;76(3):325-34, 2016.
Axup, J.Y. et al. 109 (40):16101-106, 2012.
Chin, J. et al., Science 301: 964-7, 2003.
Wang L., & Schultz, P. G., Chem. Comm., 1: 1-11, 2002.
Shao J. and Tam, J. P., J. Am. Chem. Soc. 117:3893-3899, 1995.
Chin J.W., et al., Proc. Natl. Acad. Sci. USA 99: 11020-11024, 2002.
Chin J.W. & Schultz P.G., ChemBioChem 3(11): 1135-1137, 2002.
Chin, J.W. et al., J. Amer. Chem. Soc. 124: 9026-9027, 2002.
Hang H. and Bertozzi C., Acc. Chem. Res. 34(9): 727-736, 2001.
Dipippo, V.A. et al., "Addition of PSMA ADC to Enzalutamide Therapy Significantly Improves Survival in In Vivo Model of Castration Resistant Prostate Cancer", The Prostate, pp. 325-334 (2016).
Tian, F., et al., Proc. Natl. Acad. Sci., vol. 111, No. 5, pp. 1766-1771 (2014).
Sapra, P.S. et al., Cancer Res. Vol. 72, No. 8_Supplement, p. 5691, Abstract 5691 (2012).
Ke X. et al., Journal Contemporary Urologic and Reproductive Oncology 253-256 (2017).
Shishi X. et al. Chinese Journal of Cellular and Monoclonal Immunology, 278-282 (2017).
Li Y. et al., Prostate Cancer and Prostatic Diseases 5:36-46 (2002).

* cited by examiner

HUMANIZED ANTI-PROSTATE-SPECIFIC MEMBRANE ANTIGEN (PSMA) ANTIBODY DRUG CONJUGATES

CROSS-REFERENCE TO RELATED APPLICATIONS

This application is a U.S. National Stage entry under 35 U.S.C § 371 of International Application No. PCT/US2019/025057, filed on Mar. 29, 2019, which is incorporated by reference herein in its entirety and claims priority to and the benefit of U.S. Provisional Application Ser. No. 62/650,277 filed on Mar. 29, 2018, the specification and contents of which is incorporated by reference herein in its entirety for all purposes.

SEQUENCE LISTING

The instant application contains a Sequence Listing which has been submitted in ASCII format via EFS-Web and is hereby incorporated by reference in its entirety. The ASCH copy, was created on Mar. 29, 2019 is named AMBX_0225_00PCT_ST25.txt and is 37,015 bytes in size.

FIELD OF THE INVENTION

The invention disclosure relates to novel prostate-specific membrane antigen (anti-PSMA) antibodies and antibody drug conjugates. More particularly, the invention disclosure relates to methods and compositions for using anti-PSMA antibody drug conjugates in inhibiting, preventing or treating PSMA related diseases or cancers.

BACKGROUND OF THE INVENTION

Prostate cancer is the most commonly diagnosed non-skin related malignancy in males in developed countries. It is estimated that one in six males will be diagnosed with prostate cancer. The diagnosis of prostate cancer has improved following the use of serum-based markers such as the prostate-specific antigen (PSA). In addition, prostate tumor-associated antigens offer targets for tumor imaging, diagnosis, and targeted therapies. Prostate specific membrane antigen (PSMA), a prostate tumor associated marker, is such a target. PSMA is significantly overexpressed in androgen independent prostate cancer. Overexpression of PSMA is associated with high tumor grade, a high risk of disease progression and recurrence (Perner et al, Human Pathology, 2007). High expression of PSMA has been associated with negative clinical prognosis and significantly shorter survival. PSMA expression is observed both in primary disease site and in metastatic sites such as, bone and lymph nodes (Olson and Israel, Frontiers in Bioscience, 2014).

Although several targeted therapies have been pursued over the years, those involving radiotherapies have advanced the most towards clinical development as they demonstrated both efficacy and acceptable tolerability. Other clinical development of modalities involving targeted delivery of non-radioactive cytotoxic agents have met with limited success.

Given the physical properties of PSMA and its expression pattern in relation to prostate cancer progression PSMA is an excellent target in the development of antibody-drug conjugates. Antibody-drug conjugates (ADCs) are a potent class of therapeutic constructs that allow targeted delivery of cytotoxic agents to target cells, such as cancer cells. Because of the targeting function, these compounds show a much higher therapeutic index compared to the same systemically delivered agents. ADCs have been developed as intact antibodies or antibody fragments, such as scFvs. The antibody or fragment is linked to one or more copies of drug via a linker that is stable under physiological conditions, but that may be cleaved once inside the target cell. To date only, only a couple of ADCs have been approved for therapeutic use including gemtuzumab ozogamicin for AML (subsequently withdrawn from the market), brentuximab vedotin for ALCL and Hodgkin lymphoma, and trastuzumab emtansine for HER2-positive metastatic breast cancer (Verma et al., N Eng J Med 367:1783-91, 2012; Bross et al., Clin Cancer Res 7:1490-96, 2001; Francisco et al., Blood 102:1458-65, 2003). A number of ADCs targeting various agents are in clinical trials. However, ADCs targeting PSMA face challenges due to lack of therapeutic index and toxicity.

Thus, a need exists for better or improved therapeutics targeting PSMA antigen and related cancers. To overcome this deficiency in the art, the present invention disclosure provides novel anti-PSMA antibodies, variants, and antibody drug conjugates compositions, herein.

SUMMARY OF THE INVENTION

The present invention disclosure provides anti-PSMA antibodies, antibody variants, and antibody drug conjugate compositions. In further embodiments the invention disclosure provides antibody drug conjugates (ADCs) comprising such anti-PSMA antibodies.

The present invention disclosure provides anti-PSMA antibodies, antibody variants, and antibody composition comprising SEQ ID NOs: 1 to 17. In some embodiments the invention disclosure provides antibody drug conjugates (ADCs) comprising SEQ ID NOs: 1 to 17.

The present invention disclosure provides anti-PSMA antibodies, antibody variants, and antibody composition consisting of SEQ ID NOs: 1 to 17. In some embodiments the invention disclosure provides antibody drug conjugates (ADCs) consisting of SEQ ID NOs: 1 to 17.

The present invention provides an anti-prostate specific membrane antigen antibody (anti-PSMA) variant comprising a heavy chain and a light chain wherein the heavy chain sequence is selected from the group of SEQ ID NOs: 8, 10, 12, 14, or 16 and the light chain sequence is selected from the group of SEQ ID NOs: 9, 11, 13, 15, or 17. In some embodiments, the present invention provides an anti-prostate specific membrane antigen antibody (anti-PSMA) variant comprising a heavy chain sequence of SEQ ID NOs: 8, 10, 12, 14, or 16. In some embodiments, the present invention provides an anti-prostate specific membrane antigen antibody (anti-PSMA) variant comprising of a light chain sequence of SEQ ID NOs: 9, 11, 13, 15, or 17.

In other embodiments, the present invention provides an anti-prostate specific membrane antigen antibody (anti-PSMA) variant consisting of a heavy chain sequence of SEQ ID NOs: 8, 10, 12, 14, or 16. In other embodiments, the present invention provides an anti-prostate specific membrane antigen antibody (anti-PSMA) variant consisting of a light chain sequence of SEQ ID NOs: 9, 11, 13, 15, or 17.

In another embodiment, the anti-PSMA antibody variant comprises a heavy chain comprising a variable sequence region selected from the group of SEQ ID NOs: 1 or 6. In still another embodiment, the anti-PSMA antibody variant comprises a light chain sequence comprising a variable region selected from the group of SEQ ID NOs: 2-5 or 7. In yet another embodiment, the anti-PSMA antibody heavy chain variant consists of a variable region sequence of SEQ ID NOs: 1 or 6. In still another embodiment, the anti-PSMA antibody light chain variant consist of a variable region selected from the group of SEQ ID NOs: 2-5 or 7.

In a further embodiment, the anti-PSMA antibody variant comprises a non-natural amino acid incorporated in the heavy or light chain sequence of the antibody. In another embodiment of the present invention, the antibody comprises an anti-PSMA antibody variant with one or more non-naturally encoded amino acids substituted at one or more positions in the antibody heavy chain or light chain. In some embodiments the heavy chain or light chain in the PSMA antibody variant comprises, 1, 2, 3, 4, 5, 6, 7, 8, 9, or 10 non-naturally encoded amino acids. In other embodiments the heavy chain or light chain sequence in the PSMA antibody variant comprises, 1, 2, 3, 4, 5, 6, 7, 8, 9, or 10 non-naturally encoded amino acids at one or more positions in the antibody heavy chain or light chain. In one embodiment, the anti-PSMA antibody heavy chain sequence comprises a non-naturally encoded amino acid. In another embodiment of the present invention, the anti-PSMA antibody variant comprises a heavy or a light chain sequence as presented in Table 4.

In further embodiments of the present invention, the antibody is an anti-PSMA antibody variant comprising the light chain sequence from SEQ ID NOs: 9, 11, 13, 15, or 17 with a non-naturally encoded amino acid substituted at a position with high surface accessibility and/or a site that will be charge neutral to the antibody. In still further embodiments of the present invention, the antibody is an anti-PSMA antibody variant comprising the heavy chain sequence from SEQ ID NOs: 8, 10, 12, 14, or 16 with a non-naturally encoded amino acid substituted at a position with high surface accessibility and/or a site that will be charge neutral to the antibody.

In one embodiment, the present invention provides an anti-PSMA antibody drug conjugate (ADC or an anti-PSMA ADC) wherein the antibody is an anti-PSMA comprising a light and heavy chain sequence. In further embodiments of the present invention, the anti-PSMA ADC comprises the light chain from SEQ ID NOs: 9, 11, 13, 15, or 17 and the heavy chain from SEQ ID NOs: 8, 10, 12, 14, or 16. In one embodiment of the present invention, the anti-PSMA ADC comprises with one or more non-naturally encoded amino acids substituted at one or more positions in the antibody heavy chain or light chain.

In another embodiment the present invention provides an anti-PSMA ADC comprising a heavy chain SEQ. ID. NO: 8 and a light of SEQ. ID. NO: 9. In another embodiment, the present invention provides an anti-PSMA ADC comprising SEQ ID NO: 12 and SEQ ID NO: 13. In another embodiment, the present invention provides an anti-PSMA ADC comprising SEQ ID NO: 14 and SEQ ID NO: 15. In another embodiment, the present invention provides an anti-PSMA ADC comprising SEQ ID NO: 16 and SEQ ID NO: 17.

In some embodiments, the antibody, variant, or composition of the present disclosure may be an antibody, variant, or composition that binds to a PSMA receptor. In other embodiments of the present invention the antibody, variant, or composition may be an antibody, variant, or composition that binds to extracellular surface of PSMA receptor. In another embodiment of the present invention the antibody, variant, or composition disclosed may be an antibody, variant, or composition that bind to a PSMA dimer. In some embodiments the antibody, variant, or composition of the present disclosure may be an antibody, variant, or composition that has CDRs from J591 grafted onto the framework region of the variable region. In other embodiments the antibody, variant, or composition of the present invention disclosure may be an antibody, variant, or composition that has a non-naturally encoded amino acid. In some embodiments the antibody, variant, or composition may be an antibody, variant, or composition that is described by more than one of the embodiments elsewhere herein the present invention disclosure. In some embodiments the antibody, antibody variant or antibody composition(s) disclosed herein may be fully humanized. In other embodiments the antibody, antibody variant or antibody composition(s) disclosed herein may be chimeric. In some embodiments of the present invention the antibody may be an antibody that is full length antibody (Variable+Fc regions), Fab, bispecific, Fab-dimers, Fab-bispecific, Fab-trispecific, bispecific T-cell engagers, dual-affinity re-targeting antibody, IgG1/IgG3 bispecific antibody, diabody, bispecific diabody, scFv-Fc, minibody.

In other embodiments, the anti-PSMA antibody, antibody variant, or antibody composition incorporates a non-natural encoded amino acid comprising a carbonyl group, an aminooxy group, a hydrazine group, a hydrazide group, a semicarbazide group, an azide group, or an alkyne group. In one embodiment of the invention, the non-natural encoded amino acid comprises an aminooxy group. In still other embodiments, the non-naturally encoded amino acid is para-acetyl phenylalanine, p-nitrophenylalanine, p-sulfotyrosine, p-carboxyphenylalanine, an o-nitrophenylalanine, an m-nitrophenylalanine, a p-boronyl phenylalanine, an o-boronylphenylalanine, an m-boronylphenylalanine, a p-aminophenylalanine, an o-aminophenylalanine, an m-aminophenylalanine, a p-acylphenylalanine, an o-acylphenylalanine, an m-acylphenylalanine, a p-OMe phenylalanine, an o-OMe phenylalanine, an m-OMe phenylalanine, a p-sulfophenylalanine, an o-sulfophenylalanine, an m-sulfophenylalanine, a 5-nitro His, a 3-nitro Tyr, a 2-nitro Tyr, a nitro substituted Leu, a nitro substituted His, a nitro substituted De, a nitro substituted Trp, a 2-nitro Trp, a 4-nitro Trp, a 5-nitro Trp, a 6-nitro Trp, a 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenylalanine, p-acetyl-L-phenylalanine, a p-propargyl-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine or a p-propargyloxy-phenylalanine. In another embodiment of the present invention the non-natural amino acid is para-acetyl phenylalanine.

In other embodiments of the present invention the anti-PSMA antibody variant is a monoclonal antibody, humanized antibody, or chimeric antibody. In one embodiment the anti-PSMA humanized antibody variant comprises a heavy chain sequence selected from the group of SEQ ID NOs: 8, 10, 12, or 14 and a light chain sequence selected from the group of SEQ ID NOs: 9, 11, 13, or 15. In another embodiment the anti-PSMA chimeric antibody variant comprises a heavy chain sequence of SEQ ID NO: 16 and a light chain sequence of SEQ ID NO: 17.

In other embodiments the present invention provides a composition of an antibody drug conjugate comprising an anti-PSMA antibody variant covalently conjugated to a toxin, payload or drug-linker. In one embodiment the toxin, payload or drug-linker comprises a cytotoxic agent. In one embodiment the cytotoxic agent is a dolastatin, dolastatin derivative or analog thereof. In other embodiments the present invention provides a composition of an antibody drug conjugate comprising an anti-PSMA antibody variant covalently conjugated to a drug-linker wherein the conjugation occurs via a non-naturally encoded amino acid in the antibody. In other embodiments the present invention provides a composition of an antibody drug conjugate comprising an anti-PSMA antibody variant of any of SEQ ID NOs: 1 to 17 covalently conjugated to one or more dolastatin wherein the conjugation occurs via a non-naturally encoded amino acid in the antibody. In another embodiment of the present invention is provided a composition of an antibody drug conjugate comprising an anti-PSMA antibody variant of any of SEQ ID NOs: 8 to 17 covalently conjugated to one or more dolastatin wherein the conjugation occurs via a non-naturally encoded amino acid in the antibody. In one embodiment of the present invention is provided a composition of an antibody drug conjugate comprising an anti-PSMA antibody heavy chain sequence variant of SEQ ID NOs: 8, 10, 12, 14, or 16 covalently conjugated to one or more dolastatin wherein the conjugation occurs via a non-naturally encoded amino acid in the antibody. In one other embodiment of the present invention is provided a composition of an antibody drug conjugate comprising an anti-PSMA antibody light chain variant of SEQ ID NOs: 9, 11, 13, 15, or 17 covalently conjugated to one or more dolastatin wherein the conjugation occurs via a non-naturally encoded amino acid in the antibody. In another embodiment the antibody is covalently conjugated to at least 2 dolastatins. In one embodiment, the composition comprises 1, 2, 3, 4, 5, 6, 7, 8, 9, 10 or more dolastatin derivative or analog. In one embodiment, the composition comprises a dolastatin derivative or is a dolastatin analog. In another embodiment, the dolastatin derivative or analog is a monomethyl auristatin, the monomethyl auristatin is monomethyl auristatin F (MMAF) or monomethyl auristatin E (MMAE). In other embodiments, the one or more dolastatin is non-cleavable MMAF, non-cleavable MMAE, cleavable MMAF, cleavable MMAE, short cleavable MMAF, or short cleavable MMAE. In a further embodiment of the invention, the antibody is linked to a linker, a polymer or biologically active molecule. In some embodiments the linker is poly ethylene glycol (PEG). In other embodiments the linker is a branched or linear poly ethylene glycol. In further embodiments of the present invention the anti-PSMA variants can be PEGylated. In still further embodiments of the present invention the anti-PSMA variants can be PEGylated on the non-naturally encoded amino acid. The anti-PSMA antibody of the present invention can be PEGylated with about 5 kDa PEG, about 10 kDa PEG, about 20 kDa PEG, about 30 kDa PEG, about 40 kDa PEG or greater. The poly(ethylene glycol) molecule can have a molecular weight of between about 0.1 kDa and about 100 kDa. The poly(ethylene glycol) molecule can have a molecular weight of between 0.1 kDa and 50 kDa, 20 kDa and 40 kDa, and any integer value between 25 kDa and 35 kDa. The poly(ethylene glycol) molecule can have a molecular weight of about 30 kDa. The poly(ethylene glycol) molecule can be a linear molecule having a molecular weight of between 0.1 kDa and 50 kDa, 20 kDa and 40 kDa, and any integer value between 25 kDa and 35 kDa. The poly(ethylene glycol) molecule can be a linear molecule having a molecular weight of 30 kDa. The poly(ethylene glycol) molecule can have an aminooxy group capable of reacting with an acetyl group on a synthetic amino acid. The poly(ethylene glycol) molecule can be a 30 kDa aminooxy activated linear PEG capable of forming an oxime bond with the acetyl side chain of a non-naturally encoded amino acid such as, but not limited to, para-acetyl phenylalanine.

In one embodiment the present invention provides antibody drug conjugate comprising a humanized anti-PSMA antibody comprising a heavy chain sequence selected from SEQ ID NO: 8, 10, 12, 14, or 16 and a light chain sequence selected from SEQ ID NO: 9, 11, 13, 15, conjugated to at least one drug-linker selected from Tables 1-3, wherein the conjugation occurs via a non-naturally encoded amino acid incorporated in the heavy chain sequence. In some embodiments, the drug-linker comprises is a cytotoxic agent. The cytotoxic agent is a dolastatin, dolastatin derivative or analog thereof. In one embodiment the dolastatin, dolastatin derivative or analog is a monomethyl auristatin selected from monomethyl auristatin F (MMAF) or monomethyl auristatin E (MMAE). In another embodiment, the monomethyl auristatin is cleavable MMAE or MMAF, non-cleavable NMAE or MMAF, short cleavable MMAE or MMAF.

In one embodiment the present invention provides a method for reducing or inhibiting tumor growth or progression in a PSMA-expressing cancer or cancer cell comprising contacting the PSMA-expressing cancer or cancer cell with an effective amount of the antibody-drug conjugate. The antibody drug conjugate comprising a humanized anti-PSMA antibody comprising a heavy chain sequence selected from SEQ ID NO: 8, 10, 12, 14, or 16 and a light chain sequence selected from SEQ ID NO: 9, 11, 13, 15, conjugated to at least one drug-linker selected from Tables 1-3, wherein the conjugation occurs via a non-naturally encoded amino acid incorporated in the heavy chain sequence. In another embodiment the invention provides a method further comprising contacting a PSMA-expressing cancer or cancer cell with an effective amount of a therapeutic agent. In another embodiment, the therapeutic agent is a chemotherapeutic agent, hormonal agent, antitumor agent, immunostimulatory agent, immunomodulator, corticosteroid or combination thereof. In one embodiment, the hormonal agent is enzalutamide.

In other embodiments the anti-PSMA ADCs of the invention can be administered with one or more immunostimulatory agents to induce or enhance an immune response. Such immunostimulatory agents include, but are not limited to, IL-2, immunostimulatory oligonucleotides (for example, CpG motifs), interferons, tumor necrosis factor alpha. In other embodiments the anti-PSMA ADCs of the invention can be administered with one or more immunomodulators including, but not limited to, cytokines, chemokines, adjuvants or a combination thereof.

In further embodiments the present invention provides a method of inhibiting tumor growth or progression in a subject comprising providing to the subject a therapeutically effective amount of an PSMA antibody drug conjugate of the invention. In still a further embodiment, the present invention provides a method of treating a subject having prostate cancer comprising providing to the subject a therapeutically effective amount of a composition of the disclosure.

In one embodiment the present invention provides a method of treating a subject having a PSMA-expressing cancer cell or cancer comprising: administering to the subject an effective amount of an antibody-drug conjugate to treat the PSMA-expressing cancer or cancer cell, wherein the antibody-drug conjugate comprises a PSMA antibody comprising a heavy chain and light chain sequence of disclosed herein conjugated to drug-linker via a non-naturally encoded amino acid incorporated in the antibody; and wherein the drug-linker is selected from Tables 1-3. In another embodiment, a method of treating a subject having PSMA related disease or cancer comprising providing to the subject a therapeutically effective amount of anti-PSMA antibody drug conjugate and a therapeutic agent. The therapeutic agent is a chemotherapeutic agent, hormonal agent, antitumor agent, immunostimulatory agent, immunomodulator, corticosteroid or combination thereof. The therapeutic agent can be provided prior to, after, or in conjunction with an anti-PSMA ADC of the invention.

In another embodiment, the invention disclosure provides a pharmaceutical composition comprising an anti-PSMA antibody variant and at least one pharmaceutically acceptable adjuvant, binder, buffer, carrier, diluent or excipient. A pharmaceutical composition comprising the antibody drug conjugate of the invention and at least one pharmaceutically acceptable adjuvant, binder, buffer, carrier, diluent or excipient. The pharmaceutical composition further comprising a therapeutic agent. In one embodiment that invention provides u a medicament for manufacture and for treating cancer in a subject in need thereof.

In a further embodiment the present invention provides a nucleic acid encoding any of SEQ ID NOs: 1-17. In one embodiment, the invention provides a vector comprising the nucleic acid of SEQ ID NOs: 1-17.

It is to be understood that the methods and compositions described herein are not limited to the particular methodology, protocols, cell lines, constructs, and reagents described herein and as such may vary. It is also to be understood that the terminology used herein is for the purpose of describing particular embodiments only and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Various methods, materials, and the like, similar or equivalent to those described herein can be used in the practice or testing of the inventions described herein.

All publications and patents mentioned herein are incorporated herein by reference in their entirety for the purpose of describing and disclosing, for example, the chemistry, chemical syntheses, compositions and other methodologies that are described in the publications, which might be used in connection with the presently described inventions. The publications discussed herein are provided solely for their disclosure prior to the filing date of the present application.

In embodiments of the present disclosure are provided novel anti-PSMA amino acid sequences. The term "amino acid" refers to naturally occurring and non-natural or unnatural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to compounds that have the same basic chemical structure as a naturally occurring amino acid, by way of example only, an a-carbon that is bound to a hydrogen, a carboxyl group, an amino group, and a functional R group. Such analogs may have modified R groups (by way of example, norleucine) or may have modified peptide backbones while still retaining the same basic chemical structure as a naturally occurring amino acid. Non-limiting examples of amino acid analogs include homoserine, norleucine, methionine sulfoxide, methionine methyl sulfonium. Amino acids may be referred to herein by either their name, their commonly known three letter symbols or by the one-letter symbols recommended by the IUPAC-IUB Biochemical Nomenclature Commission. Additionally, nucleotides, may be referred to by their commonly accepted single-letter codes.

An "amino or carboxy terminus modification group" refers to any molecule that can be attached to a terminal amine group or terminal carboxy group respectively. By way of example, such terminal amine groups or terminal carboxy groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides, polypeptides or proteins.

In some embodiments the invention disclosure provides novel anti-PSMA antibodies and antibody variants. The term "antibody" herein refers to a protein consisting of one or more polypeptides substantially encoded by all or part of the antibody genes. The immunoglobulin genes include, but ar not limited to, the kappa, lambda, alpha, gamma (IgG1, IgG2, IgG3, and IgG4), delta, epsilon and mu constant region genes, as well as the myriad immunoglobulin variable region genes. Antibody herein is also meant to include full-length antibodies and antibody fragments, and include antibodies that exist naturally in any organism, antibody variants, engineered antibodies and antibody fragments. Antibody herein is also meant to include intact antibody, monoclonal or polyclonal antibodies. Antibody herein also encompasses, multispecific antibodies and/or bispecific antibodies. Antibodies of the present invention include human antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antibody fragment" herein refers to any form of an antibody other than the full-length form. Antibody fragments herein include antibodies that are smaller components that exist within full-length antibodies, and antibodies that have been engineered, such as antibody variants. Antibody fragments include but are not limited to Fv, Fc, Fab, and (Fab')$_2$, single chain Fv (scFv), diabodies, triabodies, tetrabodies, bifunctional hybrid antibodies, CDR1, CDR2, CDR3, combinations of CDRs, variable regions, framework regions, constant regions, heavy chains, light chains, and variable regions, and alternative scaffold non-antibody molecules, bispecific antibodies, and the like (Maynard & Georgiou, Annu. Rev. Biomed. Eng. 2:339-76, 2000; Hudson, Curr. Opin. Biotechnol. 9:395-402, 1998). Another functional substructure is a single chain Fv (scFv), comprised of the variable regions of the immunoglobulin heavy and light chain, covalently connected by a peptide linker (Hu et al., Cancer Research, 56, 3055-3061, 1996). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments."

In embodiments of the present invention novel anti-PSMA antibody drug conjugates (ADCs) are disclosed. The term "antibody-drug conjugate, or "ADC", as used herein, refers to an antibody molecule, or fragment thereof, that is covalently bonded to one or more biologically active molecule(s). The biologically active molecule may be conjugated to the antibody through a linker, polymer, or other covalent bond. ADCs are a potent class of therapeutic constructs that allow targeted delivery of cytotoxic agents to target cells, such as cancer cells. Because of the targeting function, these compounds show a much higher therapeutic index compared to the same systemically delivered agents. ADCs have been developed as intact antibodies or antibody fragments, such as scFvs. The antibody or fragment is linked to one or more copies of drug via a linker that is stable under physiological conditions, but that may be cleaved once inside the target cell.

The term "antigen-binding fragment", as used herein, refers to one or more fragments of an antibody that retain the ability to bind to an antigen. It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546, 1989), which consists of a $V_H$ domain; (vi) an isolated complementarity determining region (CDR), e.g., $V_H$ CDR3 comprising or not additional sequence (linker, framework region(s) etc.) and (v) a combination of two to six isolated CDRs comprising or not additional sequence (linker, framework region(s) etc.). Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al., Science 242:423-426, 1988); and (Huston et al., Proc. Natl. Acad. Sci. USA 85:5879-5883, 1988). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding. In fact, because CDR sequences are responsible for most antibody-antigen interactions, it is possible to express recombinant antibodies that shows the properties of specific naturally occurring antibodies by constructing expression vectors that include CDR sequences from the specific naturally occurring antibody grafted onto framework sequences from a different antibody with different properties (see, e.g., Riechmann, L. et al., Nature 332:323-327, 1998; Jones, P. et al., Nature 321:522-525, 1986; and Queen, C. et al., Proc. Natl. Acad. USA 86:10029-10033, 1989). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized to create an entirely synthetic variable region clone. This process has certain advantages such as elimination or inclusion of particular restriction sites, or optimization of particular codons. Of course, the totality or portions of the framework region of the antibody described herein may be used in conjunction with the CDRs in order to optimize the affinity, specificity or any other desired properties of the antibody.

In some embodiments the invention concerns polymers such as a bifunctional polymer. A "bifunctional polymer", also referred to as a "bifunctional linker", refers to a polymer comprising two functional groups that are capable of reacting specifically with other moieties to form covalent or non-covalent linkages. Such moieties may include, but are not limited to, the side groups on natural or non-natural amino acids or peptides which contain such natural or non-natural amino acids. The other moieties that may be linked to the bifunctional linker or bifunctional polymer may be the same or different moieties. By way of example only, a bifunctional linker may have a functional group reactive with a group on a first peptide, and another functional group which is reactive with a group on a second peptide, whereby forming a conjugate that includes the first peptide, the bifunctional linker and the second peptide. Many procedures and linker molecules for attachment of various compounds to peptides are known. See, for example, European Patent Application No. 0188256; U.S. Pat. Nos. 4,659,839; 4,414, 148; 4,699,784; 4,680,338; and 4,569,789 incorporated herein by reference in their entirety. A "multi-functional polymer" also referred to as a "multi-functional linker", refers to a polymer comprising two or more functional groups that are capable of reacting with other moieties. Such moieties may include, but are not limited to, the side groups on natural or non-natural amino acids or peptides which contain such natural or non-natural amino acids. (including but not limited to, amino acid side groups) to form covalent or non-covalent linkages. A bi-functional polymer or multi-functional polymer may be any desired length or molecular weight and may be selected to provide a particular desired spacing or conformation between one or more molecules linked to a compound and molecules it binds to, or to the compound.

The term "bioavailability," as used herein, refers to the rate and extent to which a substance or its active moiety is delivered from a pharmaceutical dosage form and becomes available at the site of action or in the general circulation. Increases in bioavailability refers to increasing the rate and extent a substance or its active moiety is delivered from a pharmaceutical dosage form and becomes available at the site of action or in the general circulation. By way of example, an increase in bioavailability may be indicated as an increase in concentration of the substance or its active moiety in the blood when compared to other substances or active moieties.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, prodrugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal and nonsteroidal agents, microbially derived toxins, and the like.

By "modulating biological activity" is meant increasing or decreasing the reactivity of a polypeptide, altering the selectivity of the polypeptide, enhancing or decreasing the substrate selectivity of the polypeptide. Analysis of modified biological activity can be performed by comparing the biological activity of the non-natural polypeptide to that of the natural polypeptide.

In some embodiments the disclosure concerns amino acids that have been biosynthetically incorporated in the antibody. The term "biosynthetically," as used herein, refers to any method utilizing a translation system (cellular or non-cellular), including use of at least one of the following components: a polynucleotide, a codon, a tRNA, and a ribosome. By way of example, non-natural amino acids may be "biosynthetically incorporated" into non-natural amino acid polypeptides using the methods and techniques described herein and as is well known in the art. See for example, WO2010/011735 and WO2005/074650.

The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons OCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus, by way of example every natural or non-natural nucleic acid sequence herein which encodes a natural or non-natural polypeptide also describes every possible silent variation of the natural or non-natural nucleic acid. One of ordinary skill in the art will recognize that each codon in a natural or non-natural nucleic acid (except AUG, which is ordinarily the only codon for methionine, and TGG, which is ordinarily the only codon for tryptophan) can be modified to yield a-functionally identical molecule. Accordingly, each silent variation of a natural and non-natural nucleic acid which encodes a natural and non-natural polypeptide is implicit in each described sequence. As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence is a "conservatively modified variant" where the alteration results in the deletion of an amino acid, addition of an amino acid, or substitution of a natural and non-natural amino acid with a chemically similar amino acid. Conservative substitution tables providing functionally similar natural amino acids are well known in the art. Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M); Valine (V); 6) Phenylalanine (F), Tyrosine (Y), Tryptophan (W); 7) Serine (S), Threonine T); and 8) Cysteine (C), Methionine (M) (see, e.g., Creighton, Proteins: Structures and Molecular Properties (W H Freeman & Co.; 2nd edition, 1993). Such conservatively modified variants are in addition to and do not exclude polymorphic variants, interspecies homologs, and alleles of the compositions described herein.

The term "drug," as used herein, refers to any substance used in the prevention, diagnosis, alleviation, treatment, or cure of a disease or condition such as cancer, including prostate cancer.

The term "effective amount," as used herein, refers to a sufficient amount of an agent, compound or composition being administered which will relieve to some extent one or more of the symptoms of the disease or condition being treated. The result can be reduction and/or alleviation of the signs, symptoms, or causes of a disease, or any other desired alteration of a biological system. By way of example, an agent, compound or composition being administered includes, but is not limited to, a natural amino acid polypeptide, non-natural amino acid polypeptide, modified natural amino acid polypeptide, modified non-amino acid polypeptide, or an antibody or variant thereof. Compositions containing such natural amino acid polypeptides, non-natural amino acid polypeptides, modified natural amino acid polypeptides, modified non-natural amino acid polypeptides, or an antibody or variant thereof can be administered for prophylactic, enhancing, and/or therapeutic treatments. An appropriate "effective" amount in any individual case may be determined using techniques, such as a dose escalation study.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "humanized or chimeric antibody" refer to a molecule, generally prepared using recombinant techniques, having an antigen binding site derived from an immunoglobulin from a non-human species, (e.g., murine), and the remaining immunoglobulin structure of the molecule based upon the structure and/or sequence of a human immunoglobulin. In general, the humanized antibody will comprise substantially all of at least one, and typically two, variable domains, in which all or substantially all of the hypervariable loops correspond to those of a non-human immunoglobulin and all or substantially all of the framework residues/regions (FR) are those of a human immunoglobulin sequence. The humanized antibody optionally also will comprise at least a portion of an immunoglobulin constant region (Fc), typically that of a human immunoglobulin. The humanized forms of rodent antibodies will essentially comprise the same CDR sequences of the parental rodent antibodies, although certain amino acid substitutions may be included to increase affinity, increase stability of the humanized antibody, or for other reasons. However, as CDR loop exchanges do not uniformly result in an antibody with the same binding properties as the antibody of origin, changes in framework residues (FR), residues involved in CDR loop support, might also be introduced in humanized antibodies to preserve antigen binding affinity. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions. This eliminates the constant region as an immunogen in human individuals, but the possibility of an immune response to the foreign variable region remains (LoBuglio, A. F. et al., "Mouse/Human Chimeric Monoclonal Antibody In Man: Kinetics And Immune Response," Proc. Natl. Acad. Sci. (USA) 86:4220-4224, 1989). Another approach focuses not only on providing human-derived constant regions but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "humanized" by grafting CDRs derived from nonhuman antibody on the FRs present in the human antibody to be modified. Application of this approach to various antibodies has been reported by Kettleborough, C. A. et al., "Humanization Of A Mouse Monoclonal Antibody By CDR-Grafting: The Importance Of Framework Residues On Loop Conformation," Protein Engineering 4:773-3783, 1991; Co, M. S. et al., "Humanized Antibodies For Antiviral Therapy," Proc. Nati. Acad. Sci. (USA) 88:2869-2873, 1991; Carter, P. et al., "Humanization Of An Anti-p185her2 Antibody For Human Cancer Therapy," Proc. Natl. Acad. Sci. (USA) 89:4285-4289, 1992; and Co, M. S. et al., "Chimeric And Humanized Antibodies With Specificity For The CD33 Antigen," J. Immunol. 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

The term "identical," as used herein, refers to two or more sequences or subsequences which are the same. In addition, the term"substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75 to about 100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75 to about 100 nucleic acids in length, over a region that is about 50 nucleic acids in length, or, where not specified, across the entire sequence of a polynucleotide sequence.

The term "immunogenicity," as used herein, refers to an antibody response to administration of a therapeutic drug. The immunogenicity toward therapeutic non-natural amino acid polypeptides can be obtained using quantitative and qualitative assays for detection of anti-non-natural amino acid polypeptides antibodies in biological fluids. Such assays include, but are not limited to, Radioimmunoassay (RIA), Enzyme-linked immunosorbent assay (ELISA), luminescent immunoassay (LIA), and fluorescent immunoassay (FIA). Analysis of immunogenicity toward therapeutic non-natural amino acid polypeptides involves comparing the antibody response upon administration of therapeutic non-natural amino acid polypeptides to the antibody response upon administration of therapeutic natural amino acid polypeptides.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high-performance liquid chromatography. In addition, when a component of interest is isolated and is the predominant species present in a preparation, the component is described herein as substantially purified. The term"purified," as used herein, may refer to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "linkage," as used herein to refer to bonds or chemical moiety formed from a chemical reaction between the functional group of a linker and another molecule. Such bonds may include, but are not limited to, covalent linkages and non-covalent bonds, while such chemical moieties may include, but are not limited to, esters, carbonates, imines phosphate esters, hydrazones, acetals, orthoesters, peptide linkages, and oligonucleotide linkages. Hydrolytically stable linkages mean that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. By way of example only, PEG and related polymers may include degradable linkages in the polymer backbone or in the linker group between the polymer backbone and one or more of the terminal functional groups of the polymer molecule. Such degradable linkages include but are not limited to ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "metabolite," as used herein, refers to a derivative of a compound, by way of example natural amino acid polypeptide, a non-natural amino acid polypeptide, a modified natural amino acid polypeptide, or a modified non-natural amino acid polypeptide, that is formed when the compound, by way of example natural amino acid polypeptide, non-natural amino acid polypeptide, modified natural amino acid polypeptide, or modified non-natural amino acid polypeptide, is metabolized. The term "pharmaceutically active metabolite" or "active metabolite" refers to a biologically active derivative of a compound, by way of example natural amino acid polypeptide, a non-natural amino acid polypeptide, a modified natural amino acid polypeptide, or a modified non-natural amino acid polypeptide, that is formed when such a compound, by way of example a natural amino acid polypeptide, non-natural amino acid polypeptide, modified natural amino acid polypeptide, or modified non-natural amino acid polypeptide, is metabolized.

The term "metabolized," as used herein, refers to the sum of the processes by which a particular substance is changed by an organism. Such processes include, but are not limited to, hydrolysis reactions and reactions catalyzed by enzymes. Further information on metabolism may be obtained from The Pharmacological Basis of Therapeutics, 9th Edition, McGraw-Hill (1996). By way of example only, metabolites of natural amino acid polypeptides, non-natural amino acid polypeptides, modified natural amino acid polypeptides, or modified non-natural amino acid polypeptides may be identified either by administration of the natural amino acid polypeptides, non-natural amino acid polypeptides, modified natural amino acid polypeptides, or modified non-natural amino acid polypeptides to a host and analysis of tissue samples from the host, or by incubation of natural amino acid polypeptides, non-natural amino acid polypeptides, modified natural amino acid polypeptides, or modified non-natural amino acid polypeptides with hepatic cells in vitro and analysis of the resulting compounds.

The term "modified," as used herein refers to the presence of a change to a natural amino acid, a non-natural amino acid, a natural amino acid polypeptide or a non-natural amino acid polypeptide. Such changes, or modifications, may be obtained by post synthesis modifications of natural amino acids, non-natural amino acids, natural amino acid polypeptides or non-natural amino acid polypeptides, or by co-translational, or by post-translational modification of natural amino acids, non-natural amino acids, natural amino acid polypeptides or non-natural amino acid polypeptides.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "pharmaceutically acceptable", as used herein, refers to a material, including but not limited, to a salt, binder, adjuvant, excipient, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

In some embodiments the invention concerns polymers. The term "polymer," as used herein, refers to a molecule composed of repeated subunits. Such molecules include, but are not limited to, polypeptides, polynucleotides, or polysaccharides or polyalkylene glycols. Polymers of the invention can be linear or branched polymeric polyether polyols including, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymers have average molecular weights between about 0.1 kDa to about 100 kDa. Such polymers include, but are not limited to, between about 100 Da and about 100,000 Da or more. The molecular weight of the polymer may be between about 100 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, 400 Da, about 300 Da, about 200 Da, and about 100 Da. In some embodiments molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 2,000 to about 50,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly (ethylene glycol) molecule is a branched polymer. The molecular weight of the branched chain PEG may be between about 1,000 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. In other embodiments, the molecular weight of the branched chain PEG is between about 2,000 to about 50,000 Da. The term "PEGylating" or "PEGylated" is meant to refer to the covalent bonding of the specified synthetic amino acid to a polyethylene glycol (PEG) molecule. The method can comprise contacting an isolated a-PSMA ADCs polypeptide comprising a synthetic amino acid with a water soluble polymer comprising a moiety that reacts with the synthetic amino acid.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. Additionally, such "polypeptides," "peptides" and "proteins" include amino acid chains of any length, including full length proteins, wherein the amino acid residues are linked by covalent peptide bonds.

The term "post-translationally modified" refers to any modification of a natural or non-natural amino acid which occurs after such an amino acid has been translationally incorporated into a polypeptide chain. Such modifications include, but are not limited to, co-translational in vivo modifications, co-translational in vitro modifications (such as in a cell-free translation system), post-translational in vivo modifications, and post-translational in vitro modifications.

The terms "prodrug" or "pharmaceutically acceptable prodrug," as used herein, refers to an agent that is converted into the parent drug in vivo or in vitro, which does not abrogate the biological activity or properties of the drug, and is relatively nontoxic, i.e., the material may be administered to an individual without causing undesirable biological effects or interacting in a deleterious manner with any of the components of the composition in which it is contained. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are converted into active drug within the body through enzymatic or non-enzymatic reactions. Prodrugs may provide improved physiochemical properties such as better solubility, enhanced delivery characteristics, such as specifically targeting a particular cell, tissue, organ or ligand, and improved therapeutic value of the drug. The benefits of such prodrugs include, but are not limited to, (i) ease of administration compared with the parent drug; (ii) the prodrug may be bioavailable by oral administration whereas the parent is not; and (iii) the prodrug may also have improved solubility in pharmaceutical compositions compared with the parent drug. A prodrug includes a pharmacologically inactive, or reduced activity, derivative of an active drug. Prodrugs may be designed to modulate the amount of a drug or biologically active molecule that reaches a desired site of action through the manipulation of the properties of a drug, such as physiochemical, biopharmaceutical, or pharmacokinetic properties. An example, without limitation, of a prodrug would be a non-natural amino acid polypeptide which is administered as an ester (the "prodrug") to facilitate transmittal across a cell membrane where water solubility is detrimental to mobility and that is then metabolically hydrolyzed to the carboxylic acid, the active entity, once inside the cell where water solubility is beneficial. Prodrugs may be designed as reversible drug derivatives, for use as modifiers to enhance drug transport to site-specific tissues.

The term "prophylactically effective amount," as used herein, refers to an amount of a composition containing at least one non-natural amino acid polypeptide or at least one modified non-natural amino acid polypeptide prophylactically applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "recombinant host cell," also referred to as "host cell," refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome.

The term "subject" as used herein, refers to an animal which is the object of treatment, observation or experiment. By way of example only, a subject may be, but is not limited to, a mammal including, but not limited to, a human.

The term "substantially purified," as used herein, refers to a component of interest that may be substantially or essentially fre of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a natural amino acid polypeptide or a non-natural amino acid polypeptide may be purified from a native cell, or host cell in the case of recombinantly produced natural amino acid polypeptides or non-natural amino acid polypeptides. By way of example a preparation of a natural amino acid polypeptide or a non-natural amino acid polypeptide may be "substantially purified" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating material. By way of example when a natural amino acid polypeptide or a non-natural amino acid polypeptide is recombinantly produced by host cells, the natural amino acid polypeptide or non-natural amino acid polypeptide may be present it about 30%, about 25%, about 20%, about 15%, about 10%, about 5%, about 4%, about 3%, about 2%, or about 1% or less of the dry weight of the cells. By way of example when a natural amino acid polypeptide or a non-natural amino acid polypeptide is recombinantly produced by host cells, the natural amino acid polypeptide or non-natural amino acid polypeptide may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. By way of example, "substantially purified" natural amino acid polypeptides or non-natural amino acid polypeptides may have a purity level of about 30%, about 35%, about 40%, about 45%, about 50%, about 55%, about 60%, about 65%, about 70%, about 75%, about 80%, about 85% about 90%, about 95%, about 99% or greater as determined by appropriate methods, including, but not limited to, SDS/PAGE analysis, RP-HPLC, SEC, and capillary electrophoresis.

The term "therapeutically effective amount," as used herein, refers to the amount of a composition containing at least one non-natural amino acid polypeptide and/or at least one modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depends on conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

The term "toxic", or "toxic moiety" or "toxic group" or "cytotoxic" or "cytotoxic payload" or "payload" as used herein, refers to a compound which can cause harm, disturbances, or death. Toxic moieties include, but are not limited to, auristatin, DNA minor groove binding agent, DNA minor groove alkylating agent, enediyne, lexitropsin, duocarmycin, taxane, puromycin, dolastatin, maytansinoid, vinca alkaloid, AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, netropsin, podophyllotoxin (e.g. etoposide, teniposide, etc.), baccatin and its derivatives, anti-tubulin agents, cryptophysin, combretastatin, vincristine, vinblastine, vindesine, vinorelbine, VP-16, camptothecin, epothilone A, epothilone B, nocodazole, colchicines, colcimid, estramustine, cmadotin, discodermolide, maytansine, eleutherobin, mechlorethamine, cyclophosphamide, melphalan, carmustine, lomustine, semustine, streptozocin, chlorozotocin, uracil mustard, chlormethine, ifosfamide, chlorambucil, pipobroman, triethylenemelamine, triethylenethiophosphoramine, busulfan, dacarbazine, and temozolomide, ytarabine, cytosine arabinoside, fluorouracil, floxuridine, 6-thioguanine, 6-mercaptopurine, pentostatin, 5-fluorouracil, methotrexate, 10-propargyl-5,8-dideazafolate, 5,8-dideazatetrahydrofolic acid, leucovorin, fludarabine phosphate, pentostatine, gemcitabine, Ara-C, deoxycoformycin, mitomycin-C, L-asparaginase, azathioprine, brequinar, antibiotics (e.g., anthracycline, gentamicin, cefalotin, vancomycin, telavancin, daptomycin, azithromycin, erythromycin, rocithromycin, furazolidone, amoxicillin, ampicillin, carbenicillin, flucloxacillin, methicillin, penicillin, ciprofloxacin, moxifloxacin, ofloxacin, doxycycline, minocycline, oxytetracycline, tetracycline, streptomycin, rifabutin, ethambutol, rifaximin, etc.), antiviral drugs (e.g., abacavir, acyclovir, ampligen, cidofovir, delavirdine, didanosine, efavirenz, entecavir, fosfonet, ganciclovir, ibacitabine, imunovir, idoxuridine, inosine, lopinavir, methisazone, nexavir, nevirapine, oseltamivir, penciclovir, stavudine, trifluridine, truvada, valaciclovir, zanamivir, etc.), daunorubicin hydrochloride, daunomycin, rubidomycin, cerubidine, idarubicin, doxorubicin, epirubicin and mopholino derivatives, phenoxizone biscyclopeptides (e.g., dactinomycin), basic glycopeptides (e.g., bleomycin), anthraquinone glycosides (e.g., plicamycin, mithramycin), anthracenediones (e.g., mitoxantrone), azirinopyrrolo indolediones (e.g., mitomycin), macrocyclic immunosuppressants (e.g., cyclosporine, FK-506, tacrolimus, prograf, rapamycin etc.), navelbene, CPT-11, anastrazole, letrazole, capecitabine, reloxafine, cyclophosphamide, ifosamide, droloxafine, allocolchicine, Halichondrin B, colchicine, colchicine derivatives, maytansine, rhizoxin, paclitaxel, paclitaxel derivatives, docetaxel, thiocolchicine, trityl cysterin, vinblastine sulfate, vincristine sulfate, cisplatin, carboplatin, hydroxyurea, N-methylhydrazine, epidophyllotoxin, procarbazine, mitoxantrone, leucovorin, and tegafur. "Taxanes" include paclitaxel, as well as any active taxane derivative or pro-drug.

The terms "treat," "treating" or "treatment", as used herein, include alleviating, preventing, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments. The term "treat", "treating", or "treatment" can refers to the decrease, reduction or amelioration of one or more symptoms associated with prostate cancer.

As used herein, the term "water soluble polymer" refers to any polymer that is soluble in aqueous solvents. Such water soluble polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof polyvinyl ethyl ethers, and alpha-beta-poly[(2-hydroxyethyl)-DL-aspartamide, and the like, or mixtures thereof. By way of example only, coupling of such water soluble polymers to natural amino acid polypeptides or non-natural polypeptides may result in changes including, but not limited to, increased water solubility, increased or modulated serum half-life, increased or modulated therapeutic half-life relative to the unmodified form, increased bioavailability, modulated biological activity, extended circulation time, modulated immunogenicity, modulated physical association characteristics including, but not limited to, aggregation and multimer formation, altered receptor binding, altered binding to one or more binding partners, and altered receptor dimerization or multimerization. In addition, such water soluble polymers may or may not have their own biological activity.

As used herein, the term "modulated serum half-life" refers to positive or negative changes in the circulating half-life of a modified biologically active molecule relative to its non-modified form. By way of example, the modified biologically active molecules include, but are not limited to, natural amino acid, non-natural amino acid, natural amino acid polypeptide or non-natural amino acid polypeptide. By way of example, serum half-life is measured by taking blood samples at various time points after administration of the biologically active molecule or modified biologically active molecule and determining the concentration of that molecule in each sample. Correlation of the serum concentration with time allows calculation of the serum half-life. By way of example, modulated serum half-life may be an increased in serum half-life, which may enable an improved dosing regimen or avoid toxic effects. Such increases in serum may be at least about two-fold, at least about three-fold, at least about five-fold, or at least about ten-fold. Methods for evaluating serum half-life are known in the art and may be used for evaluating the serum half-life of antibodies and antibody drug conjugates of the present invention.

The term "modulated therapeutic half-life," as used herein, refers to positive or negative change in the half-life of the therapeutically effective amount of a modified biologically active molecule, relative to its non-modified form. By way of example, the modified biologically active molecules include, but are not limited to, natural amino acid, non-natural amino acid, natural amino acid polypeptide or non-natural amino acid polypeptide. By way of example, therapeutic half-life is measured by measuring pharmacokinetic and/or pharmacodynamic properties of the molecule at various time points after administration. Increased therapeutic half-life may enable a particular beneficial dosing regimen, a particular beneficial total dose, or avoids an undesired effect. By way of example, the increased therapeutic half-life may result from increased potency, increased or decreased binding of the modified molecule to its target, an increase or decrease in another parameter or mechanism of action of the non-modified molecule, or an increased or decreased breakdown of the molecules by enzymes such as, by way of example only, proteases. Methods for evaluating therapeutic half-life are known in the art and may be used for evaluating the therapeutic half-life of antibodies and antibody drug conjugates of the present invention.

BRIEF DESCRIPTION OF THE DRAWINGS

The novel features of the invention are set forth with particularity in the appended claims. A better understanding of the features and advantages of the present invention disclosure will be obtained by reference to the following detailed description that sets forth illustrative embodiments, in which the principles of the invention are utilized, and the accompanying drawings provided.

DETAILED DESCRIPTION OF THE INVENTION

Figure 1:
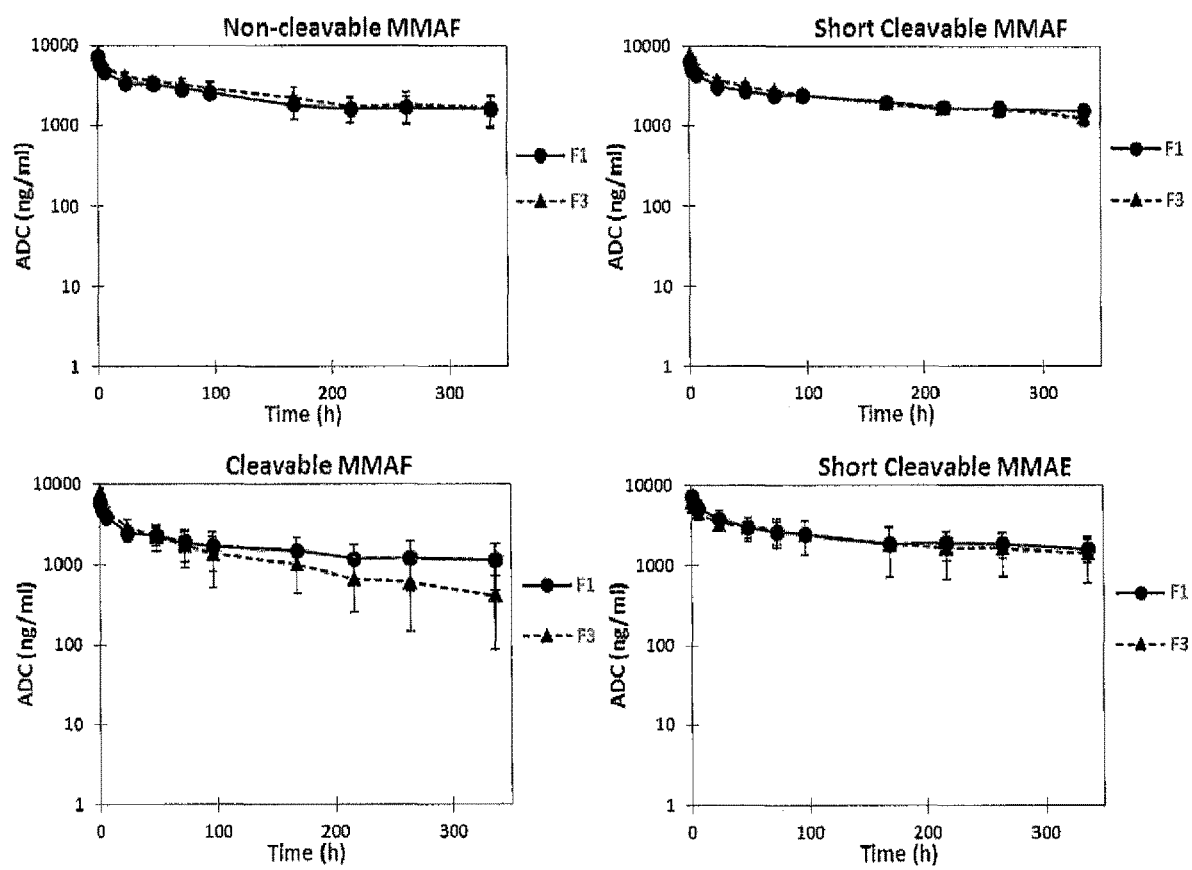
FIG. 1 depicts the pharmacokinetic studies conducted in mice with anti-PSMA antibody drug conjugates (ADC) using a non-cleavable MMAF, a short cleavable MMAF, a cleavable MMAF and a short cleavable MMAE. F1 represents detection of the antibody drug conjugate in the serum by antibody. F3 represents detection of the antibody drug conjugate in the serum by the drug-linker.

Before describing the present invention in detail, it is to be understood that this invention is not limited to particular methodologies, or compositions, or biological systems, which can, of course, vary. It is also to be understood that the terminology used herein is for the purpose of describing particular embodiments only and is not intended to be limiting. As used in this specification and the appended claims, the singular forms "a", "an" and "the" include plural referents unless the content clearly dictates otherwise. Thus, for example, reference to "a cell" includes a combination of two or more cells and the like.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless otherwise defined herein or below in the remainder of the specification, all technical and scientific terms used herein have the same meaning as commonly understood by those of ordinary skill in the art to which the invention belongs.

Antibody-based therapeutics have emerged as important components of therapies for an increasing number of human malignancies in such fields as oncology, inflammatory and infectious diseases. In most cases, the basis of the therapeutic function is the high degree of specificity and affinity the antibody-based drug has for its target antigen. Arming monoclonal antibodies with drugs, toxins, or radionuclides is yet another strategy by which monoclonal antibodies may induce therapeutic effect. By combining the exquisite targeting specificity of antibody with the tumor killing power of toxic effector molecules, immunoconjugates permit sensitive discrimination between target and normal tissue thereby resulting in fewer side effects than most conventional chemotherapeutic drugs. The toxins utilized can specifically, stably and irreversibly conjugate to unique sites in the antibody. This unique process of conjugation allows for the precise control of the location of the toxin on the antibody, and also the number of toxins conjugated to each antibody. Both of these features are critical for controlling biophysical characteristics and toxicities associated with ADCs. (See for example Jackson et al., 2014, Tian et al., 2014).

Anti-PSMA antibody drug conjugates provided in the present disclosure include humanized or chimeric monoclonal antibodies and variants that binds to the extracellular domain of prostate specific membrane antigen. Prostate specific membrane antigen is a type II membrane protein that is highly expressed, for example, in prostatic intraepithelial neoplasia (PIN), primary prostate cancers, and metastatic prostate cancers Anti-PSMA antibody disclosed herein can be any known PSMA antibody with at least one non-naturally or unnaturally encoded amino acid.

The present invention provides anti-PSMA antibodies and variants thereof having a non-naturally encoded amino acid that facilitate antibody conjugation to a drug (e.g. a drug, toxin molecule). In one embodiment, the ADC comprises an anti-PSMA antibody conjugated to a drug wherein the conjugation occurs via a non-naturally encoded amino acid in the antibody. In one embodiment, the ADC comprises an anti-PSMA antibody conjugated to a drug wherein the conjugation occurs via a non-naturally encoded amino acid in the heavy chain of the antibody. In one embodiment, the ADC comprises an anti-PSMA antibody conjugated to a drug wherein the conjugation occurs via a non-naturally encoded amino acid in the light chain of the antibody. In one embodiment, the ADC comprises a full-length antibody conjugated to a drug wherein the conjugation occurs via a non-naturally encoded amino acid in the antibody. In one embodiment, the ADC comprises a full-length antibody conjugated to a drug wherein the conjugation occurs via a non-naturally encoded amino acid in the heavy chain of the antibody. In one embodiment, the ADC comprises a full-length antibody conjugated to a drug wherein the conjugation occurs via a non-naturally encoded amino acid in the light chain of the antibody.

In some embodiments, the drug of the ADC is a cytotoxic drug or agent. In some aspects of the invention, the cytotoxic drug is selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. In some aspects of the invention, the cytotoxic drug is AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin, but not limiting to such.

In some aspects of the invention, the cytotoxic drug is an anti-tubulin agent. In some embodiments, the anti-tubulin agent is an auristatin, a vinca alkaloid, a podophyllotoxin, a taxane, a baccatin derivative, a cryptophysin, a maytansinoid, a combretastatin, or a dolastatin. In other aspects of the invention, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodennolide, maytansine, DM-1, or eleutherobin but not limiting to such.

In other aspects of the invention, the cytotoxic drug of the ADC is gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-ipoxygenase inhibitor, or a leukotriene receptor antagonist.

In some embodiments of the invention, the antibody of the ADC comprises a full length antibody or fragment thereof that: (a) binds to PSMA, and (b) is conjugated to a cytotoxic agent or an immunosuppressive agent, wherein the antibody-drug conjugate exerts: (a) a cytotoxic or cytostatic effect on a PSMA-expressing cancer cell line, or (b) a cytotoxic, cytostatic, or immunosuppressive effect on a PSMA-expressing immune cell, wherein the conjugation occurs at a non-naturally encoded amino acid in the antibody.

In some embodiments, the antibody, variant, or composition of the present disclosure may be an antibody, variant, or composition that binds to a PSMA receptor. In other embodiments of the present invention the antibody, variant, or composition may be an antibody, variant, or composition that binds to extracellular surface of PSMA receptor. In another embodiment of the present invention the antibody, variant, or composition disclosed may be an antibody, variant, or composition that bind to a PSMA dimer. In some embodiments the antibody, variant, or composition of the present disclosure may be an antibody, variant, or composition that has CDRs from J591 grafted onto the framework region of the variable region. In other embodiments the antibody, variant, or composition of the present invention disclosure may be an antibody, variant, or composition that has a non-naturally encoded amino acid. In some embodiments the antibody, variant, or composition may be an antibody, variant, or composition that is described by more than one of the embodiments elsewhere herein the present invention disclosure. In some embodiments the antibody, antibody variant or antibody composition(s) disclosed herein may be fully humanized. In other embodiments the antibody, antibody variant or antibody composition(s) disclosed herein may be chimeric. In some embodiments of the present invention the antibody may be an antibody that is full length antibody (Variable+Fc regions), Fab, bispecific, Fab-dimers, Fab-bispecific, Fab-trispecific, bispecific T-cell engagers, dual-affinity re-targeting antibody, IgG1/IgG3 bispecific antibody, diabody, bispecific diabody, scFv-Fc, minibody.

Methods, compositions, and techniques for creating and using dolastatin linker derivatives or analogs comprising at least one carbonyl, dicarbonyl, oxime, hydroxylamine, aldehyde, protected aldehyde, ketone, protected ketone, thioester, ester, dicarbonyl, hydrazine, azide, amidine, imine, diamine, keto-amine, keto-alkyne, alkyne, cycloalkyne, or ene-dione are well known to one of ordinary skill in the art, (see, for example, WO2013/185117, incorporated herein by reference in its entirety). Methods, compositions, and techniques for creating and using dolastatin linker derivatives or analogs comprising at least one non-natural amino acid or modified non-natural amino acid with an oxime, aromatic amine, heterocycle (e.g., indole, quinoxaline, phenazine, pyrazole, triazole, etc.) are also well known to the skilled artisan and described in, for example, WO2013/185117, incorporated herein by reference in its entirety. Such dolastatin linker derivatives comprising non-natural amino acids may contain further functionality, including but not limited to, a polymer, a water-soluble polymer, a derivative of polyethylene glycol; a second protein or polypeptide or polypeptide analog; an antibody or antibody fragment; and any combination thereof. Note that the various aforementioned functionalities are not meant to imply that the members of one functionality cannot be classified as members of another functionality. Indeed, there will be overlap depending upon the particular circumstances. By way of example only, a water-soluble polymer overlaps in scope with a derivative of polyethylene glycol, however the overlap is not complete and thus both functionalities are cited above.

Provided herein in some embodiments, is a toxic group linker derivative comprising a carbonyl, dicarbonyl, oxime, hydroxylamine, aldehyde, protected aldehyde, ketone, protected ketone, thioester, ester, dicarbonyl, hydrazine, azide, amidine, imine, diamine, keto-amine, keto-alkyne, alkyne, cycloalkyne, or ene-dione. In some embodiments, the toxic group derivative comprises any of the linkers disclosed herein. Methods, compositions, and techniques for creating and using toxic group derivatives or analogs comprising at least one non-natural amino acid or modified non-natural amino acid with an oxime, aromatic amine, heterocycle (e.g., indole, quinoxaline, phenazine, pyrazole, triazole, etc.) are described in WO2013/185117 (incorporated herein by reference in its entirety). In some embodiments, such toxic derivatives comprising non-natural amino acids may contain further functionality, including but not limited to, a polymer, a water-soluble polymer; a derivative of polyethylene glycol; a second protein or polypeptide or polypeptide analog; an antibody or antibody fragment; and any combination thereof. In specific embodiments, the toxic group is a tubulin inhibitor. In certain specific embodiments, the toxic group is dolastatin or auristatin. In other specific embodiments, the toxic group is dolastatin or auristatin derivative. Note that the various aforementioned functionalities are not meant to imply that the members of one functionality cannot be classified as members of another functionality. Indeed, there will be overlap depending upon the particular circumstances. By way of example only, a water-soluble polymer overlaps in scope with a derivative of polyethylene glycol, however the overlap is not complete and thus both functionalities are cited above.

Certain embodiments of the present invention describe preparations of certain toxic moieties with linkers that reduce the toxicity of the moiety in vivo while the toxic moiety retains pharmacological activity. In some embodiments, the toxicity of the linked toxic group, when administered to an animal or human, is reduced or eliminated compared to the free toxic group or toxic group derivatives comprising labile linkages, while retaining pharmacological activity. In some embodiments, increased doses of the linked toxic group (e.g., dolastatin linker derivatives, non-natural amino acid linked dolastatin derivatives) may be administered to animals or humans with greater safety. In certain embodiments, the non-natural amino acid polypeptides linked to a toxic moiety (e.g., dolastatin derivative) provides in vitro and in vivo stability. In some embodiments, the non-natural amino acid polypeptides linked to a toxic moiety (e.g., tubulin inhibitor, dolastatin-10 derivative) are efficacious and less toxic compared to the free toxic moiety (e.g., tubulin inhibitor, dolastatin-10).

Methodology and Techniques

The present disclosure encompasses methodologies and technologies well known in the art. These include conventional methods of mass spectroscopy, NMR, HPLC, protein chemistry, biochemistry, recombinant DNA techniques and pharmacology, within the skill of the art. Compounds of the present invention disclosure can be synthesized using several processes or schemes employed in the art. See for example, Dubowchik et al., Bioconjugate Chem. 13: 855-869, 2002; Doronina et al., Nature Biotechnology 21(7): 778-784, 2003; WO2012/166560; WO2013/185117, each incorporated herein by reference. Many methodologies and techniques for synthesis of pharmaceutical, diagnostic or therapeutic compounds are well known to one of ordinary skill in the art.

The present invention, unless otherwise indicated, also encompass conventional techniques of molecular biology (including recombinant techniques), cell biology, biochemistry and immunology, all within the skill of the art Such techniques are explained fully in the literature, such as, Molecular Cloning: A Laboratory Manual, Third Edition, Cold Spring Harbor Press, Cold Spring Harbor, NY (Sambrook et al. Eds., 2001); Oligonucleotide Synthesis: Methods And Applications (Methods in Molecular Biology), Herdewijn, P., Ed., Humana Press, Totowa, NJ; Oligonucleotide Synthesis (Gait, M. J., Ed., 1984); Methods In Molecular Biology, Humana Press, Totowa, NJ; Cell Biology: A Laboratory Notebook, Academic Press, New York, NY (Cellis, J. E., Ed., 1998); Animal Cell Culture (Frehney, R. I., Ed., 1987); Introduction To Cell And Tissue Culture Plenum Press, New York, NY, (Mther, J. P. and Roberts, P. E., Eds., 1998); Cell And Tissue Culture: Laboratory Procedures John Wiley and Sons, Hoboken, NJ, (Doyle, A. et al., Eds., 1993-8); Methods In Enzymology (Academic Press, Inc.) New York, NY; Weir's Handbook Of Experimental Immunology Wiley-Blackwell Publishers, New York, NY, (Herzenberg, L. A. et al. Eds., 1997); Gene Transfer Vectors For Mammalian Cells Cold Spring Harbor Press, Cold Spring Harbor, NY, (Miller, J. M. et al. Eds., 1987); Current Protocols In Molecular Biology, Greene Pub. Associates, New York, NY, (Ausubel, F. M. et al., Eds., 1987); PCR: The Polymerase Chain Reaction, Birkhauser, Boston, MA, (Mullis, K. et al., Eds., 1994); Current Protocols In Immunology, John Wiley and Sons, Hoboken, NJ, (Coligan, J. E. et al., eds., 1991); Short Protocols In Molecular Biology, Hoboken, NJ, (John Wiley and Sons, 1999); Immunobiology 7 Garland Science, London, UK, (Janeway, C. A. et al., 2007); Antibodies. Stride Publications, Devoran, UK, (P. Finch, 1997); Antibodies: A Practical Approach Oxford University Press, USA, New York, NY, (D. Catty., ed., 1989); Monoclonal Antibodies: A Practical Approach Oxford University Press, USA, New York NY, (Shepherd, P. et al. Eds., 2000); Using Antibodies: A Laboratory Manual Cold Spring Harbor Laboratory Press, Cold Spring Harbor, NY, (Harlow, E. et al. Eds., 1998); The Antibodies Harwood Academic Publishers, London, UK, (Zanetti, M. et al. Eds. 1995).

Dolastatin Linker Derivatives

In embodiments of the present invention disclosure dolastatin linker derivatives or analogs comprising at least one non-natural amino acid or modified non-natural amino acid with a carbonyl, dicarbonyl, oxime or hydroxylamine group may be utilized. Methods for selecting and designing a dolastatin linker derivative to be modified using the methods, compositions and techniques are well known in the art, see for example WO2013/185117, incorporated herein by reference in its entirety. Dolastatin linker derivative may be designed de novo, including by way of example only, as part of high-throughput screening process (in which case numerous polypeptides may be designed, synthesized, characterized and/or tested) or based on the interests of the researcher. The new dolastatin linker derivative may also be designed based on the structure of a known or partially characterized polypeptide. The principles for selecting which amino acid(s) to substitute and/or modify and the choice of which modification to employ are described in WO2013/185117, for example. Dolastatin linker derivative may be designed to meet the needs of the experimenter or end user. Such needs may include, but are not limited to, manipulating the therapeutic effectiveness of the polypeptide, improving the safety profile of the polypeptide, adjusting the pharmacokinetics, pharmacologics and/or pharmacodynamics of the polypeptide, such as, by way of example only, increasing water solubility, bioavailability, increasing serum half-life, increasing therapeutic half-life, modulating immunogenicity, modulating biological activity, or extending the circulation time. In addition, such modifications include, by way of example only, providing additional functionality to the polypeptide, incorporating an antibody, and any combination of the aforementioned modifications. Such dolastatin linker derivatives can be modified to contain an oxime, carbonyl, dicarbonyl, or hydroxylamine group. The dolastatin linker derivative may contain at least one, at least two, at least three, at least four, at least five, at least six, at least seven, at least eight, at least nine, or ten or more of a carbonyl or dicarbonyl group, oxime group, hydroxylamine group, or protected forms thereof. The dolastatin linker derivative can be the same or different, for example, there can be 1, 2, 3, 4, 5, 6, 7, 8, 9, 10, 11, 12, 13, 14, 15, 16, 17, 18, 19, 20, or more different sites in the derivative that comprise 1, 2, 3, 4, 5, 6, 7, 8, 9, 10, 11, 12, 13, 14, 15, 16, 17, 18, 19, 20, or more different reactive groups.

For example, dolastatin derivatives with linkers containing a hydroxylamine (also called an aminooxy) group allow for reaction with a variety of electrophilic groups to form conjugates, including but not limited to, with PEG or other water soluble polymers. Like hydrazines, hydrazides and semicarbazides, the enhanced nucleophilicity of the aminooxy group permits it to react efficiently and selectively with a variety of molecules that contain carbonyl- or dicarbonyl-groups, including but not limited to, ketones, aldehydes or other functional groups with similar chemical reactivity. (See, for example, Shao, J. and Tam, J., J. Am. Chem. Soc. 117:3893-3899, 1995; H. Hang and C. Bertozzi, Acc. Chem. Res. 34(9): 727-736, 2001). Whereas the result of reaction with a hydrazine group is the corresponding hydrazone, an oxime, however, results generally from the reaction of an aminooxy group with a carbonyl- or dicarbonyl-containing group such as, by way of example, a ketones, aldehydes or other functional groups with similar chemical reactivity. In some embodiments, dolastatin derivatives with linkers comprising an azide, alkyne or cycloalkyne allow for linking of molecules via cycloaddition reactions (e.g., 1,3-dipolar cycloadditions, azide-alkyne Huisgen cycloaddition, etc., described in U.S. Pat. No. 7,807,619 incorporated by reference herein to the extent relative to the reaction).

Thus, in certain embodiments described herein are dolastatin derivatives with linkers comprising a hydroxylamine, aldehyde, protected aldehyde, ketone, protected ketone, thioester, ester, dicarbonyl, hydrazine, amidine, imine, diamine, keto-amine, keto-alkyne, and ene-dione hydroxylamine group, a hydroxylamine-like group (which has reactivity similar to a hydroxylamine group and is structurally similar to a hydroxylamine group), a masked hydroxylamine group (which can be readily converted into a hydroxylamine group), or a protected hydroxylamine group (which has reactivity similar to a hydroxylamine group upon deprotection). In some embodiments, the dolastatin derivatives with linkers comprise azides, alkynes or cycloalkynes. Examples of such dolastatin linker derivatives are included elsewhere herein and in WO2013/185117 and WO2005/074650 (each incorporated herein by reference in its entirety).

Non-Natural Amino Acids

Non-naturally encoded amino acid site selection was based on surface exposure/site accessibility within the antibody and hydrophobic or neutral amino acid sites were selected to maintain the charge on the antibody. Methods for introducing non-natural amino acids inserted into sites in a protein are described for example in WO2010/011735 and in WO2005/074650. The present invention employs such methodologies and techniques. The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that canbe transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups. Oxime-based non-natural amino acids may be synthesized by methods well known in the art, (see for example WO2013/185117 and WO2005/074650), including: (a) reaction of a hydroxylamine-containing non-natural amino acid with a carbonyl- or dicarbonyl-containing reagent; (b) reaction of a carbonyl- or dicarbonyl-containing non-natural amino acid with a hydroxylamine-containing reagent; or (c) reaction of an oxime-containing non-natural amino acid with certain carbonyl- or dicarbonyl-containing reagents.

Non-natural amino acids that may be used in the methods and compositions described herein include, but are not limited to, amino acids comprising amino acids with novel functional groups, amino acids that covalently or noncovalently interact with other molecules, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into polypeptides via incorporation of non-natural amino acids into such polypeptides offer a variety of advantages and manipulations of polypeptides. For example, the unique reactivity of a carbonyl or dicarbonyl functional group (including a keto- or aldehyde-functional group) allows selective modification of proteins with any of a number of hydrazine- or hydroxylamine-containing reagents in vivo and in vitro. A heavy atom-non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The polypeptide with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Non-Natural Amino Acid Linked Dolastatin Derivatives

In other embodiments of the present invention described herein are methods, strategies and techniques for incorporating at least one dolastatin linker derivatives into a non-natural amino acid. The present invention described herein includes methods for producing, purifying, characterizing and using dolastatin linker derivatives containing at least one such non-natural amino acid. Also included with this aspect are compositions of and methods for producing, purifying, characterizing and using oligonucleotides (including DNA and RNA) that can be used to produce, at least in part, a dolastatin linker derivative containing at least one non-natural amino acid. Also included with this aspect are compositions of and methods for producing, purifying, characterizing and using cells that can express such oligonucleotides that can be used to produce, at least in part, a dolastatin linker derivative containing at least one non-natural amino acid.

Thus, dolastatin linker derivatives comprising at least one non-natural amino acid or modified non-natural amino acid with a carbonyl, dicarbonyl, alkyne, cycloalkyne, azide, oxime or hydroxylamine group are provided and described herein. In certain embodiments, dolastatin linker derivatives with at least one non-natural amino acid or modified non-natural amino acid with a carbonyl, dicarbonyl, alkyne, cycloalkyne, azide, oxime or hydroxylamine group include at least one post-translational modification at some position on the polypeptide. In some embodiments the co-translational or post-translational modification occurs via the cellular machinery (e.g., glycosylation, acetylation, acylation, lipid-modification, palmitoylation, palmitate addition, phosphorylation, glycolipid-linkage modification, and the like), in many instances, such cellular-machinery-based co-translational or post-translational modifications occur at the naturally occurring amino acid sites on the polypeptide, however, in certain embodiments, the cellular-machinery-based co-translational or post-translational modifications occur on the non-natural amino acid site(s) on the polypeptide.

In other embodiments, the post-translational modification does not utilize the cellular machinery, but the functionality is instead provided by attachment of a molecule (a polymer; a water-soluble polymer; a derivative of polyethylene glycol; a second protein or polypeptide or polypeptide analog; an antibody or antibody fragment; and any combination thereof) comprising a second reactive group to the at least one non-natural amino acid comprising a first reactive group (including but not limited to, non-natural amino acid containing a ketone, aldehyde, acetal, hemiacetal, alkyne, cycloalkyne, azide, oxime, or hydroxylamine functional group) utilizing chemistry methodology described herein, or others suitable for the particular reactive groups. In certain embodiments, the co-translational or post-translational modification is made in vivo in a eukaryotic cell or in a non-eukaryotic cell. In certain embodiments, the post-translational modification is made in vitro not utilizing the cellular machinery. Also included with this aspect are methods for producing, purifying, characterizing and using such dolastatin linker derivatives containing at least one such co-translationally or post-translationally modified non-natural amino acids.

Also included within the scope of the methods, compositions, strategies and techniques described herein are reagents capable of reacting with a dolastatin linker derivative (containing a carbonyl or dicarbonyl group, oxime group, alkyne, cycloalkyne, azide, hydroxylamine group, or masked or protected forms thereof) that is part of a polypeptide so as to produce any of the aforementioned post-translational modifications. In certain embodiments, the resulting post-translationally modified dolastatin linker derivative will contain at least one oxime group; the resulting modified oxime-containing dolastatin linker derivative may undergo subsequent modification reactions. Also included with this aspect are methods for producing, purifying, characterizing and using such reagents that are capable of any such post-translational modifications of such dolastatin linker derivative(s).

In certain embodiments, the polypeptide or non-natural amino acid linked dolastatin derivative includes at least one co-translational or post-translational modification that is made in vivo by one host cell, where the post-translational modification is not normally made by another host cell type. In certain embodiments, the polypeptide includes at least one co-translational or post-translational modification that is made in vivo by a eukaryotic cell, where the co-translational or post-translational modification is not normally made by a non-eukaryotic cell. Examples of such co-translational or post-translational modifications include, but are not limited to, glycosylation, acetylation, acylation, lipid-modification, palmitoylation, palmitate addition, phosphorylation, glycolipid-linkage modification, and the like. In one embodiment, the co-translational or post-translational modification comprises attachment of an oligosaccharide to an asparagine by a GlcNAc-asparagine linkage (including but not limited to, where the oligosaccharide comprises (GcNAc-Man)$_2$-Man-GlcNAc-GlcNAc, and the like). In another embodiment, the co-translational or post-translational modification comprises attachment of an oligosaccharide (including but not limited to, Gal-GaNAc, Gal-GcNAc, etc.) to a serine or threonine by a GalNAc-serine, a GaNAc-threonine, a GlcNAc-serine, or a GlcNAc-threonine linkage. In certain embodiments, a protein or polypeptide can comprise a secretion or localization sequence, an epitope tag, a FLAG tag, a polyhistidine tag, a GST fusion, and/or the like. Also included with this aspect are methods for producing, purifying, characterizing and using such polypeptides containing at least one such co-translational or post-translational modification. In other embodiments, the glycosylated non-natural amino acid polypeptide is produced in a non-glycosylated form. Such a non-glycosylated form of a glycosylated non-natural amino acid may be produced by methods that include chemical or enzymatic removal of oligosaccharide groups from an isolated or substantially purified or unpurified glycosylated non-natural amino acid polypeptide; production of the non-natural amino acid in a host that does not glycosylate such a non-natural amino acid polypeptide (such a host including, prokaryotes or eukaryotes engineered or mutated to not glycosylate such a polypeptide), the introduction of a glycosylation inhibitor into the cell culture medium in which such a non-natural amino acid polypeptide is being produced by a eukaryote that normally would glycosylate such a polypeptide, or a combination of any such methods. Also described herein are such non-glycosylated forms of normally-glycosylated non-natural amino acid polypeptides (by normally-glycosylated is meant a polypeptide that would be glycosylated when produced under conditions in which naturally-occurring polypeptides are glycosylated). Of course, such non-glycosylated forms of normally-glycosylated non-natural amino acid polypeptides (or indeed any polypeptide described herein) may be in an unpurified form, a substantially purified form, or in an isolated form.

Oxime-Containing Linked Dolastatin Derivatives

Non-natural amino acid dolastatin linked derivatives containing an oxime group allow for reaction with a variety of reagents that contain certain reactive carbonyl- or dicarbonyl-groups (including but not limited to, ketones, aldehydes, or other groups with similar reactivity) to form new non-natural amino acids comprising a new oxime group. Such an oxime exchange reaction allows for the further functionalization of dolastatin linked derivatives. Further, the original dolastatin linked derivative containing an oxime group may be useful in their own right as long as the oxime linkage is stable under conditions necessary to incorporate the amino acid into a polypeptide (e.g., the in vivo, in vitro and chemical synthetic methods described herein and in WO2013/185117 and WO2005/074650, each incorporated herein by reference).

Thus, in certain embodiments described herein are non-natural amino acid dolastatin linked derivatives with sidechains comprising an oxime group, an oxime-like group (which has reactivity similar to an oxime group and is structurally similar to an oxime group), a masked oxime group (which can be readily converted into an oxime group), or a protected oxime group (which has reactivity similar to an oxime group upon deprotection).

The methods and compositions for incorporation of one or more non-natural amino acids into a dolastatin linker derivative are well known in the art, (see for example WO2013/185117 and WO2005/074650, each incorporated herein by reference in its entirety). One or more non-natural amino acids may be incorporated at one or more particular positions which do not disrupt activity of the dolastatin linker derivative. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the dolastatin linker derivative. In some embodiments, the non-natural amino acid is linked at the C-terminus of the dolastatin derivative. In other embodiments, the non-natural amino acid is linked at the N-terminus of the dolastatin derivative. Any position of the dolastatin linker derivative is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to a receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. Alternatively, the sites identified as critical to biological activity may also be good candidates for substitution with a non-natural amino acid, again depending on the desired activity sought for the polypeptide. Another alternative would be to simply make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, see world wide web for rcsb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained.

Exemplary sites of incorporation of a non-natural amino acid include, but are not limited to, those that are excluded from potential receptor binding regions, or regions for binding to binding proteins or ligands may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three-dimensional crystal structure of a polypeptide with its associated ligand, receptor and/or binding proteins, a preference for conservative substitutions In one embodiment, the methods described herein include incorporating into the dolastatin linker derivative, where the dolastatin linker derivative comprises a first reactive group; and contacting the dolastatin linker derivative with a molecule (including but not limited to a second protein or polypeptide or polypeptide analog; an antibody or antibody fragment; and any combination thereof) that comprises a second reactive group. In certain embodiments, the first reactive group is a hydroxylamine moiety and the second reactive group is a carbonyl or dicarbonyl moiety, whereby an oxime linkage is formed. In certain embodiments, the first reactive group is a carbonyl or dicarbonyl moiety and the second reactive group is a hydroxylamine moiety, whereby an oxime linkage is formed. In certain embodiments, the first reactive group is a carbonyl or dicarbonyl moiety and the second reactive group is an oxime moiety, whereby an oxime exchange reaction occurs. In certain embodiments, the first reactive group is an oxime moiety and the second reactive group is carbonyl or dicarbonyl moiety, whereby an oxime exchange reaction occurs.

In some cases, the dolastatin linker derivative incorporation(s) will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility (including but not limited to, when expressed in E. coli or other host cells) of the polypeptide. In some embodiments sites are selected for substitution with a naturally encoded or non-natural amino acid in addition to another site for incorporation of a non-natural amino acid for the purpose of increasing the polypeptide solubility following expression in E. coli, or other recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, OST, etc.) or linked molecules (including but not limited to, biotin) that improve detection (including but not limited to, GFP), purification, transport thru tissues or cell membranes, prodrug release or activation, size reduction, or other traits of the polypeptide.

In some embodiments a payload or toxin moiety is employed in the anti PSMA antibody drug conjugates of the present invention disclosure. Examples of payloads can include in a non-limiting manner: inhibitors of DNA replication, inhibitors of DNA transcription, inhibitors of RNA translation, inhibitors of cell division, inhibitors of cell signaling, kinase inhibitors, tubulin polymerase inhibitors, tubulin depolymerizing agents, DNA cleavage agents, DNA binding agents, RNA polymerase inhibitors, auristatins, dolastatins, MMAF, MMAE, MMAD, duocarmycin analogs, pyrrolobenzodiazepine (PBD) analogs, tubulysin analogs, maytansine analogs, amanitin analogs, cryptophycin analogs, epothilone analogs, calicheamicin analogs, doxorubicin analogs, camptothecin analogs.

In other embodiments of the present invention are provided drug payload linkers. Anti-tubulin inhibitors were chosen as the payload in combination with cleavable, short cleavable and non-cleavable linkers. In an exemplary manner, the payload linker combination of the present invention disclosure can include, but is not limited to, cleavable, non-cleavable, short cleavable payload linkers. Cleavable payload linkers can include cleavable dipeptides, (including, but not limited to Val-Cti, Val-Ala, Val-Lys and Ala-Ala), hydrazine linkage, disulfide linkage or pyrophosphate linkage. Example of payload linkers employed in anti-PSMA antibody drug conjugate of the present disclosure includes non-cleavable MMAE, non-cleavable MMAF, Val-Citruline-Acetyl MMAF, short Val-Citruline-Acetyl MMAF, or short Val-Citruline-Acetyl MMAE. Both MMAE and MMAF were utilized in the study. Non-limiting examples of dolastatin linker derivatives include the following:

Non-cleavable MMAF having the structure:

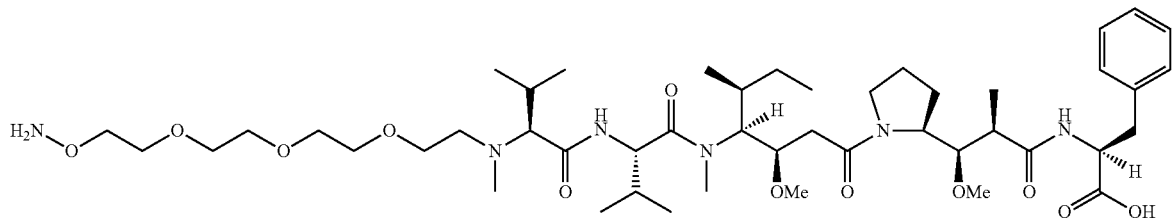 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCOCCOCCON)C(C)C]

Non-cleavable MMAE having the structure:
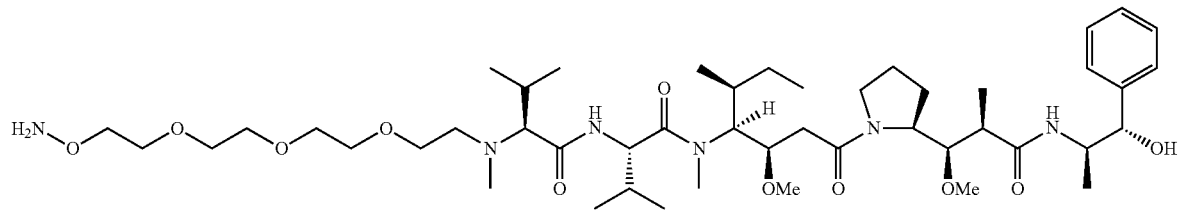 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)CCOCCOCCOCCON)C(C)C]
Cleavable or Val-Citruline-Acetyl (Val-Cit) MMAF having the structure:
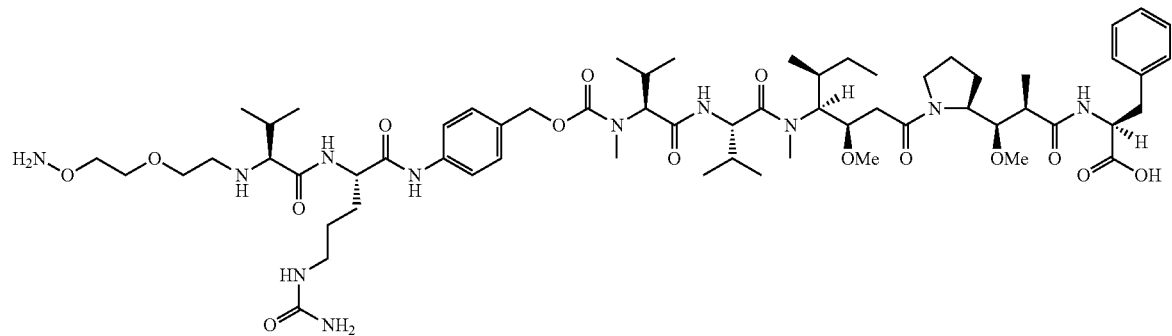 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)[C@H](CCCNC(N)=O)NC(=O)[C@@H](NCCOCCON)C(C)C)cc1)C(C)C]
Short-cleavable or short Val-Citruline-Acetyl (Val-Cit) MMAF having the structure:
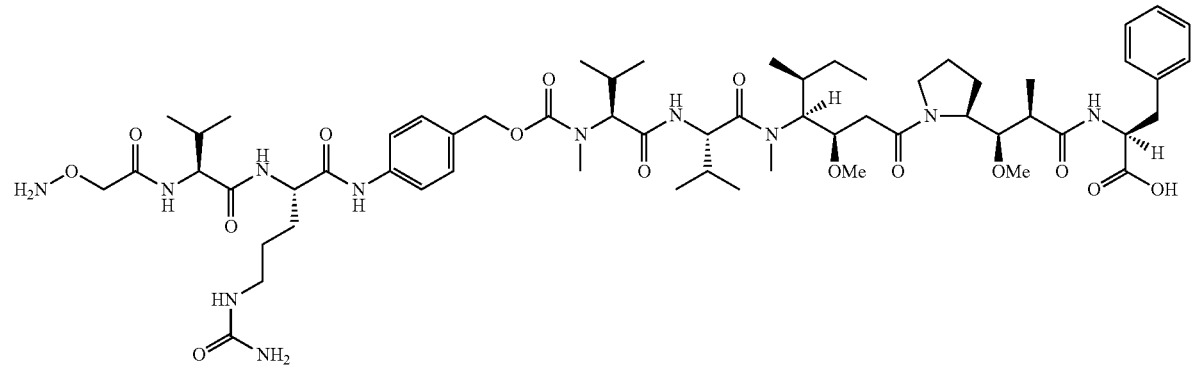 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CON)C(C)C)cc1)C(C)C]
Short-cleavable or short Val-Citruline-Acetyl (Val-Cit) MMAE having the structure:
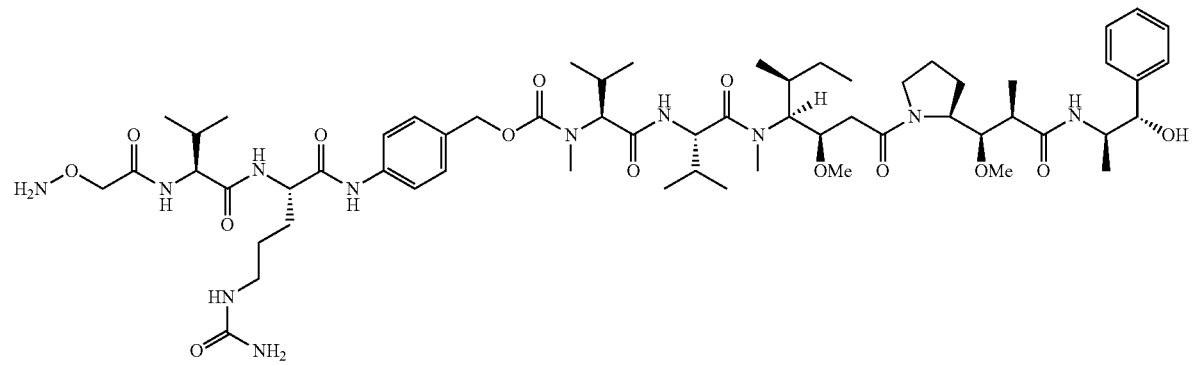 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CON)C(C)C)cc1)C(C)C]

Table 1 provides drug-linkers compounds that can be employed with the anti PSMA antibody or antibody drug conjugates of the present invention. Synthesis of such payload linkers are well known to the skilled artisan. See for example See for example, as incorporated herein by reference, Dubowchik et al., *Bioconjugate Chem.* 13: 855-869, (2002); Doronina et al., *Nature Biotechnology* 21(7): 778-784, (2003); WO2012/166560; WO2013/185117.

TABLE 1

Drug-linker Compounds

| Example | Structure |
|---|---|
| 1 | 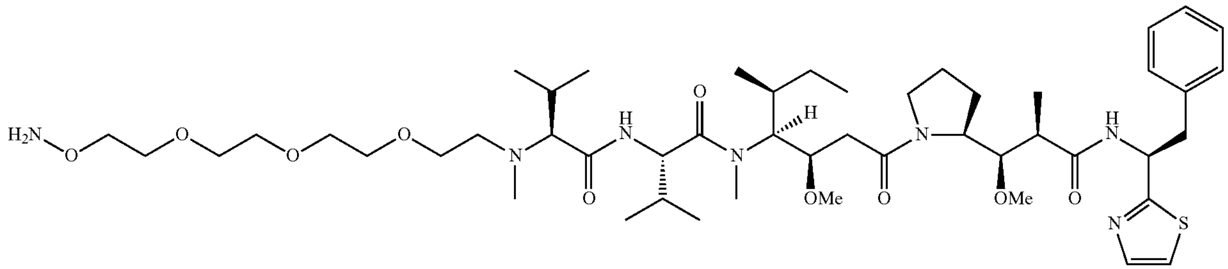 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCOCCOCCON)C(C)C] |
| 2 | 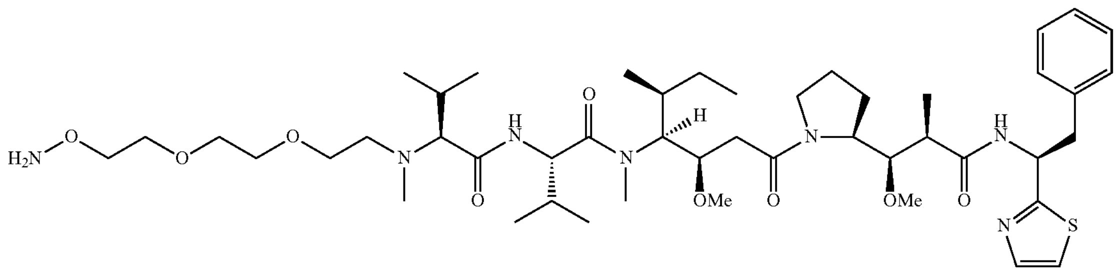 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCOCCON)C(C)C] |
| 3 | 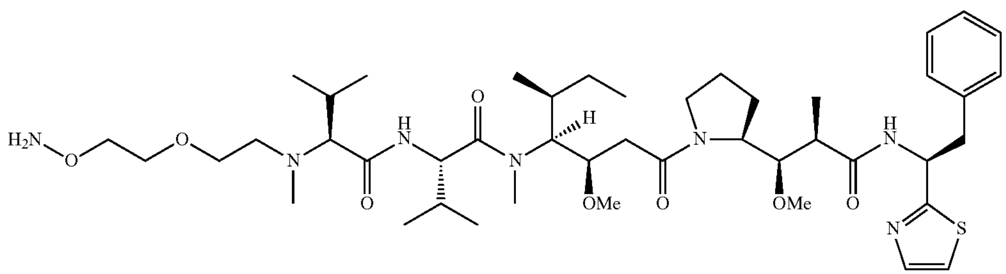 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCON)C(C)C] |

TABLE 1-continued

Drug-linker Compounds

| Example | Structure |
|---|---|
| 4 | (structure) |
| 5 | (structure) |
| 6 | (structure) |
| 7 | (structure) |

TABLE 1-continued
Drug-linker Compounds
| Example | Structure |
|---|---|
| 8 | 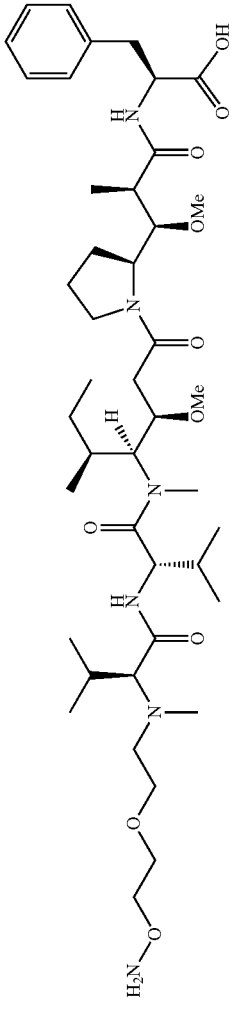 |
| 9 | 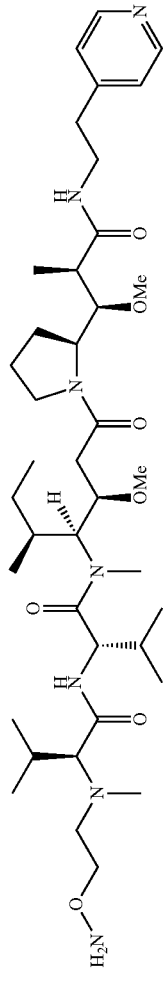 |
| 10 | 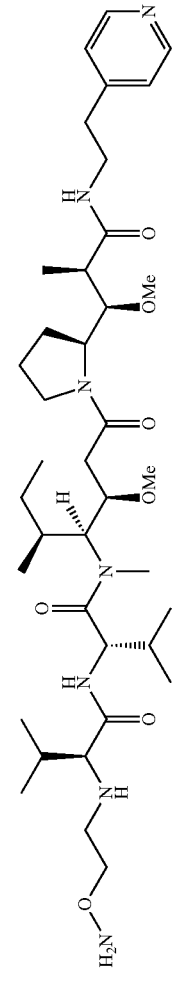 |
| 11 | 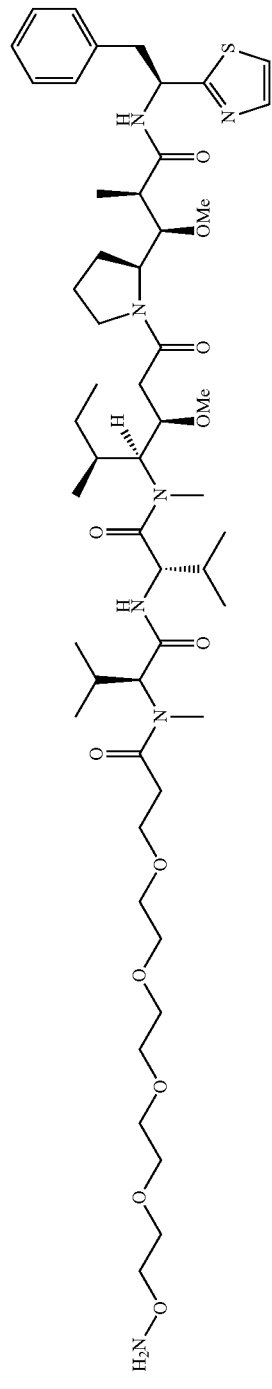 |

TABLE 1-continued

Drug-linker Compounds

| Example | Structure |
|---|---|
| 12 | 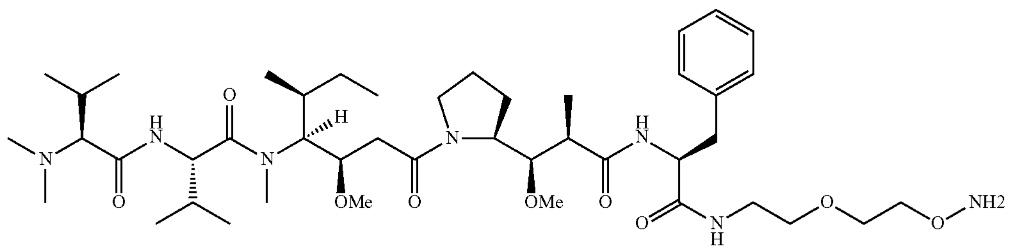 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCON)OC)N(C)C(=O)[C@@H](NC(=O)[C@H](C(C)C)N(C)C)C(C)C] |
| 13 | 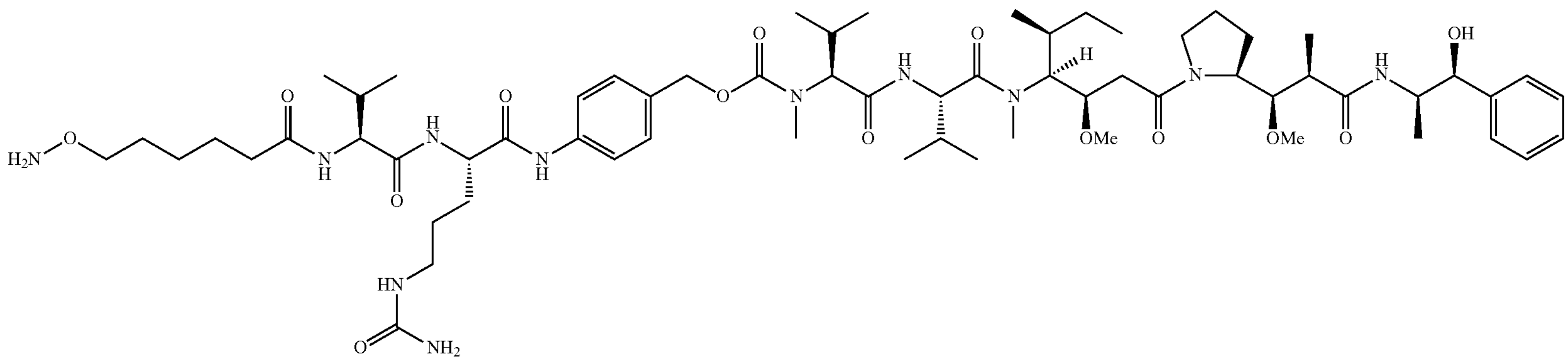 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCON)C(C)C)cc1)C(C)C] |
| 14 | 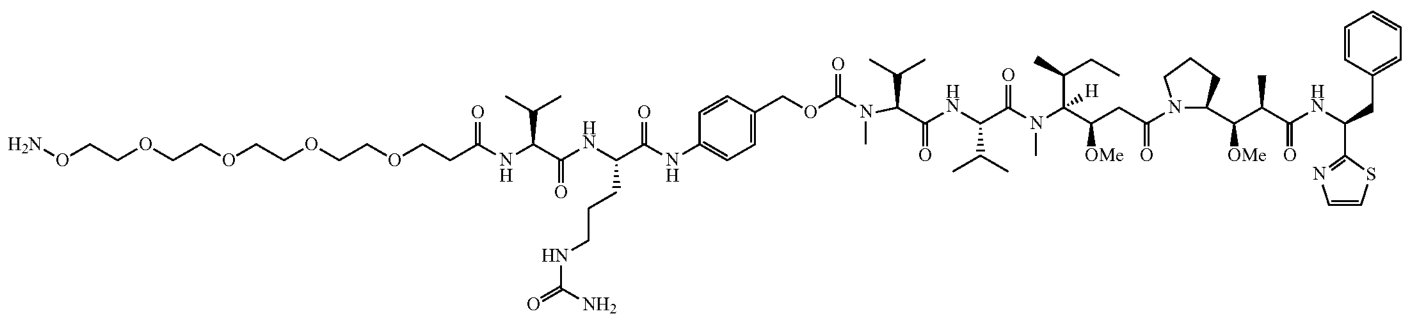 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCOCCOCCOCCOCCON)C(C)C)cc1)C(C)C] |

TABLE 1-continued
Drug-linker Compounds
| Example | Structure |
|---|---|
| 15 | 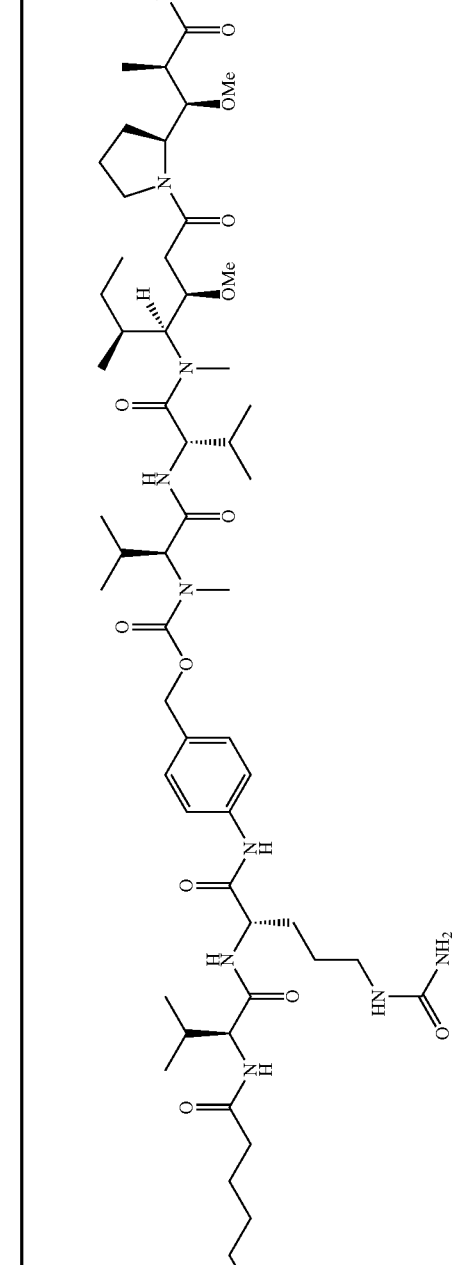 |
| 16 | 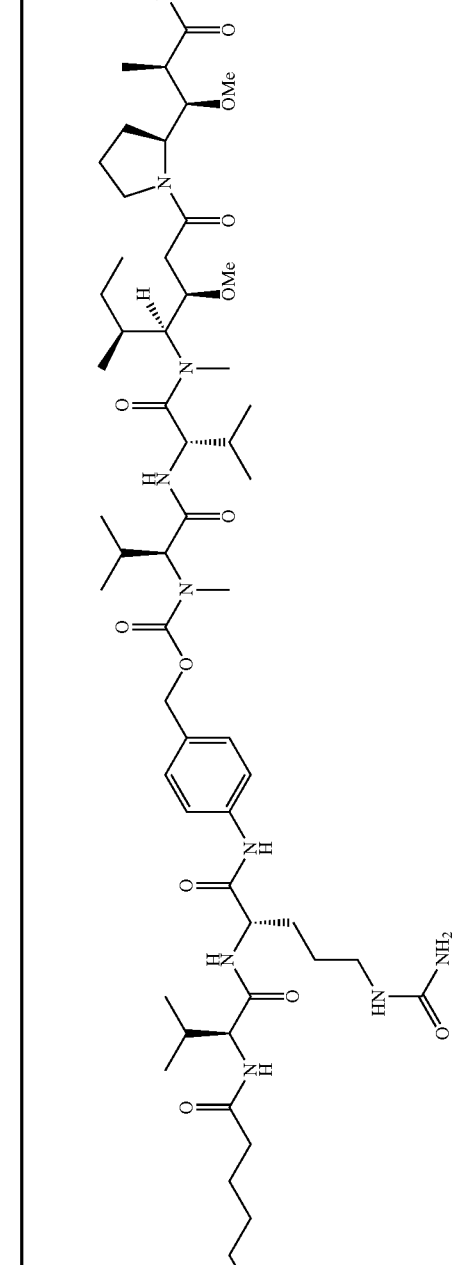 |

TABLE 1-continued
Drug-linker Compounds
| Example | Structure |
|---|---|
| 17 | 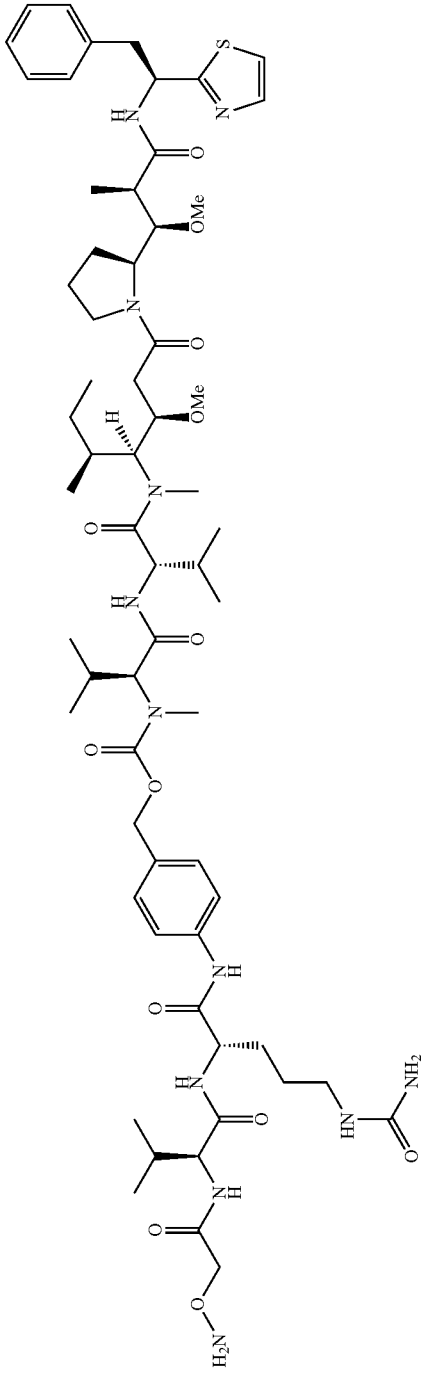 |
| 18 | 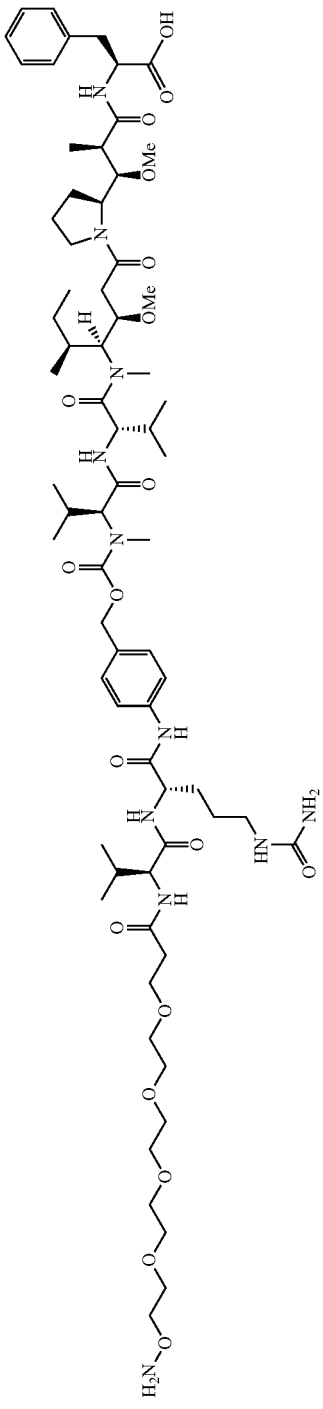 |

TABLE 1-continued

Drug-linker Compounds

| Example | Structure |
|---|---|
| 19 | 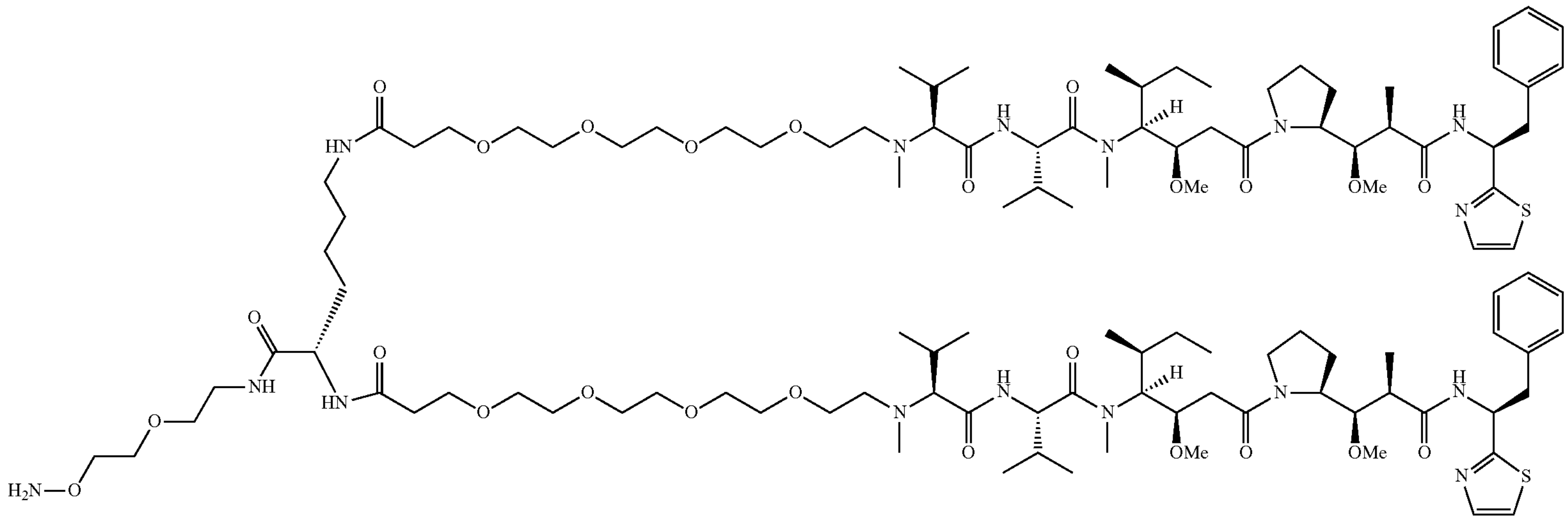 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)CCOCCOCCOCCOCCC(=O)NCCCC[C@H](NC(=O)CCOCCOCCOCCOCCN(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)c1nccs1)OC)C(C)C)C(C)C)C(=O)NCCOCCON)C(C)C] |

TABLE 1-continued
Drug-linker Compounds
| Example | Structure |
|---|---|
| 20 | 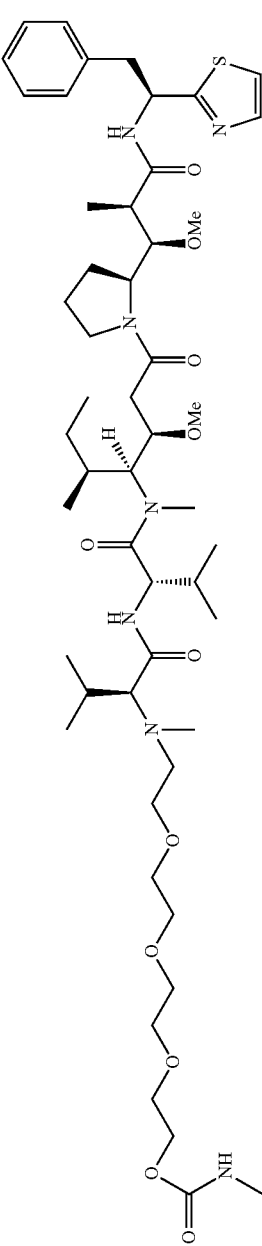 |

TABLE 1-continued
Drug-linker Compounds
| Example | Structure |
|---|---|
| 21 | 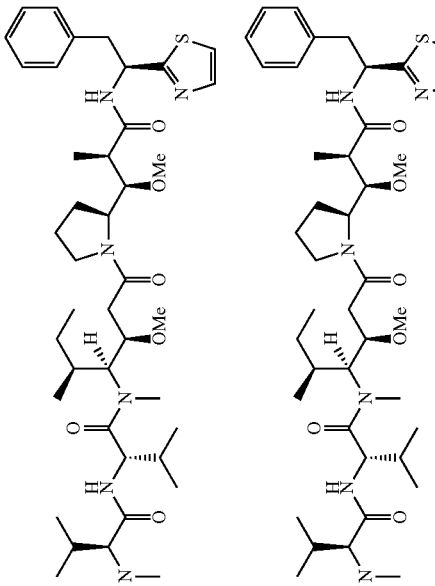 |

TABLE 1-continued

Drug-linker Compounds

| Example | Structure |
|---|---|
| 22 | 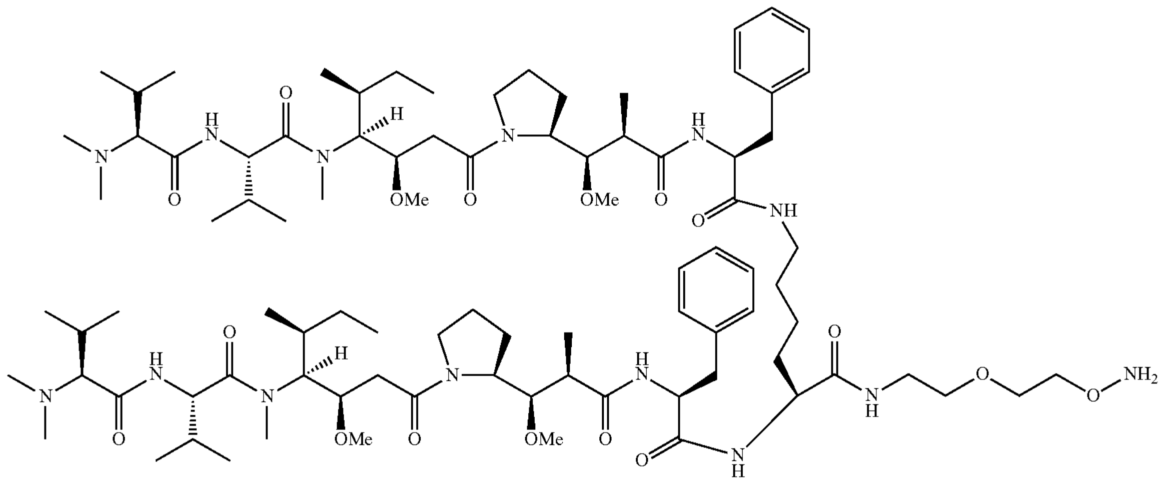 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCCC[C@H](NC(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C)C(=O)NCCOCCON)OC)N(C)C(=O)[C@@H](NC(=O)[C@H](C(C)C)N(C)C)C(C)C] |
| 23 | 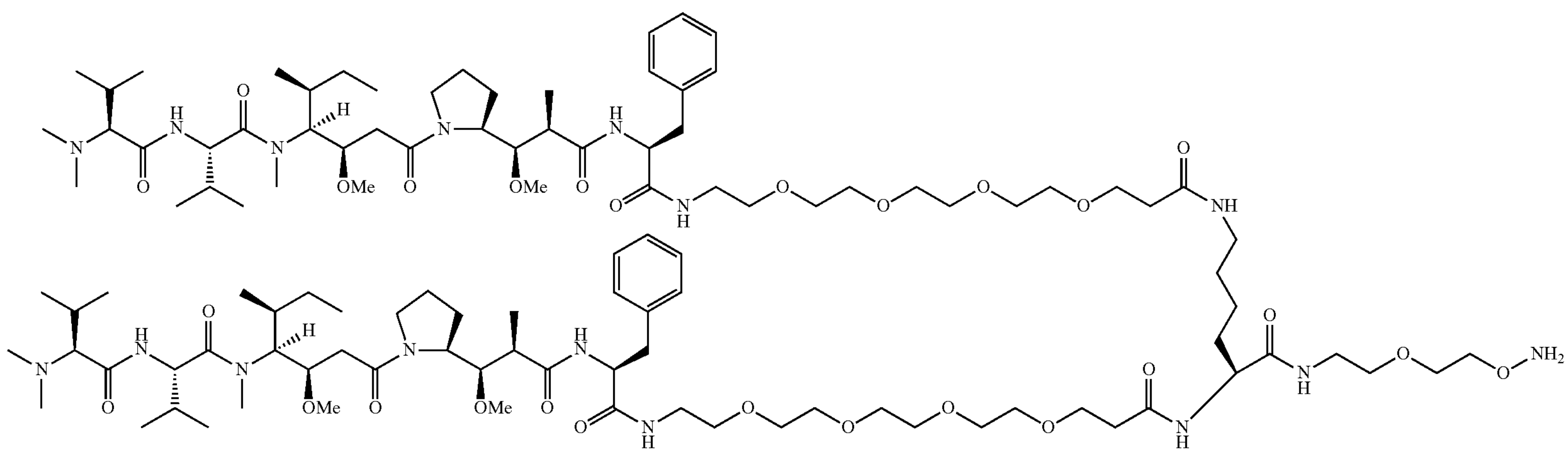 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCOCCOCCC(=O)NCCCC[C@H](NC(=O)CCOCCOCCOCCOCCNC(=O)[C@H](Cc1ccccc1)NC(=O)[C@H](C)[C@@H](OC)[C@@H]1CCCN1C(=O)C[C@@H](OC)[C@H]([C@@H](C)CC)N(C)C(=O)[C@@H](NC(=O)[C@H](C(C)C)N(C)C)C(C)C)C(=O)NCCOCCON)OC)N(C)C(=O)[C@@H](NC(=O)[C@H](C(C)C)N(C)C)C(C)C] |

Generating Anti-PSMA ADC Conjugated with PSMA Targeting Ligand

In other embodiments of the invention disclosure targeting ligands are included. Such ligands include those that bind to the active site of PSMA receptor, ligands that are inhibitors of glutamate carboxypeptidase enzymatic activity of PSMA receptor, and ligands used for imaging. The invention disclosure also includes those ligands with sub-pico to sub-nano molar binding affinity range.

Anti-PSMA ADCs conjugated with PSMA targeting ligand can be generated as described herein. One method of generation involves sequential conjugation where the toxin-linker is conjugated to the antibody by cysteine-maleimide conjugation method followed by conjugation of PSMA-targeting ligand at specific sites on the antibody based on proprietary oxime ligation method. The maleimide conjugation is performed by reduction of the disulfide bridges between heavy and light chains of the antibody facilitated by addition of relevant reducing agents. The disulfide bonds of the antibody can be reduced by incubating a reaction mixture formulated in pH ranging from 6 to 7.4 consisting of antibody and 3 to 9 molar fold higher reducing agent. The reaction mixture can be incubated at 37° C. for 2 hrs to obtain a drug:antibody ratio of 3 to 4. The toxin conjugated antibody is then buffer exchanged into a reaction mixture with pH ranging between 4 and 5 containing 10 molar fold higher PSMA targeting ligand. The reaction of the toxin conjugated antibody with the PSMA targeting ligand can be performed by incubating at room temperature with gentle shaking for 8 to 16 hours. Usually the amount of PSMA targeting ligand to antibody range between 1.8 and 2 generated by this method. Unconjugated components from the reaction mixture is removed by running through a cation exchange column and buffer exchanged into a proprietary formulation buffer that is isotonic with body fluids of mouse and human. In another method, the PSMA targeting ligand and the toxin can be conjugated at specific sites on the antibody in a single step by oxime-based conjugation chemistry. This single step conjugation can be facilitated by designing a branched linker containing both the PSMA targeting ligand and toxin. The single step conjugation can be performed by proprietary oxime and cyclo-octyne based click chemistry. Unconjugated components can be removed from the reaction mixture by running through a cation exchange purification column. The purified material is then formulated in an isotonic buffer. In exemplary embodiments PSMA targeting ligands, (L represents a linker), include, but are not limited to, the following:

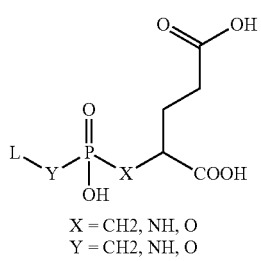

X = CH2, NH, O
Y = CH2, NH, O

-continued

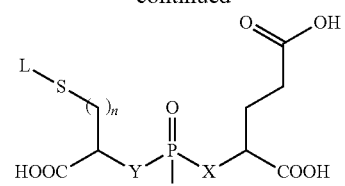

X = CH2, NH, O
Y = CH2, NH, O

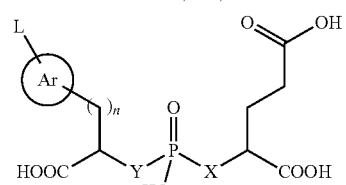

X = CH2, NH, O
Y = CH2, NH, O

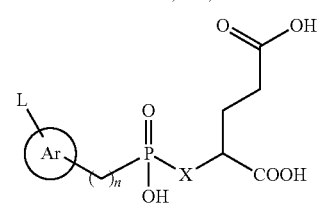

X = CH2, NH, O

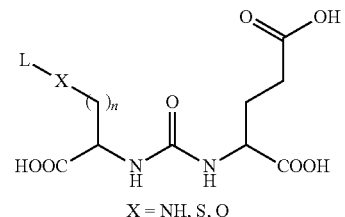

X = NH, S, O

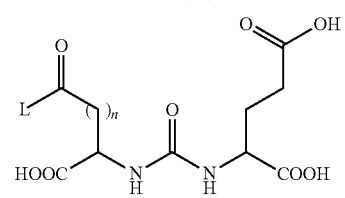

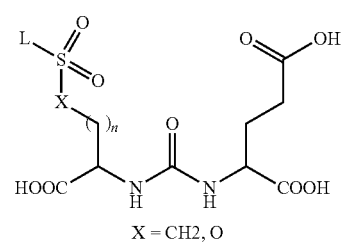

X = CH2, O

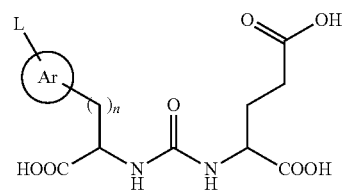

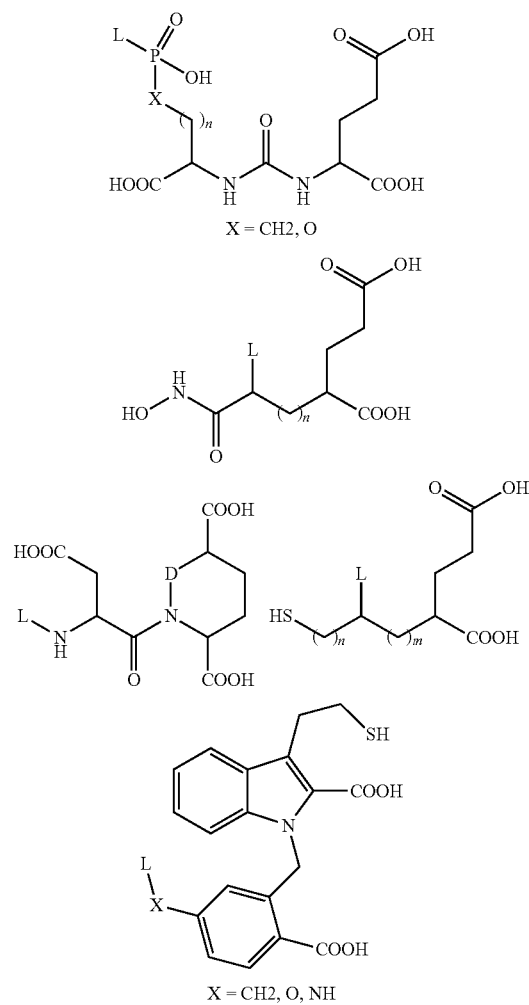
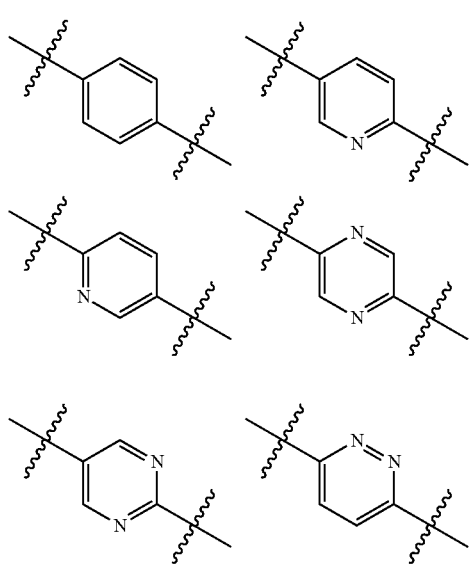
Ar: can be any 5,6 member aromatic rings or fused aromatic rings, such as (but not limited to)
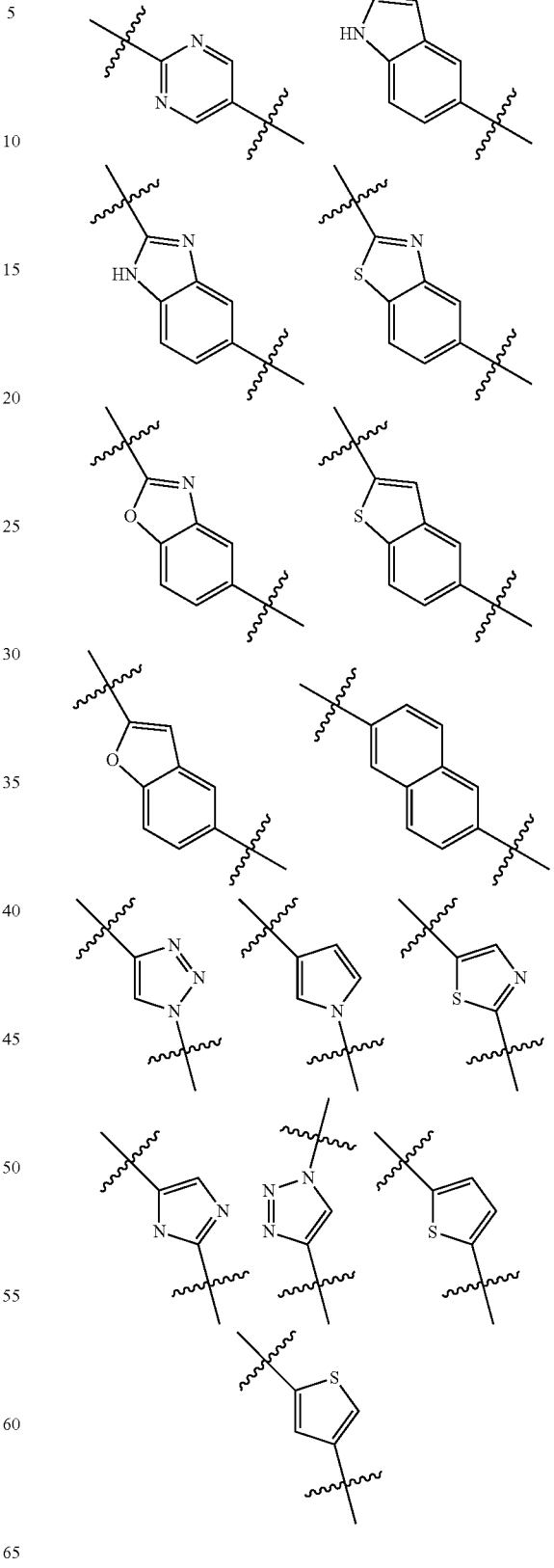
In exemplary embodiments, PSMA ligands of the present invention disclosure can include those compounds having an N-terminus targeting ligand and a C-terminus conjugation portion or part. In other exemplary aspects of the present invention, PSMA targeting ligands can include the following (Table 2), but are not limited to such:

TABLE 2

Targeting-ligands

| Example | Structure |
|---|---|
| 1 | 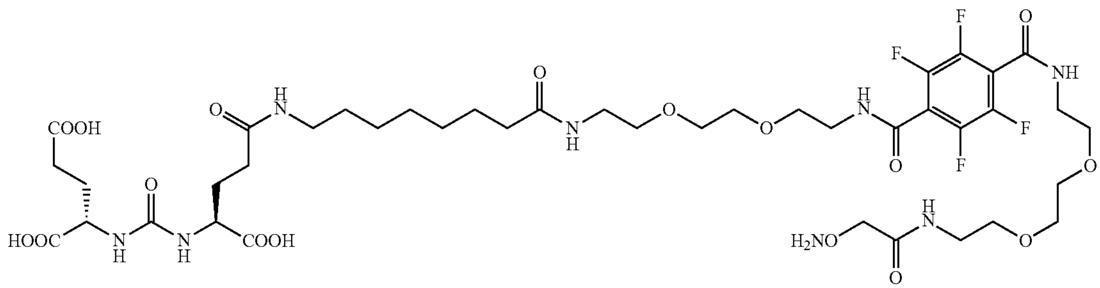 |
| 2 | 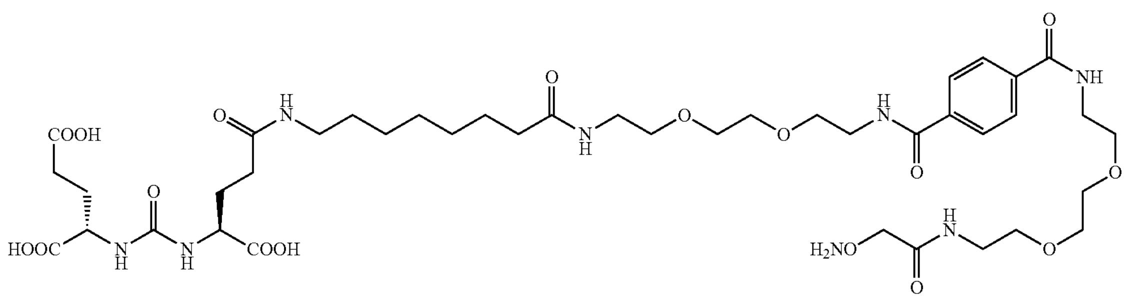 |
| 3 | 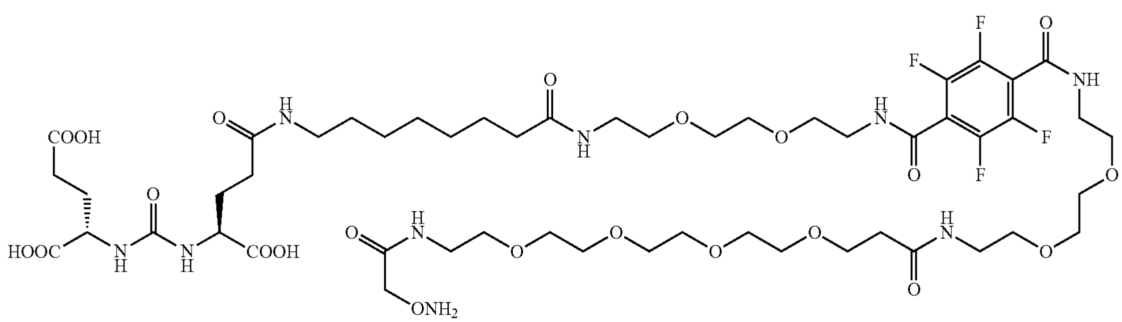 |
| 4 | 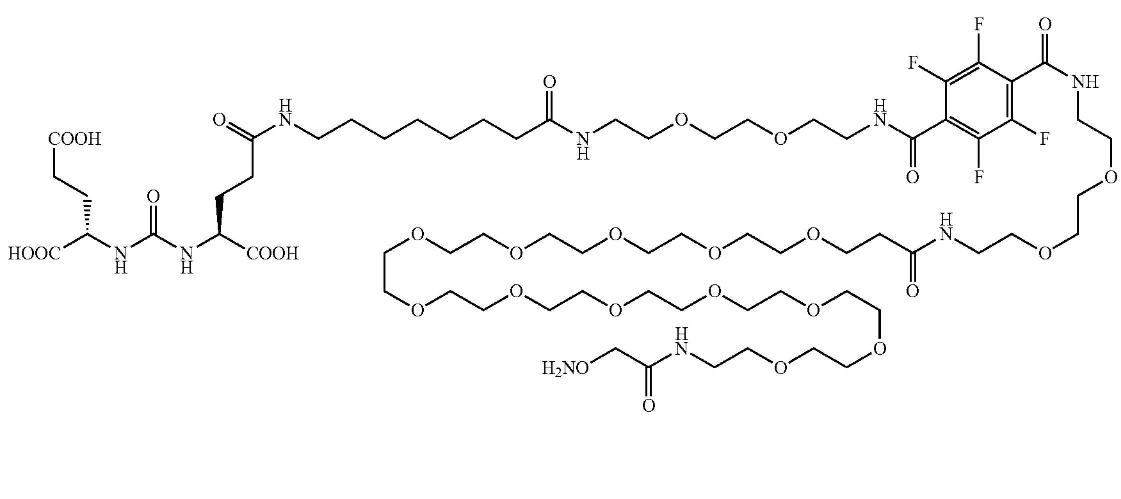 |

TABLE 2-continued

Targeting-ligands

| Example | Structure |
|---|---|
| 5 | 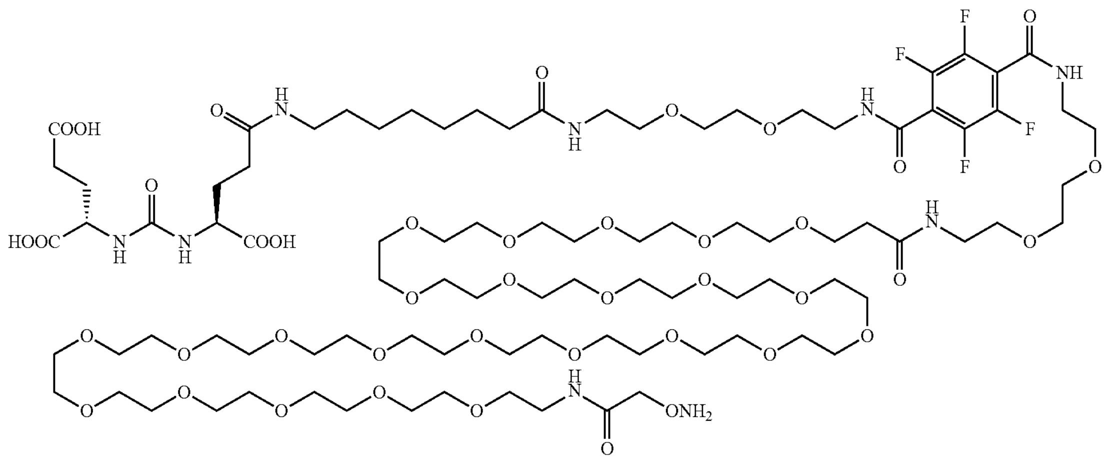 |
| 6 | 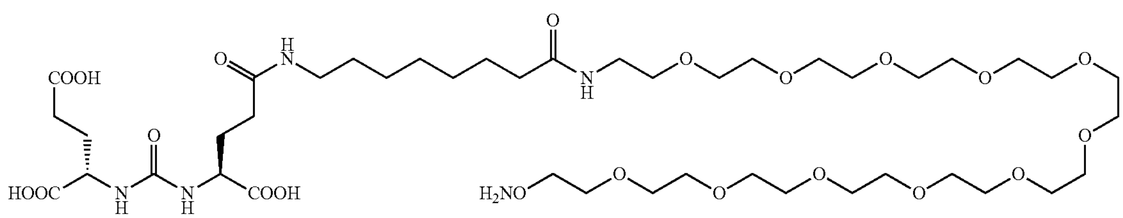 |

In other exemplary embodiments, the present invention disclosure includes PSMA targeting ligands and linkers wherein the linkage between the target ligand and the linker can be, in a nonlimiting manner:

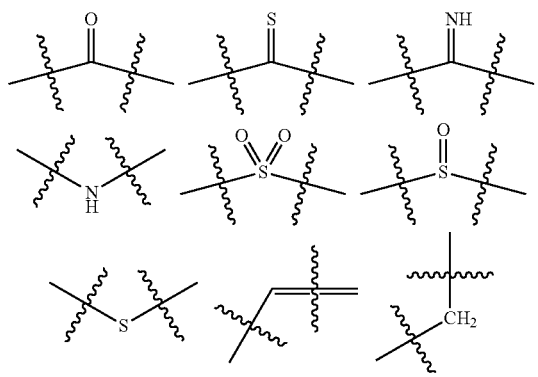

-continued

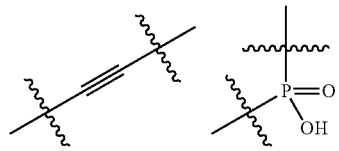

and the linkage can be hydrogen substituted.

In other aspects of the present invention the linker can be, in a non-limiting manner, polyethylene glycol (PEG), alkyl, alkene, alkyne, amine, aryl, or amino acids. Chemistry, methodology and techniques for connecting linkers are well known in the art.

In another exemplary embodiment, the present invention disclosure includes PSMA targeting ligands with toxins (Table 3) including, but not limited to:

TABLE 3
Ligands-Toxins
| Example | Structure |
|---|---|
| 1 | 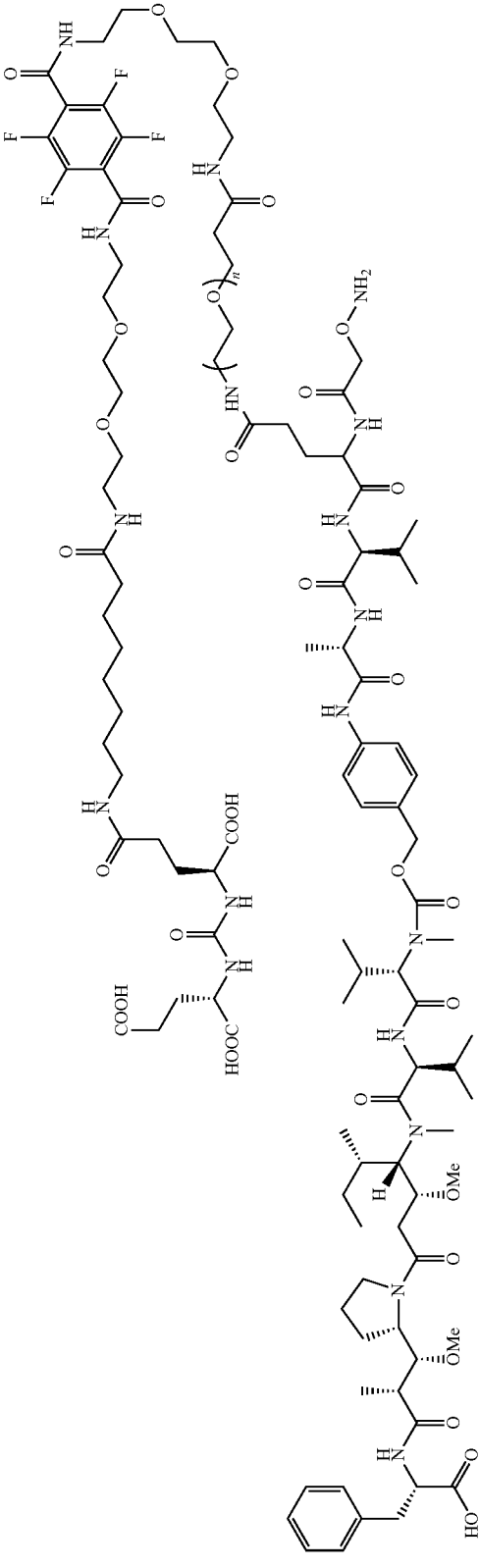 |
| 2 | 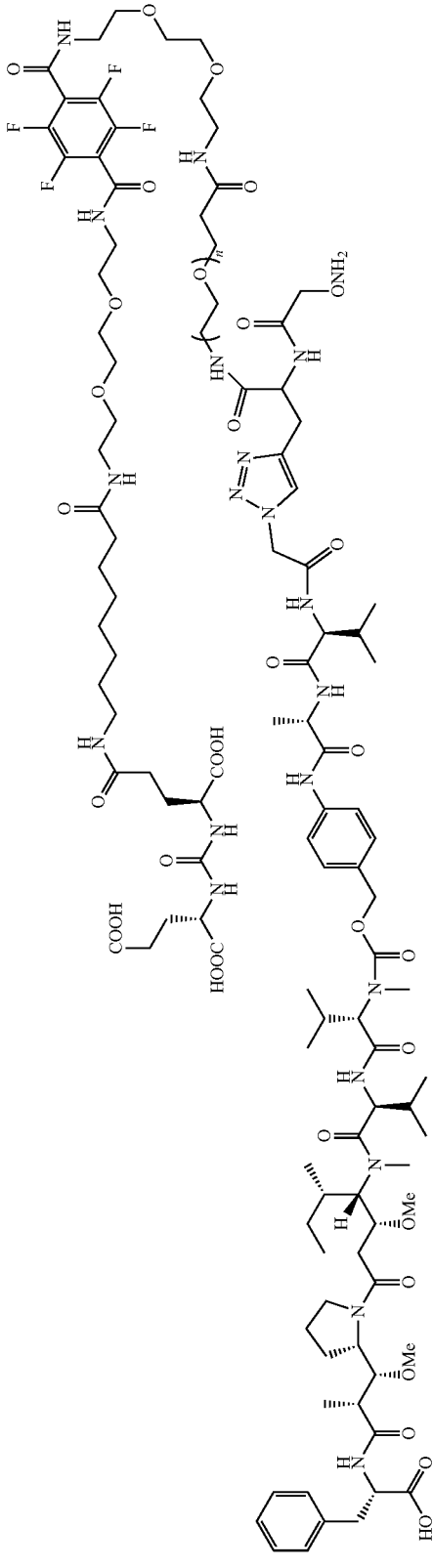 |

TABLE 3-continued

Ligands-Toxins

| Example | Structure |
|---|---|
| 3 | (chemical structure) |
| 4 | (chemical structure) |

TABLE 3-continued

Ligands-Toxins

| Example | Structure |
|---|---|
| 5 | 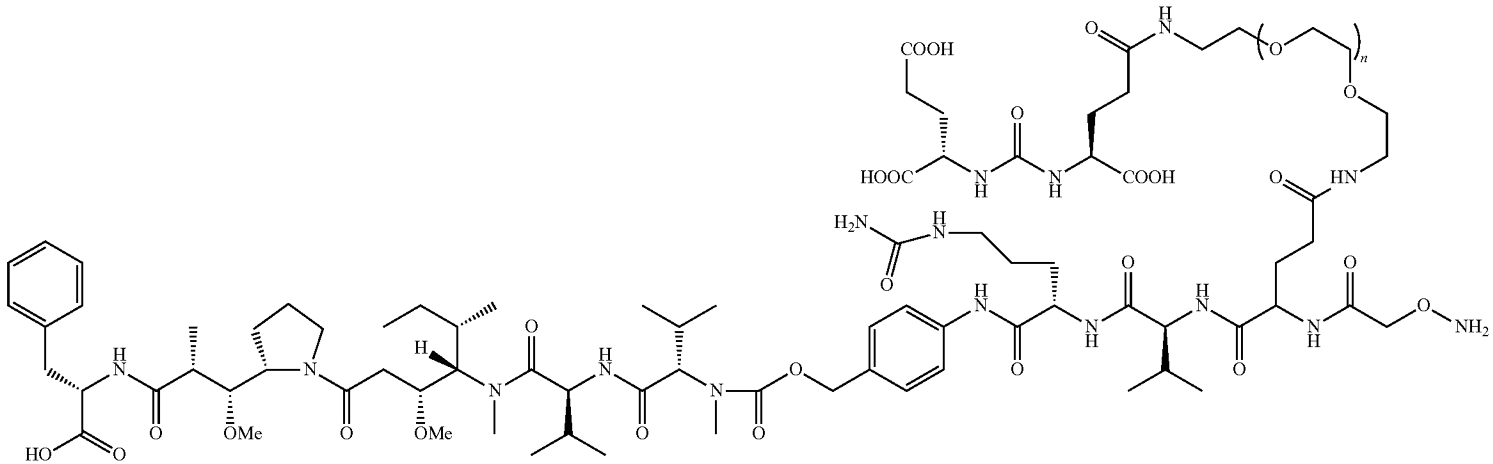 |
| 6 | 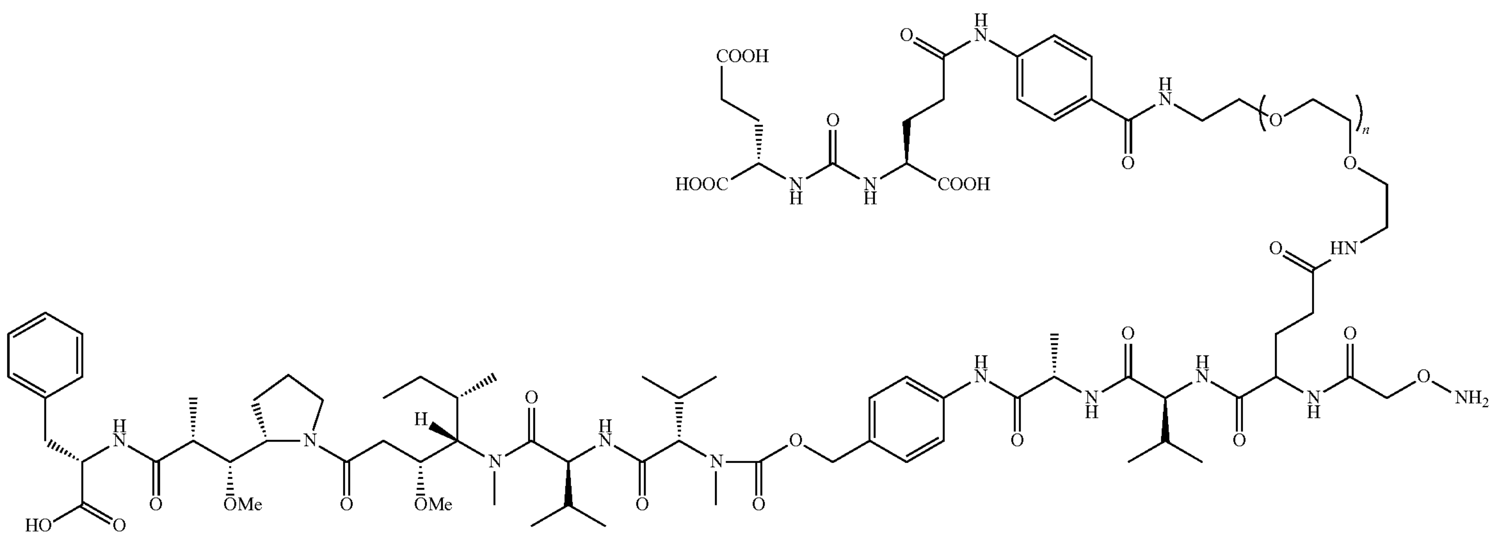 |

TABLE 3-continued

Ligands-Toxins

| Example | Structure |
|---|---|
| 7 | 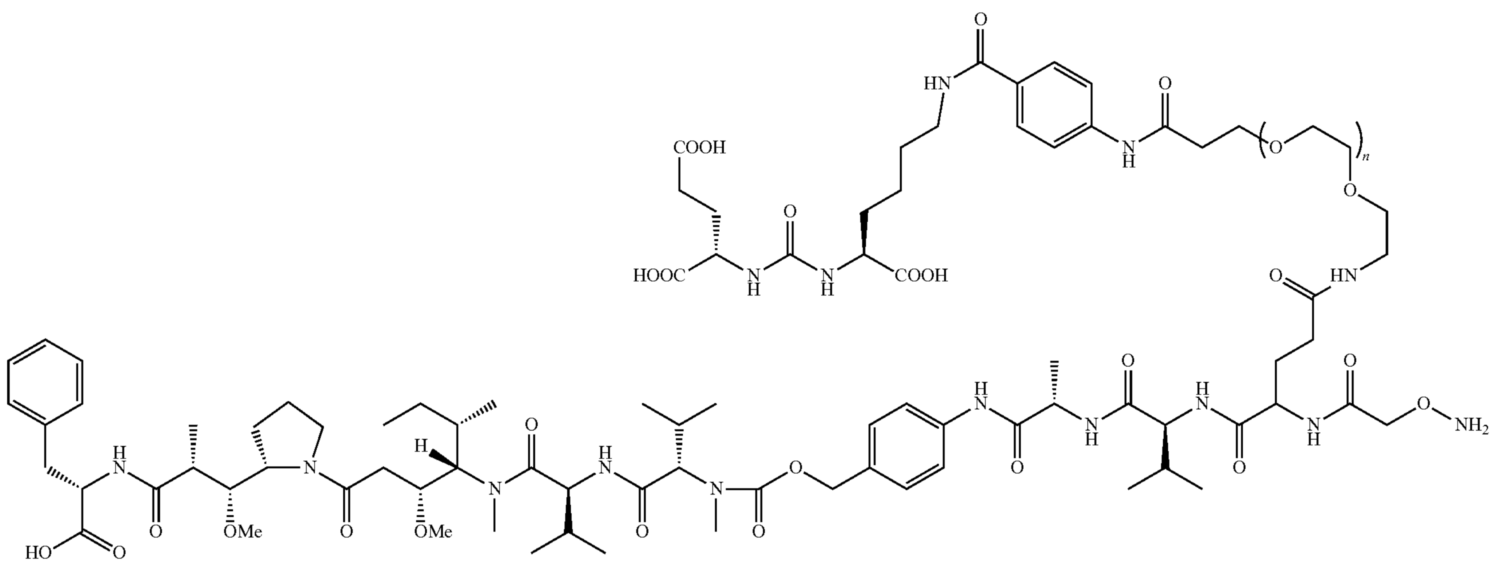 |

TABLE 3-continued

Ligands-Toxins

| Example | Structure |
|---|---|
| 8 | (chemical structure) |

TABLE 3-continued
Ligands-Toxins
| Example | Structure |
|---|---|
| 9 | 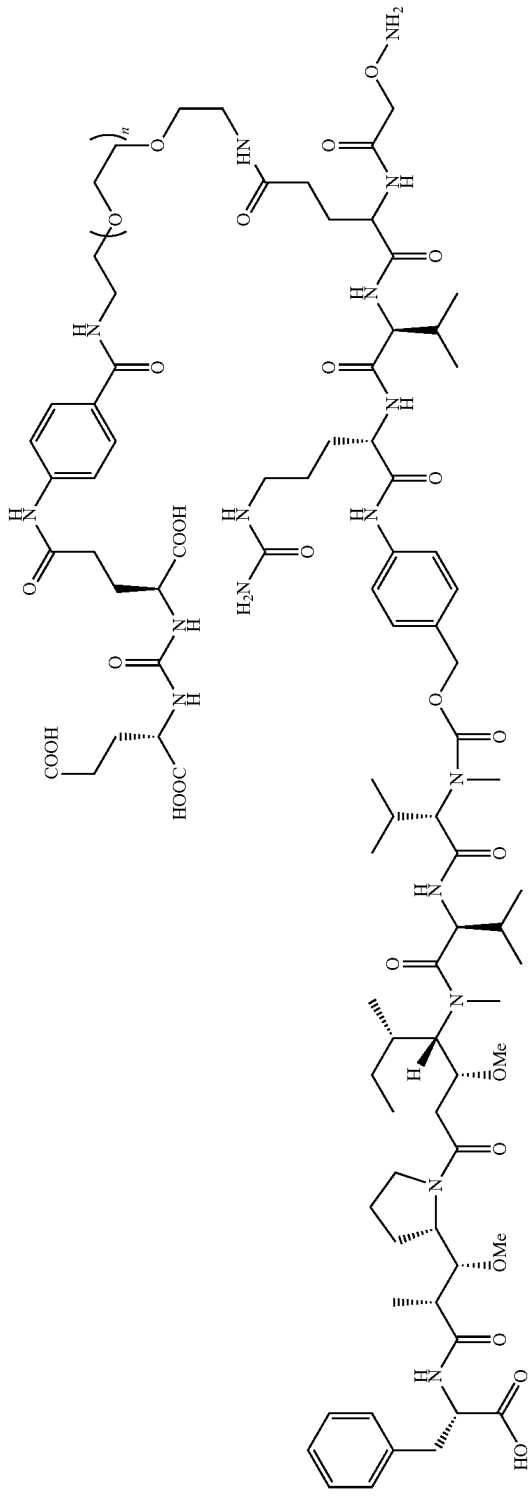 |

TABLE 3-continued
Ligands-Toxins
| Example | Structure |
|---|---|
| 10 | 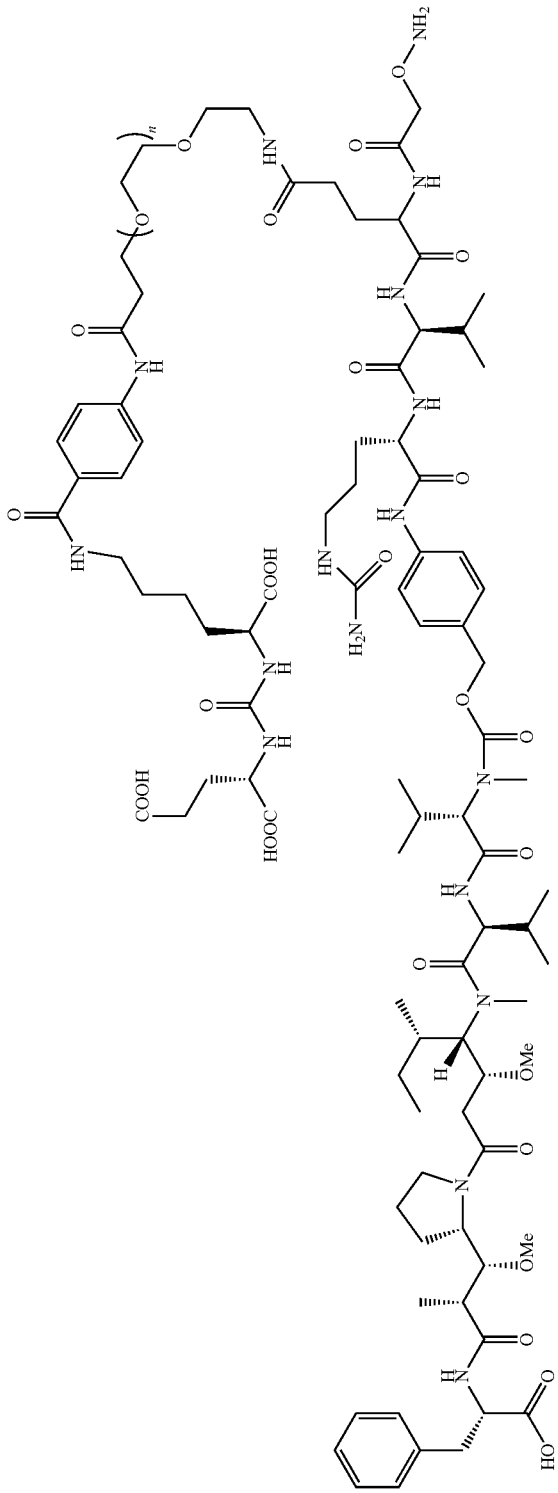 |

TABLE 3-continued
Ligands-Toxins
| Example | Structure |
|---|---|
| 11 | 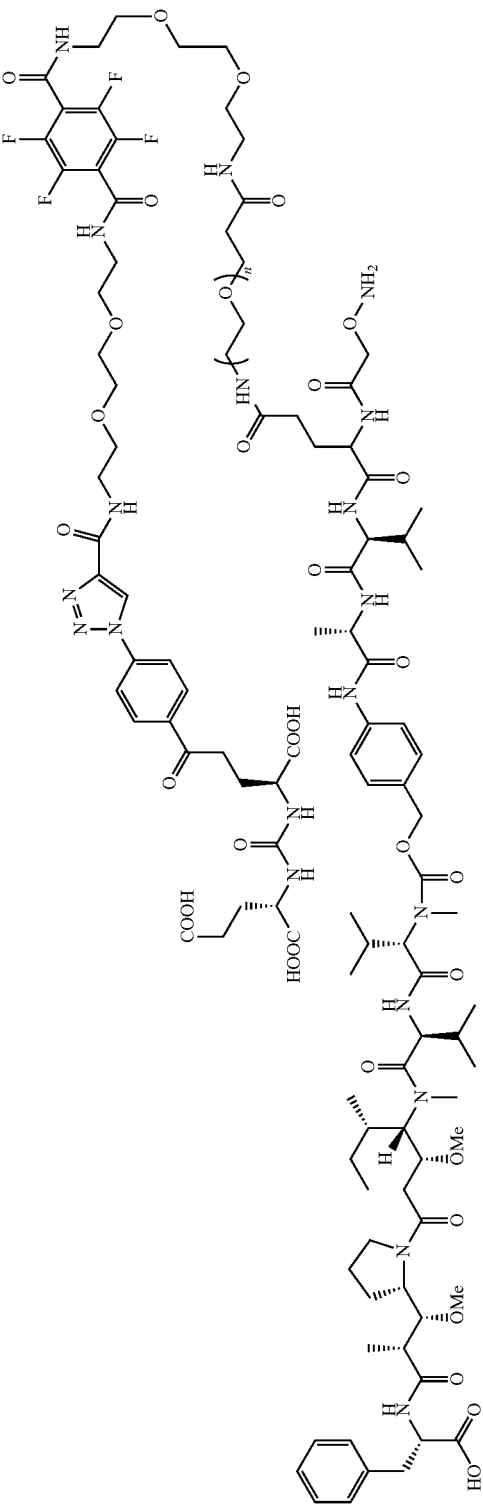 |

TABLE 3-continued
Ligands-Toxins
| Example | Structure |
|---|---|
| 12 | 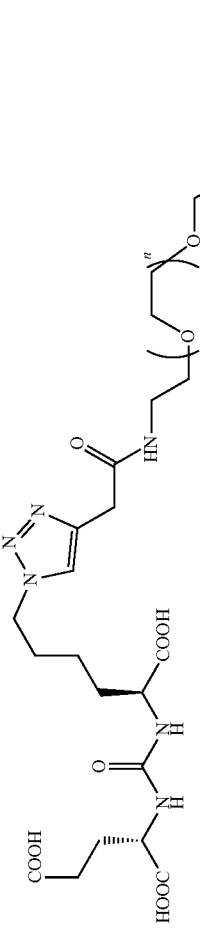 |

TABLE 3-continued
Ligands-Toxins
| Example | Structure |
|---|---|
| 13 | 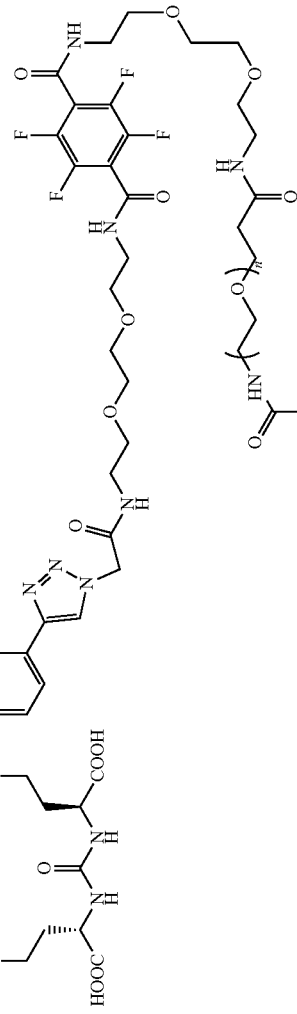 |

TABLE 3-continued
Ligands-Toxins
| Example | Structure |
|---|---|
| 14 | 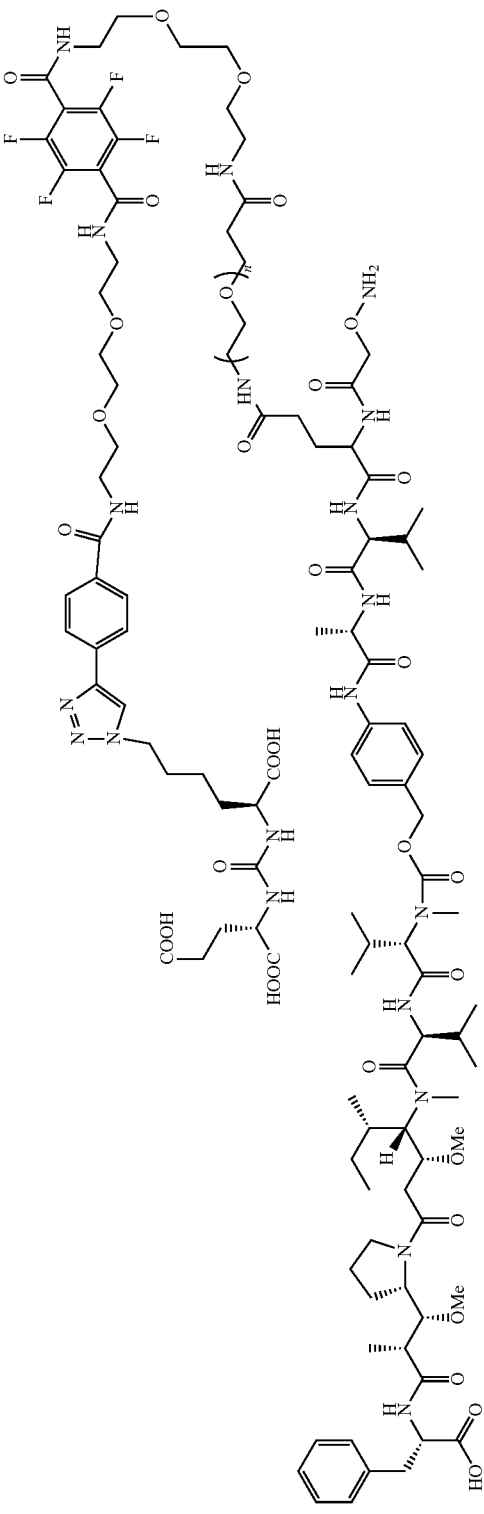 |
| 15 | 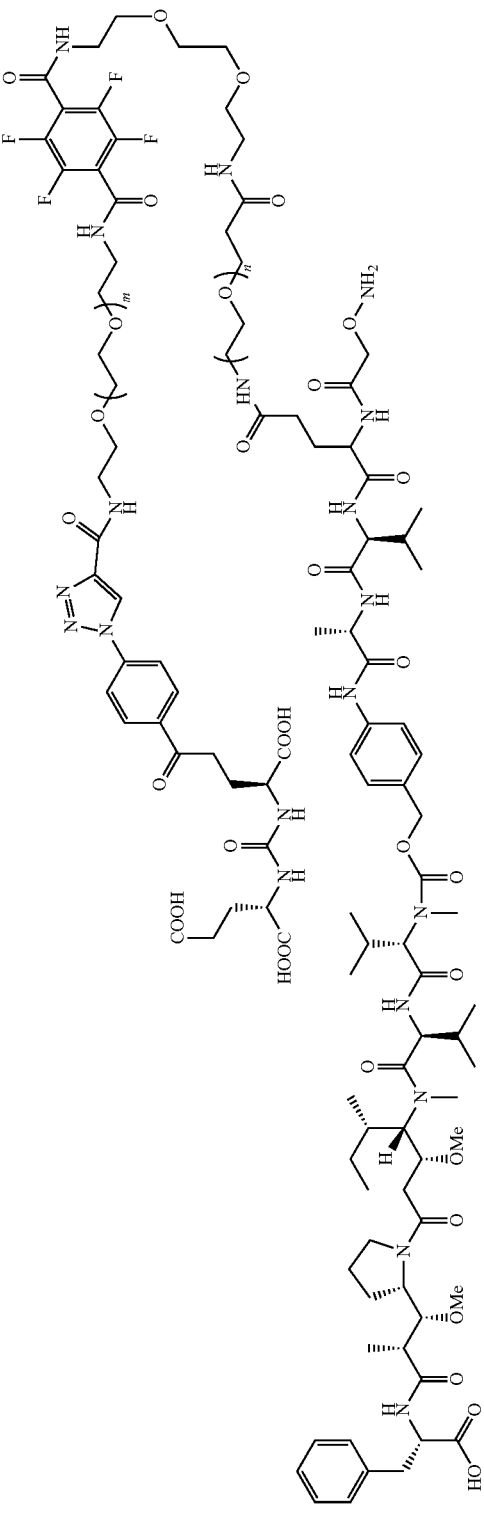 |

TABLE 3-continued
Ligands-Toxins
| Example | Structure |
|---|---|
| 16 | 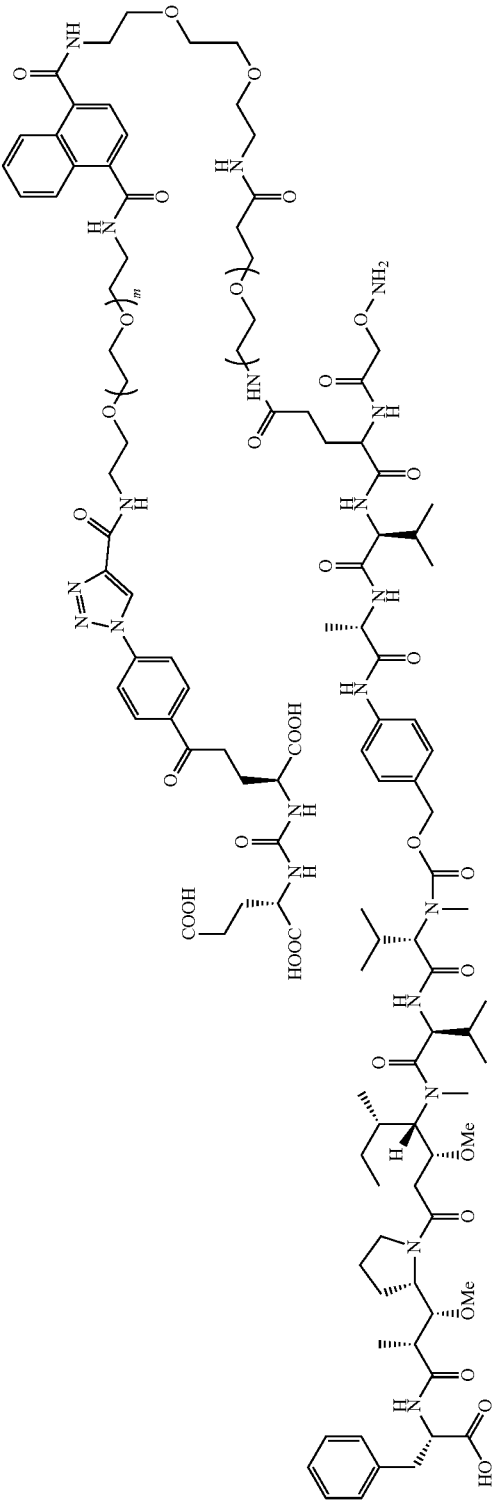 |

TABLE 3-continued
Ligands-Toxins
| Example | Structure |
|---|---|
| 17 | 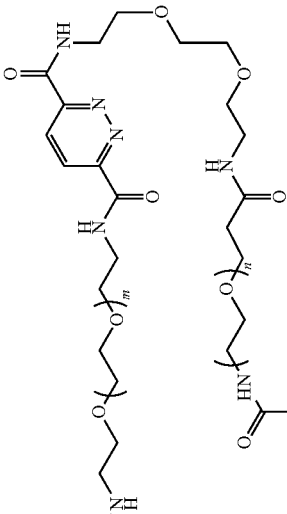 |

TABLE 3-continued
Ligands-Toxins
| Example | Structure |
|---|---|
| 18 | 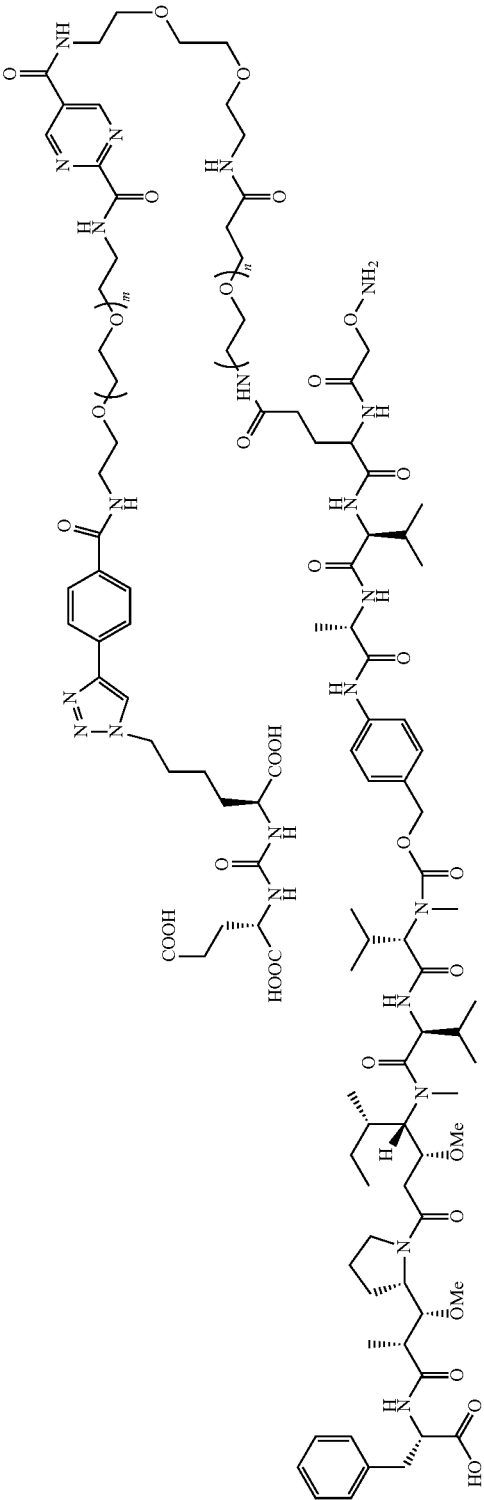 |
| 19 | 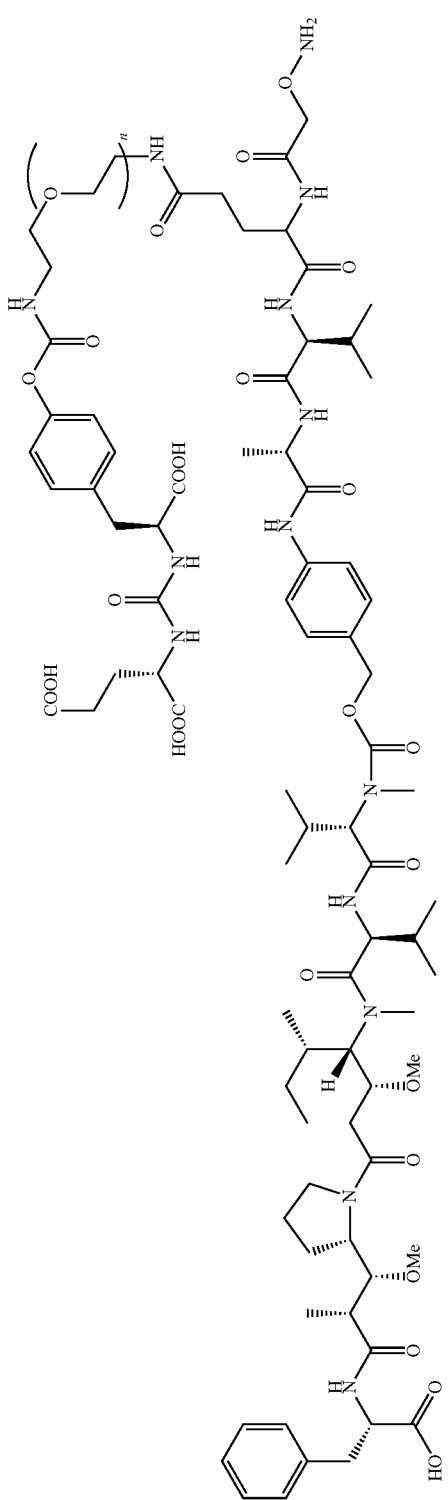 |

TABLE 3-continued
Ligands-Toxins
| Example | Structure |
|---|---|
| 20 | 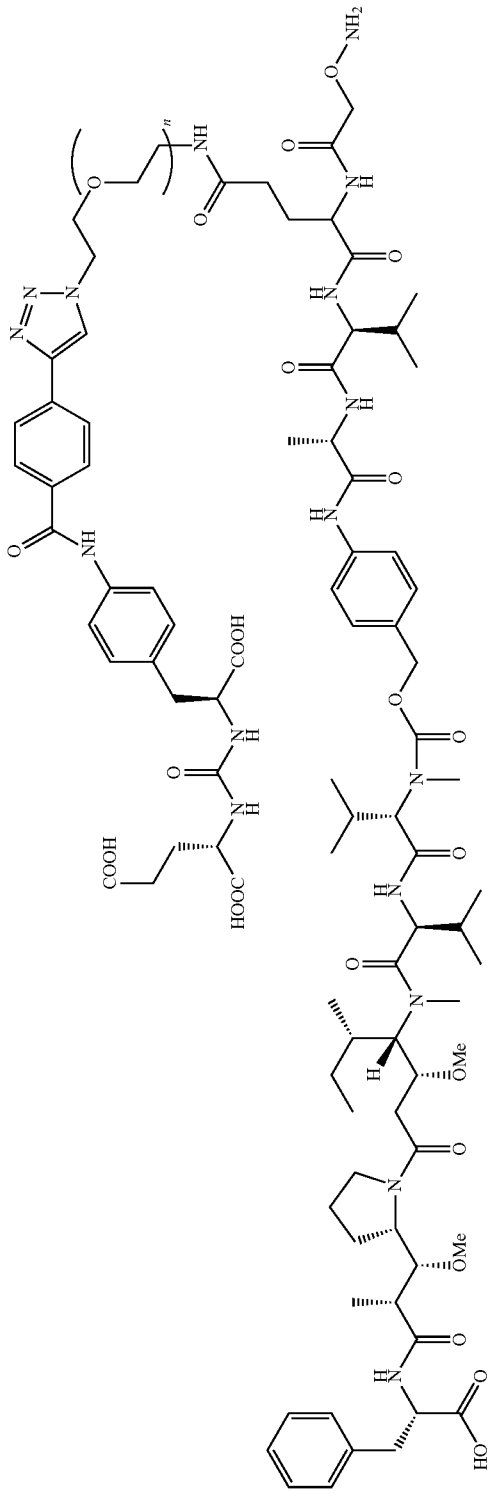 |
| 21 | 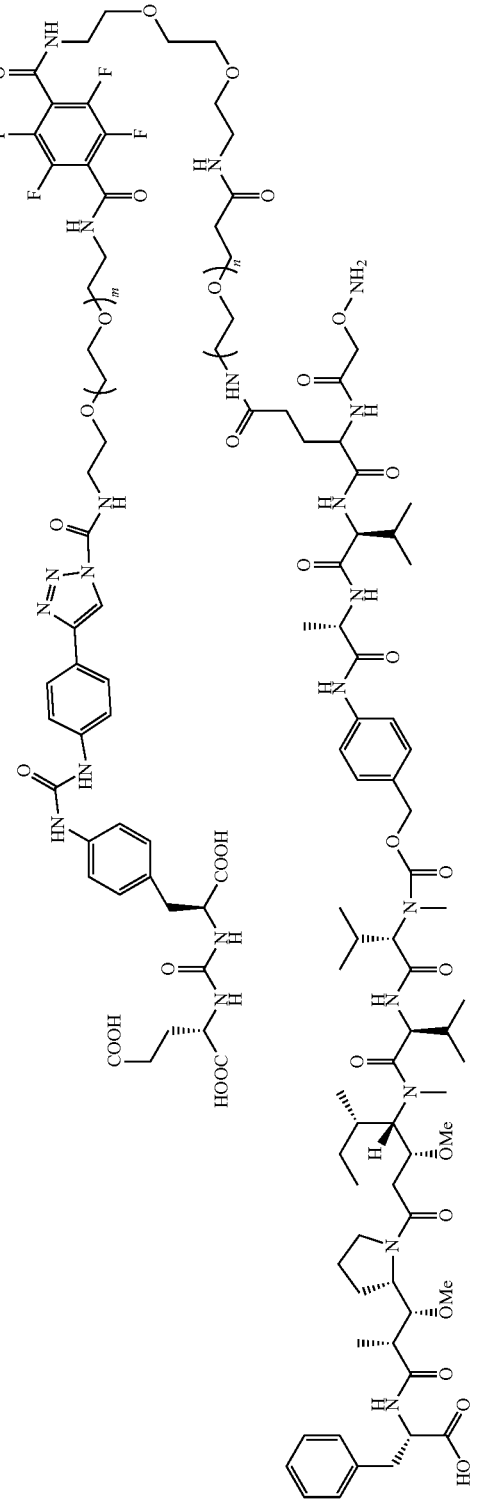 |

TABLE 3-continued
Ligands-Toxins
| Example | Structure |
|---|---|
| 22 | 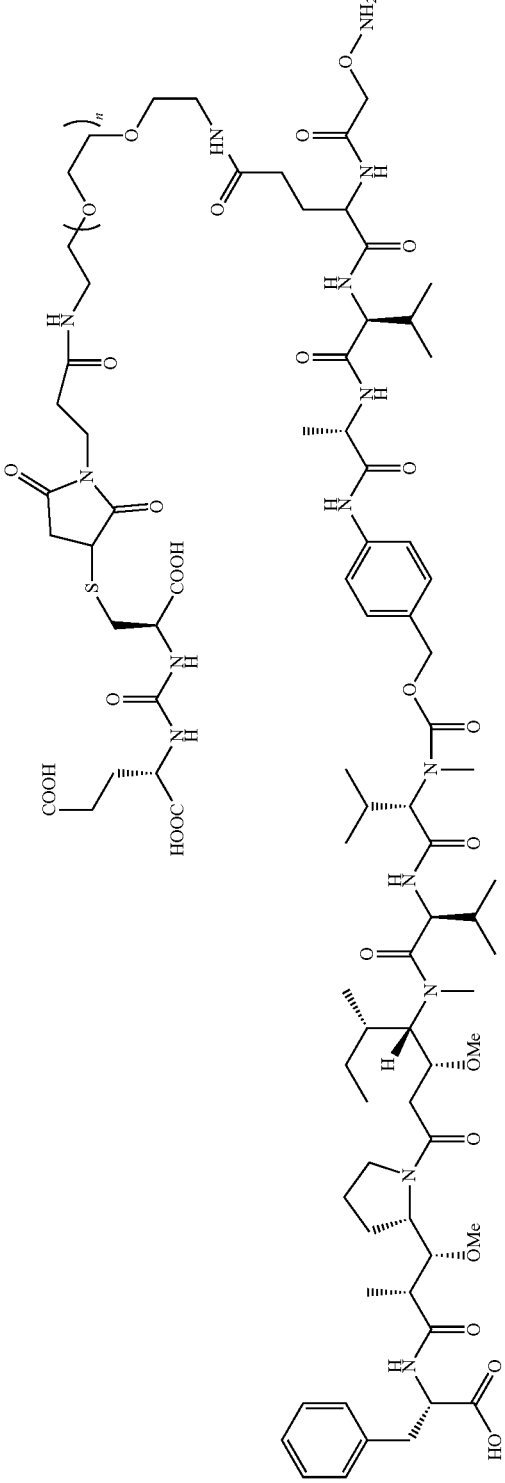 |
| 23 | 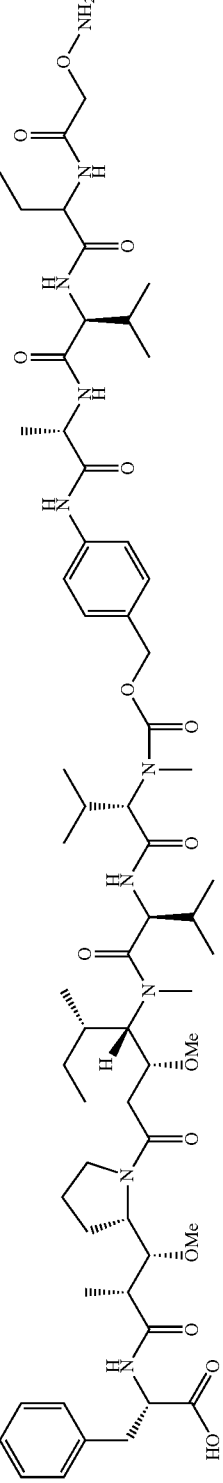 |

TABLE 3-continued
Ligands-Toxins
| Example | Structure |
|---|---|
| 24 | 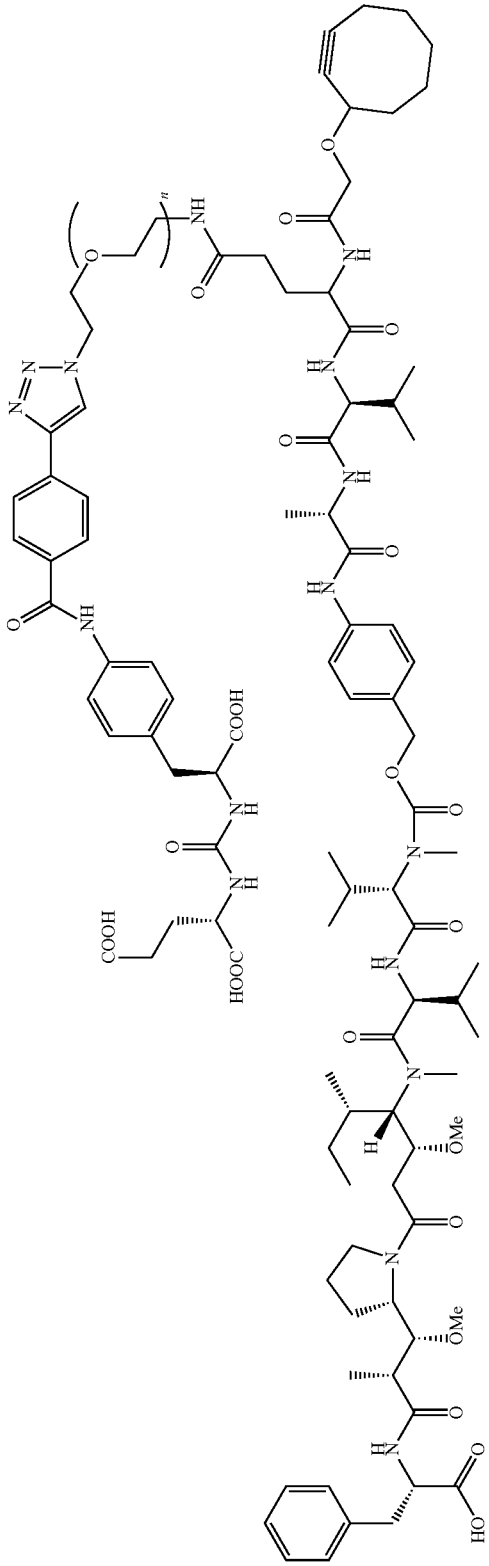 |
| 25 | 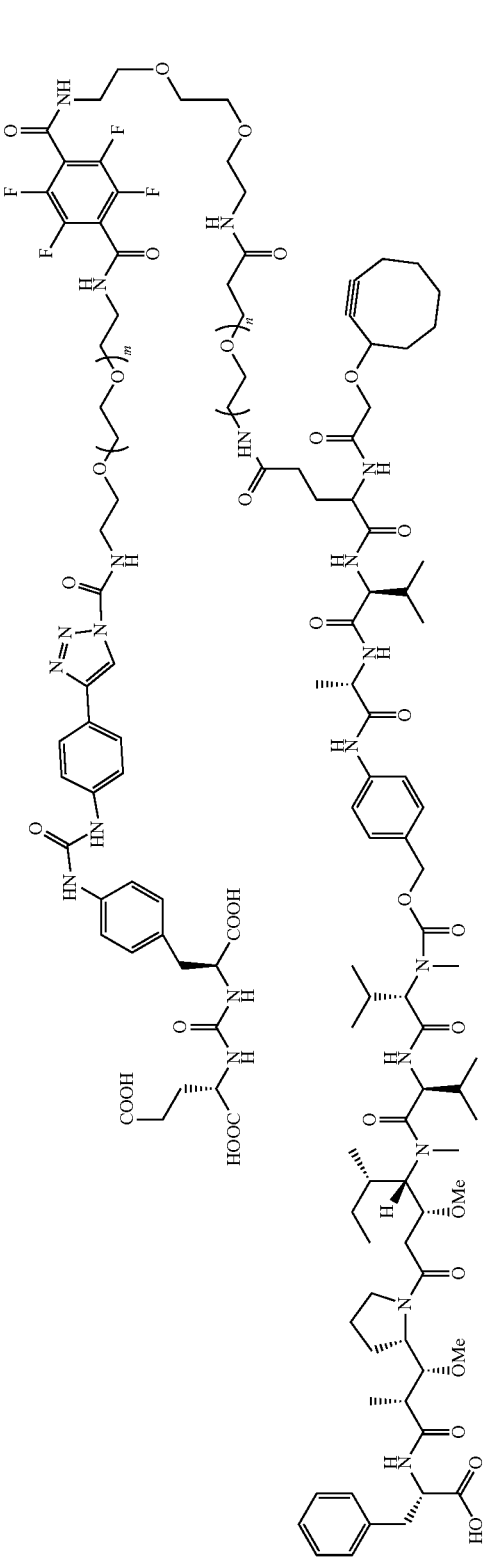 |

TABLE 3-continued
Ligands-Toxins
| Example | Structure |
|---|---|
| 26 | 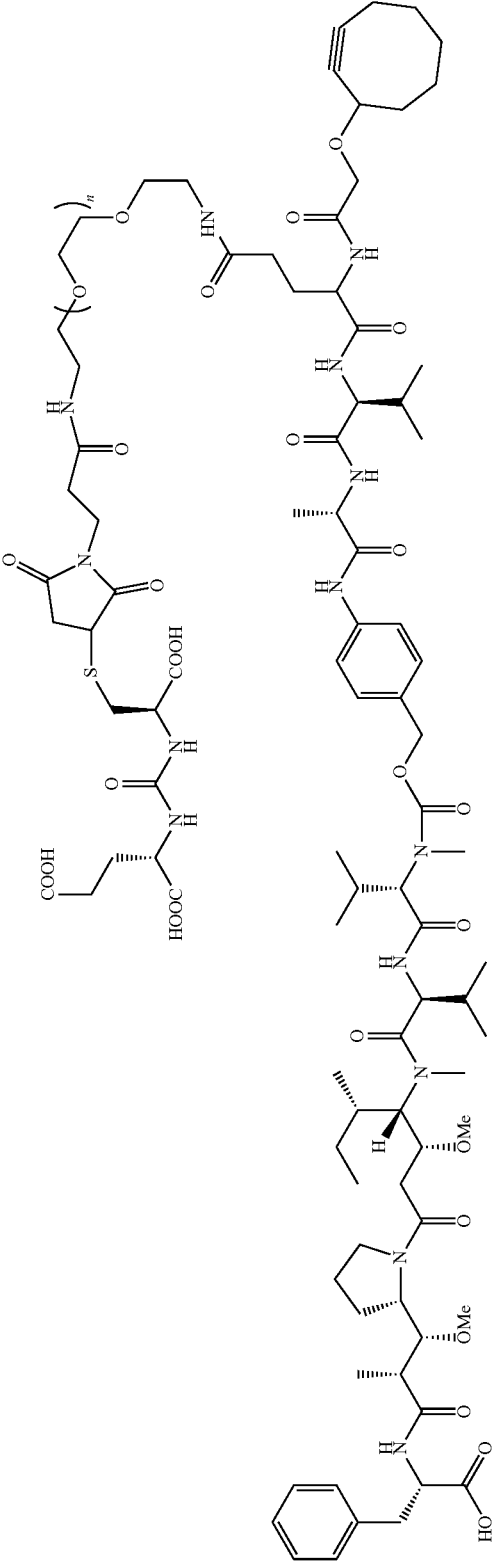 |

TABLE 3-continued
Ligands-Toxins
| Example | Structure |
|---|---|
| 27 | 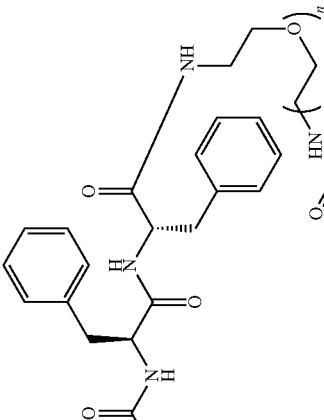 |

TABLE 3-continued
Ligands-Toxins
| Example | Structure |
|---|---|
| 28 | 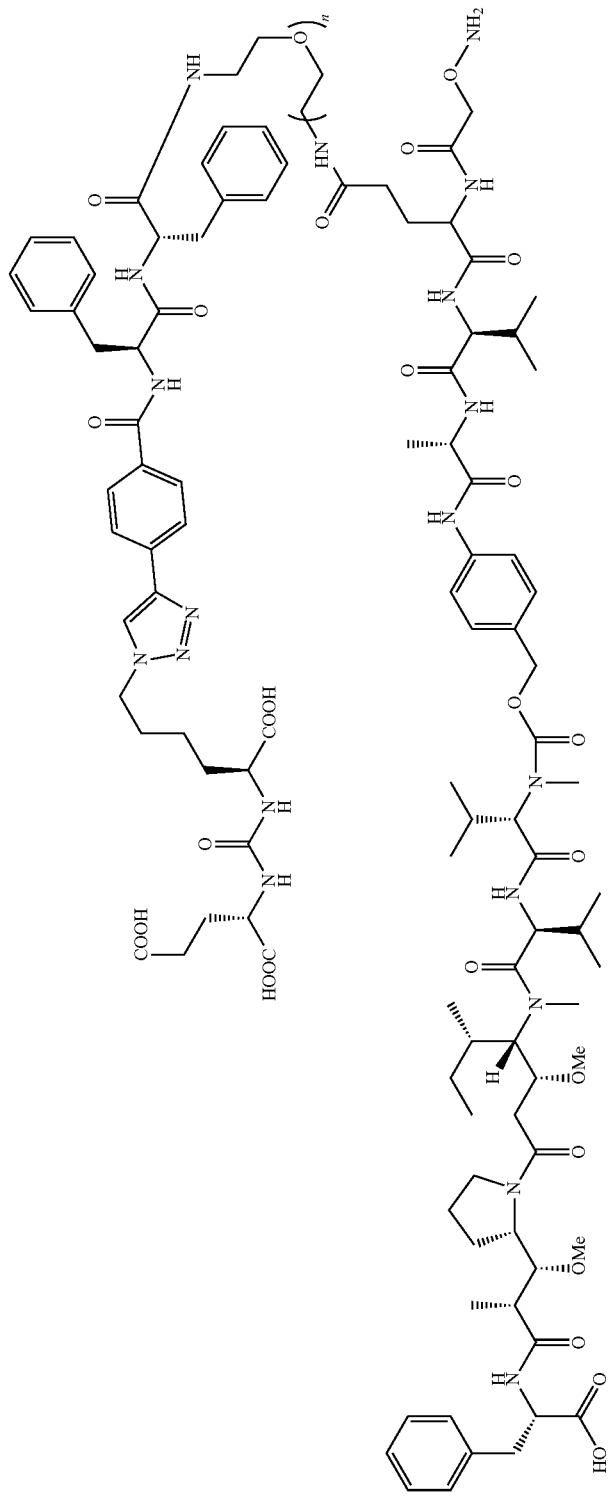 |

TABLE 3-continued

Ligands-Toxins

| Example | Structure |
|---|---|
| 29 | (chemical structure) |

TABLE 3-continued
Ligands-Toxins
| Example | Structure |
|---|---|
| 30 | 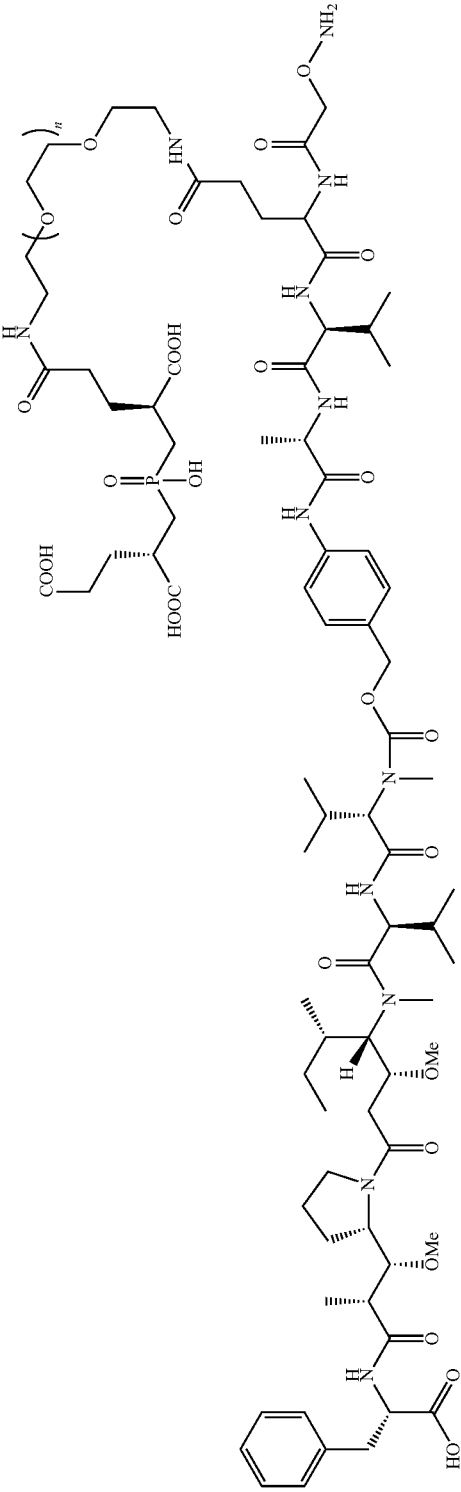 |

TABLE 3-continued
Ligands-Toxins
| Example | Structure |
|---|---|
| 31 | 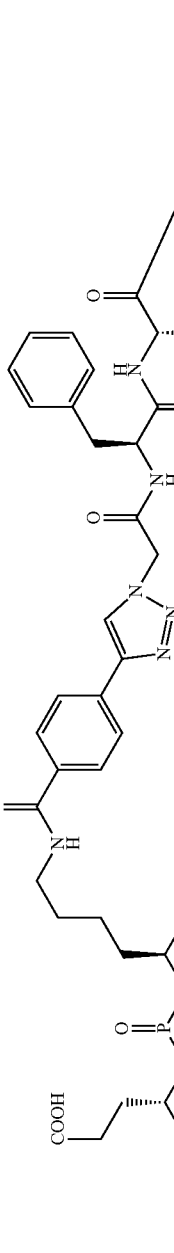 |

TABLE 3-continued
Ligands-Toxins
| Example | Structure |
|---|---|
| 32 | 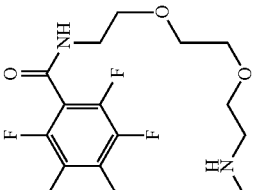 |

TABLE 3-continued
Ligands-Toxins
| Example | Structure |
|---|---|
| 33 | 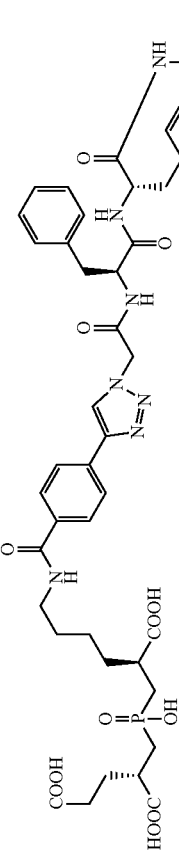 |

TABLE 3-continued
Ligands-Toxins
| Example | Structure |
|---|---|
| 34 | 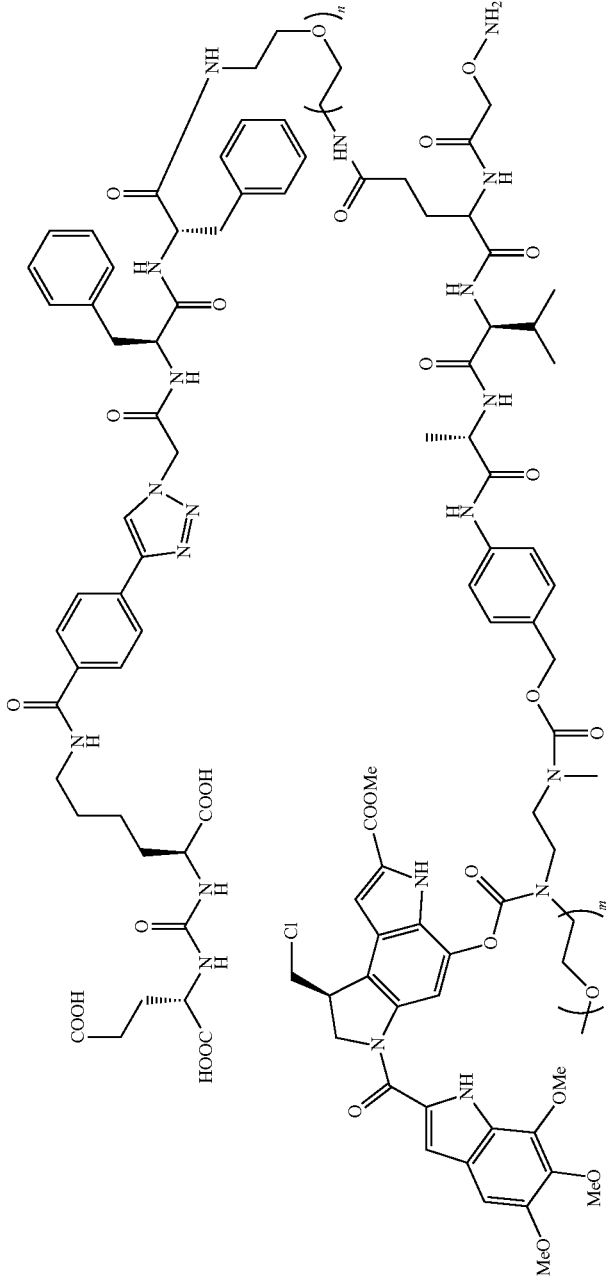 |

TABLE 3-continued
Ligands-Toxins
| Example | Structure |
|---|---|
| 35 | 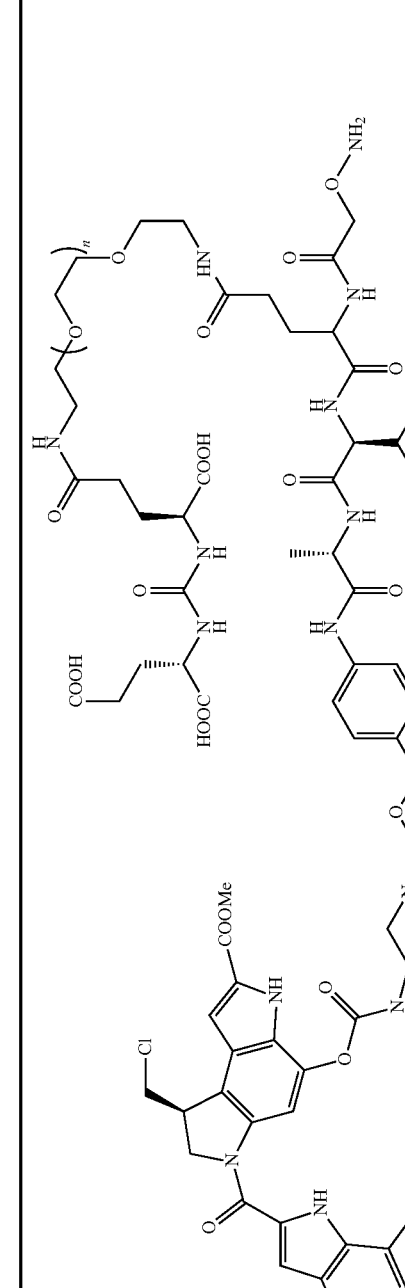 |

TABLE 3-continued

Ligands-Toxins

| Example | Structure |
|---|---|
| 36 | (chemical structure) |

TABLE 3-continued

Ligands-Toxins

| Example | Structure |
|---|---|
| 37 | 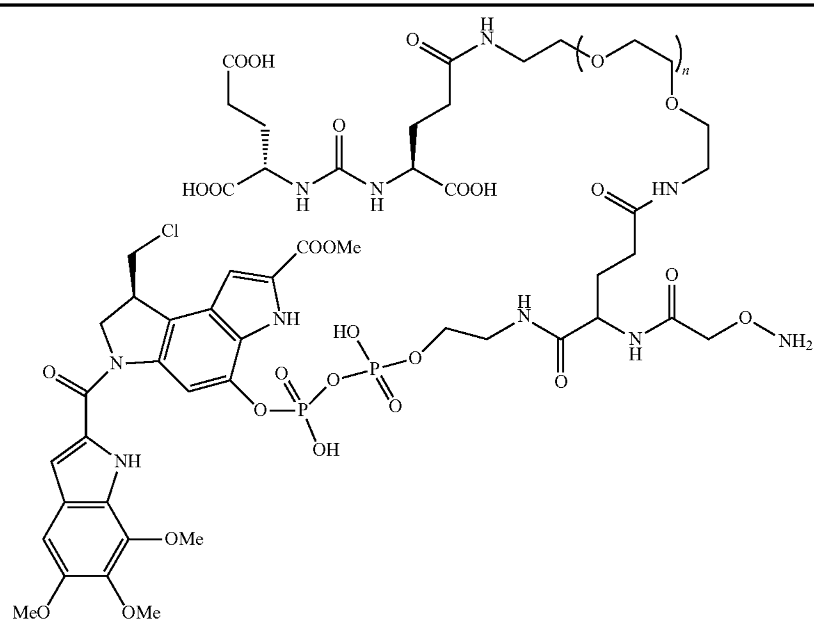 |

TABLE 3-continued
Ligands-Toxins
| Example | Structure |
|---|---|
| 38 | 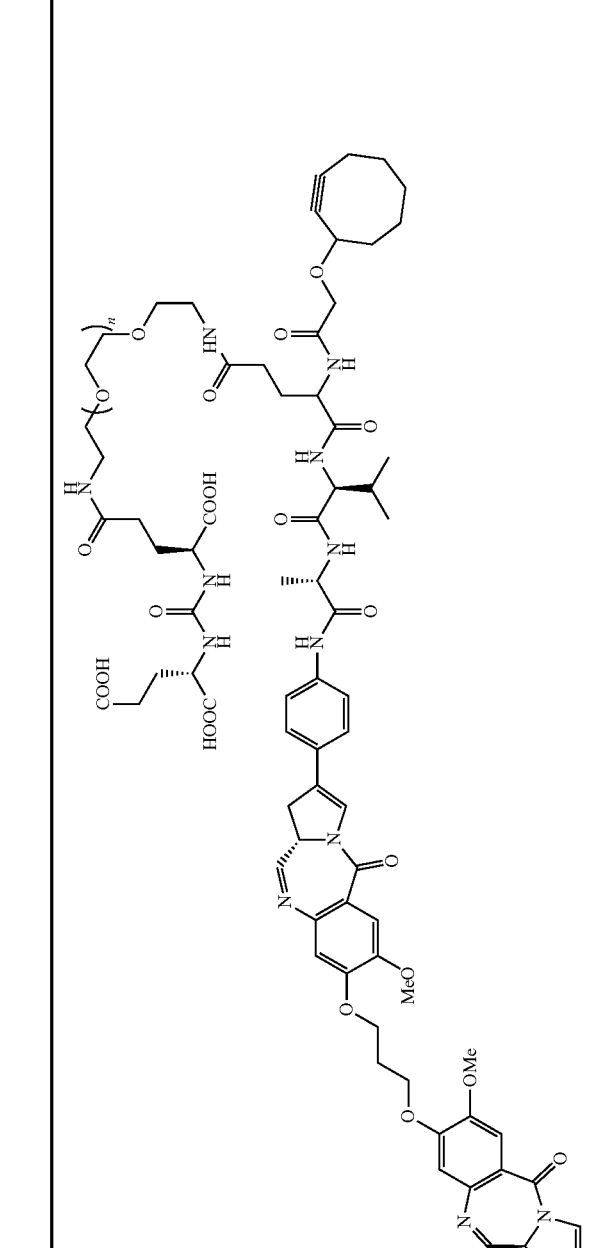 |

In some aspects of the invention disclosure anti-PSMA antibody, variant or drug conjugate with increase serum half-life, water solubility, bioavailability, therapeutic half-life, or circulation time, or to modulate immunogenicity, or biological activity is desired. One method of achieving such desired features of the anti-PSMA composition disclosed herein, is by covalent attachment of the polymer poly ethylene glycol, (PEG). To maximize the desired properties of poly ethylene glycol, the total molecular weight and hydration state of the polymer or polymers attached to the biologically active molecule must be sufficiently high to impart the advantageous characteristics typically associated with such polymer attachment, such as increased water solubility and circulating half-life, while not adversely impacting the bioactivity of the molecule to which the poly ethylene glycol is attached.

Poly ethylene glycol derivatives are frequently linked to biologically active molecules through reactive chemical functionalities, such as amino acid residues, the N-terminus, and/or carbohydrate moieties. WO99/67291 discloses a process for conjugating a protein with poly ethylene glycol, wherein at least one amino acid residue on the protein is substituted with a synthetic amino acid and the protein is contacted with poly ethylene glycol under conditions sufficient to achieve conjugation to the protein.

Proteins and other molecules often have a limited number of reactive sites available for polymer attachment. The sites most suitable for modification via polymer attachment may play a significant role in receptor binding, and such sites may be necessary for retention of the biological activity of the molecule therefore making them inappropriate for polymer attachment. As a result, indiscriminate attachment of polymer chains to such reactive sites on a biologically active molecule often leads to a significant reduction or even total loss of biological activity of the polymer-modified molecule, poly ethylene glycol attachment can be directed to a particular position within a protein such that the poly ethylene glycol moiety does not interfere with the function of that protein. One method of directing poly ethylene glycol attachment is to introduce a synthetic amino acid into the protein sequence. The protein biosynthetic machinery of the prokaryote *Escherichia coli* (*E. coli*) can be altered in order to incorporate synthetic amino acids efficiently and with high fidelity into proteins in response to the amber codon, UAG. See, e.g., J. W. Chin et aL, J. Amer. Chem. Soc. 124: 9026-9027, 2002; J. W. Chin, & P. G. Schultz, ChemBioChem 3(11):1135-1137, 2002; J. W. Chin, et al., PNAS USA 99:11020-11024, 2002; and, L. Wang, & P. G. Schultz, Chem. Comm., 1: 1-11, 2002. A similar method can be accomplished with the eukaryote, *Saccharomyces cerevisiae* (*S. cerevisiae*) (e.g., J. Chin et al., Science 301: 964-7, 2003). Using this method, a non-naturally encoded amino acid can be incorporated into anti-PSMA antibody, variant or drug conjugate of the present invention, providing an attachment site for poly ethylene glycol. See, for example WO2010/011735 and WO2005/074650.

Pharmaceutical Compositions

In other aspects of the present invention the PSMA antibody variants or PSMA antibody drug conjugates further comprise a pharmaceutical composition or formulation. Such a pharmaceutical composition can employ various pharmaceutically acceptable excipients, stabilizers, buffers, and other components for administration to animals. See, for example, Remington, *The Science and Practice of Pharmacy*, 19th ed., Gennaro, ed., Mack Publishing Co., Easton, PA, 1995. Identifying suitable composition or formulations for stability, administration to a subject, and activity varies with each compound as a number of components, (for example, purifying, stabilizing components), need to be considered. Suitable salts for inclusion into the composition or formulation can include, but not limited to, sodium chloride, potassium chloride or calcium chloride. Buffering and/or stabilizing agents such as sodium acetate can be used. Suitable buffers can include phosphate-citrate buffer, phosphate buffer, citrate buffer, L-histidine, L-arginine hydrochloride, bicarbonate buffer, succinate buffer, citrate buffer, and TRIS buffer, either alone or in combination. Surfactants can also be employed, including polysorbates (e.g., polysorbate 80), dodecyl sulfate (SDS), lecithin either alone or in combination.

In some aspects of the present invention, the pharmaceutical composition or formulation can be an aqueous composition or in the form of a reconstituted liquid composition or as a powder. The composition or formulation can have a pH range from about 4.0 to about 7.0 or from about 4.5 to about 6.5 when the formulation is in a liquid form. However, the pH can be adjusted to provide acceptable stability and administration by the skilled medical practitioner.

The composition can further stored in a vial or cartridge, a pen delivery device, a syringe, intravenous administration tubing or an intravenous administration bag but is not limited to such. In other embodiments a pharmaceutical composition of the invention can be administered as a single dose or followed by one or more subsequent dose(s) minutes, days, or weeks after the first dose. Further administrations may be contemplated as needed to treat, reduce or prevent a cancer, including prostate cancer.

In some instances, the PSMA antibodies, variants or anti-PSMA ADC compositions of the present invention disclosure may be used in conjunction with an additional therapy or treatment including but not limited to surgery, radiation, cryosurgery, thermotherapy, hormone treatment, chemotherapy, vaccines and other immunotherapies. In some embodiments such additional treatment can include a therapeutic agent such as chemotherapeutic agent, hormonal agent, antitumor agent, immunostimulatory agent, immunomodulator, corticosteroid or combination thereof. In one embodiment, the hormonal agent is enzalutamide.

In other embodiments the anti-PSMA ADCs of the invention can be administered with one or more immunostimulatory agents to induce or enhance an immune response. Immunostimulatory agents that can stimulate specific arms of the immune system, such as natural killer (NK) cells that mediate antibody-dependent cell cytotoxicity (ADCC). Such immunostimulatory agents include, but are not limited to, IL-2, immunostimulatory oligonucleotides (for example, CpG motifs), α-interferon, γ-interferon, tumor necrosis factor alpha (TNFα). In other embodiments the anti-PSMA ADCs of the invention can be administered with one or more immunomodulators including, but not limited to, cytokines, chemokines (including, but are not limited to, SLC5 ELC, MIP3α, MIP3β, IP-IO, MIG, and combinations thereof). Other therapeutic agents can be a vaccine that immunizes a subject against PSMA. Such vaccines, in some embodiments, include antigens, such as PSMA dimers, with, optionally, one or more adjuvants to induce or enhance an immune response. Adjuvants of many kinds are well known in the art.

The chemotherapeutic agent or any agent involved in treating, reducing or preventing a disease, condition or cancer in a subject in need thereof can also be administered in combination with and anti-PSMA ADC of the invention disclosure. Chemotherapeutic agents may include, but are not limited to, erlotinib (TARCEVA®, Genentech/OSI Pharm.), bortezomib (VELCADE®, Millennium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNEV, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; antifolate antineoplastic such as pemetrexed (ALIMTA®, Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gammaI1 and calicheamicin omegaI1; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; antiandrogens (for example, enzalutamide) or androgen deprivation therapy; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

The term "about" will be understood by persons of ordinary skill in the art and will vary to some extent depending on the context in which it is used.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example 1

Transient Transfection. CHO—S culture were seeded at $0.75 \times 10^6$/mL approximately 16 hours pre-transfection in FreeStyle CHO medium. Cells were transfected the following day when the cell count reached $1.4$-$1.6 \times 10^6$/mL. At the target cell count, 400 mM para-acetyl phenylalanine (pAF) stock was added to a 1.4 mM final culture concentration.

Polyethylenimine/DNA (PEI/DNA) complex was prepared as described: DNA (1.42 ug/$1 \times 10^6$ cells) was dissolved in RPMI media (5% (v/v) of total culture volume), DNA/RPMI mixture was incubated at room temperature for 2 minutes, PEI stock (1 mg/mL) was added to DNA solution at a 3:1 ratio (PEI/DNA (ug/ug)), and the mixture incubated at room temperature for 5 min.

The mixture was gently added to the cell culture and swirled. The flasks were transferred to a 32° C. incubator. At day 6 post-transfection, a western blot analysis was performed. At day 7 post-transfection, the supernatant was harvested.

Example 2

Antibody Humanization—Parental mouse J591 (Liu et al., Cancer Research, 57, 3629-36354, 1997) antibody was humanized by selecting human frameworks based on sequence identity with the mouse framework sequence. The light chain and heavy chain CDRs from the mouse antibody were grafted onto the human frameworks, respectively, and analyzed for binding to PSMA antigen. Humanized variants were generated by pairing four human heavy chain frameworks with six light chain frameworks. The variants were expressed transiently in HEK293 cells and the supernatants were tested for binding to the PSMA antigen expressed in LnCap cells by FACS. Table 4 describes a selected heavy chain variable region sequence and 4 light chain variable region sequences used for further studies. Binding analysis showed four humanized full length variants, shown as humanized anti-PSMA variant 1, 2, 3 and 4 (Table 4), retained comparable binding affinity as the chimera, (Table 4), exhibiting nanomolar range binding affinity. As disclosed in Table 4, humanized anti-PSMA variant 1 comprise the heavy chain sequence of SEQ. ID Nos: 8 and the light chain sequence of SEQ. ID Nos: 9; humanized anti-PSMA variant 2 comprise the heavy chain sequence of SEQ. ID Nos: 10 and the light chain sequence of SEQ. ID Nos: 11; humanized anti-PSMA variant 3 comprise the heavy chain sequence of SEQ. ID Nos: 12 and the light chain sequence of SEQ. ID Nos: 13; and humanized anti-PSMA variant 4 comprise the heavy chain sequence of SEQ. ID Nos: 14 and the light chain sequence of SEQ. ID Nos: 15.

TABLE 4

Anti-PSMA Antibody Variants Amino Acid Sequences
Sequences of humanized and chimeric anti-PSMA
antibodies Humanized Heavy Chain Variable Region Sequence SEQ ID NO: 1
QVQLVQSGAEVKKPGASVKVSCKASGYTFTEYTIHWVRQAPGQRLEWMGNI
NPNNGGTTYNQKFEDRVTITRDTSASTAYMELSSLRSEDTAVYYCAAGWNF
DYWGQGTTLTVSS Humanized Light Chain Variable Region Sequence SEQ ID NO: 2
DIQLTQSPSFLSASVGDRVTITCKASQDVGTAVDWYQQKPGKAPKLLIYWA
STRHTGVPSRFSGSGSGTEFTLTISSLQPEDFATYYCQQYNSYPLTFGGGT
KVEIKRTV SEQ ID NO: 3
DIQLTQSPSFLSASVGDRVTITCKASQDVGTAVDWYQQKPGKAPKLLIYWA
STRHTGVPDRFSGSGSGTEFTLTISSLQPEDFATYYCQQYNSYPLTFGGGT
KVEIKRTV SEQ ID NO: 4
DIQLTQSPSFLSASVGDRVTITCKASQDVGTAVDWYQQKPGKAPKLLIYWA
STRHTGVPSRFSGSGSGTEFTLTISSLQSEDFATYYCQQYNSYPLTFGGGT
KVEIKRTV SEQ ID NO: 5
DIQLTQSPSFLSASVGDRVTITCKASQDVGTAVDWYQQKPGKAPKLLIYWA
STRHTGVPSRFSGSGSGTEFTLTISNLQPEDFATYYCQQYNSYPLTFGGGT
KVEIKRTV Chimeric Heavy Chain Variable Region Sequence SEQ ID NO: 6
EVQLQQSGPELVKPGTSVRISCKTSGYTFTEYTIHWVKQSHGKSLEWIGNI
NPNNGGTTYNQKFEDKATLTVDKSSSTAYMELRSLTSEDSAVYYCAAGWNF
DYWGQGTTLTVSS Chimeric Light Chain Variable Region Sequence SEQ ID NO: 7
DIVMTQSHKFMSTSVGDRVSIICKASQDVGTAVDWYQQKPGQSPKLLIYWA
STRHTGVPDRFTGSGSGTDFTLTITNVQSEDLADYFCQQYNSYPLTFGAGT
KVEIKRTV Humanized Anti-PSMA (full length) Variant 1

SEQ ID NO: 8
Heavy Chain
QVQLVQSGAEVKKPGASVKVSCKASGYTFTEYTIHWVRQAPGQRLEWMGNI
NPNNGGTTYNQKFEDRVTITRDTSASTAYMELSSLRSEDTAVYYCAAGWNF
DYWGQGTTLTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTP
EVTCVVVDVSHEDPEVKFNWYVDGVEHNAKTKPREEQYNSTYRVVSVLTV
LHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 9
Light Chain
DIQLTQSPSELSASVGDRVTTTCKASQDVGTAVDWYQQKPGKAPKLLIYWA
STRHTGVPSRFSGSGSGTEFTLTISSLQPEDFATYYCQQYNSYPLTFGGGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC Humanized Anti-PSMA (full length) Variant 2

SEQ ID NO: 10
Heavy Chain
QVQLVQSGAEVKKPGASVKVSCKASGYTFTEYTIHWVRQAPGQRLEWMGNI
NPNNGGTTYNQKFEDRVTITRDTSASTAYMELSSLRSEDTAVYYCAAGWNF
DYWGQGTTLTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 11
Light Chain
DIQLTQSPSFLSASVGDRVTITCKASQDVGTAVDWYQQKPGKAPKLLIYWA
STRHTGVPSRFSGSGSGTEFTLTISSLQSEDFATYYCQQYNSYPLTFGGGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC Humanized Anti-PSMA (full length) Variant 3

SEQ ID NO: 12
Heavy Chain
QVQLVQSGAEVKKPGASVKVSCKASGYTFTEYTIHWVRQAPGQRLEWMGNI
NPNNGGTTYNQKFEDRVTITRDTSASTAYMELSSLRSEDTAVYYCAAGWNF
DYWGQGTTLTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 13
Light Chain
DIQLTQSPSFLSASVGDRVTITCKASQDVGTAVDWYQQKPGKAPKLLIYWA
STRHTGVPDRFSGSGSGTEFTLTISSLQPEDFATYYCQQYNSYPLTFGGGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC Humanized Anti-PSMA (full length) Variant 4

SEQ ID NO: 14
Heavy Chain
QVQLVQSGAEVKKPGASVKVSCKASGYTFTEYTIHWVRQAPGQRLEWMGNI
NPNNGGTTYNQKFEDRVTITRDTSASTAYMELSSLRSEDTAVYYCAAGWNF
DYWGQGTTLTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 15
Light Chain
DIQLTQSPSFLSASVGDRVTITCKASQDVGTAVDWYQQKPGKAPKLLIYWA
STRHTGVPSRFSGSGSGTEFTLTISNLQPEDFATYYCQQYNSYPLTFGGGT
KVEIKRTVAAPSVFIFPPSDEQLKSGTASVVCLLNNFYPREAKVQWKVDNA TABLE 4-continued Anti-PSMA Antibody Variants Amino Acid Sequences
Sequences of humanized and chimeric anti-PSMA
antibodies

LQSGNSQESVTEQDSKDSTYSLSSTLTLSKADYEKHKVYACEVTHQGLSSP
VTKSFNRGEC

Chimeric Anti-PSMA Antibody (full length) Variant

SEQ ID NO: 16
Heavy Chain
EVQLQQSGPELVKPGTSVRISCKTSGYTFTEYTIHWVKQSHGKSLEWIGNI
NPNNGGTTYNQKFEDKATLTVDKSSSTAYMELRSLTSEDSAVYYCAAGWNF
DYWGQGTTLTVSSASTKGPSVFPLAPSSKSTSGGTAALGCLVKDYFPEPVT
VSWNSGALTSGVHTFPAVLQSSGLYSLSSVVTVPSSSLGTQTYICNVNHKP
SNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKL
TVDKSRWQQGNVFSCSVMHEALHNHYTQKSLSLSPG SEQ ID NO: 17
Light Chain
DIVMTQSHKFMSTSVGDRVSIICKASQDVGTAVDWYQQKPGQSPKLLIYWA
STRHTGVPDRFTGSGSGTDFTLTITNVQSEDLADYFCQQYNSYPLTFGAGT
KVEIKRTVAAPSVFIFPPSDEQLKSGTASVVCLLNNFYPREAKVQWKVDNA
LQSGNSQESVTEQDSKDSTYSLSSTLTLSKADYEKHK Example 3

Recombinant Expression of Anti-PSMA Antibodies—Lead humanized anti-PSMA antibodies were selected and recombinantly expressed in CHO cells by both transient transfection, (described in Example 1), and stable bulk pool method to examine expression of the humanized sequence. In transient transfection and stable bulk pool approaches proprietary technology was built into the expression vector and CHO host cells, respectively (see for example WO2018/223108). The non-natural amino acid para acetyl phenylalanine (pAF) was incorporated at position A114, (Kabat numbering scheme, (see Kabat et al., NIH Publication No. 369-847, 1993); position indicated in Table 4 by A), in the PSMA antibody, which is the first amino acid residue of the constant region of the heavy chain.

Example 4

Production of Antibody Drug Conjugates (ADCs)—Antibodies can be purified using chromatography based methods, well known to one of ordinary skill in the art, that involve Protein A affinity capture and cation exchange polishing. The antibody harvested in the cell culture media is captured on a Protein A affinity column and eluted under acidic conditions. Antibody preparation is titrated to pH 5 and polished by running through a cation exchange column. Using post cation exchange the antibody can be buffer exchanged into conjugation buffer.

In the present invention, humanized anti-PSMA antibody was conjugated to a toxin, (MMAE or MMAF), via a small hydrophilic linker. The drug-payload linker covalently conjugates with the pAF in the anti-PSMA heavy chain resulting in the formation of anti-PSMA-ADC(s). PSMA antibody is conjugated with the drug-payload linker by incubating at 28° C. in presence of 135 mM acetic hydrazide, acting as a catalyst. Uncoupled antibodies, uncoupled drug payload-linker, aggregates and impurities were removed by running the reaction mixture through a cation exchange chromatography column before exchanging the anti-PSMA ADC into formulation buffer (50 mM Histidine, 150 mM sodium chloride, 2.5% Trehalose pH 6). The antibody drug conjugate was eluted from the column under a salt gradient generating a monodisperse peak.

Analytic characterization of the monodisperse peak from cation exchange chromatography show the major species to be anti-PSMA ADC with drug-to-antibody ratio (DAR) ranging between 1.8 and 2, was observed within 8 hours. Quality control assessments performed on antibodies and ADCs of the invention show that all preparations generated by this strategy resulted in superior quality materials containing <3% aggregate and <5 EU/mg endotoxin level.

Fifteen (15) anti-PSMA ADCs were generated with two lead humanized variants and chimeric antibodies utilizing the 5 payload-linkers—non-cleavable MMAE, non-cleavable MMAF, cleavable MMAF, short cleavable MMAF, and short cleavable MMAE, disclosed herein. Anti-PSMA ADCs generated with humanized variants 1 and 2, disclosed in Table 4, were selected for further studies in the following Examples.

Example 5

In Vitro Potency Studies—In vitro potency of anti-PSMA ADCs is determined using a metastatic castration-resistant prostate cancer (mCRPC) representative cell-line, C4-2. The cell culture is incubated with antibody drug conjugates for 96 hours at 37° C. Cell viability is analyzed using Cell Titer Glo® (Promega, USA). Anti-proliferative activity is represented by potency, $IC_{50}$, the concentration at which 50% of the maximum activity is achieved and cell killing, and $E_{max}$, the maximum level of growth inhibition. Table 5 summarizes the cell killing and in vitro potency of the anti-PSMA ADCs.

TABLE 5

In Vitro Cell Killing Activity in C4-2 Cell Lines

| Payload | Linker | Humanized Anti-PSMA Antibody Variant 1 | | Humanized Anti-PSMA Antibody Variant 2 | | Chimeric Anti-PSMA Antibody | |
|---|---|---|---|---|---|---|---|
| | | $IC_{50}$ (nM) | Cell Killing (%) | $IC_{50}$ (nM) | Cell Killing (%) | $IC_{50}$ (nM) | Cell Killing (%) |
| MMAE | Non-Cleavable (PEG$_3$) | 11.3 | 64.5 | 12.5 | 67 | 10.2 | 62.5 |
| MMAF | Non-Cleavable (PEG$_3$) | 0.543 | 80.5 | 0.503 | 81 | 0.295 | 89.5 |
| MMAF | Cleavable (Val-Citruline-PEG$_1$) | 0.066 | 91 | 0.051 | 91 | 0.047 | 89.5 |
| MMAF | Short Cleavable (Valine-Citruline-Acetyl) | 0.064 | 92 | 0.053 | 91 | 0.049 | 94.5 |
| MMAE | Short Cleavable (Valine-Citruline-Acetyl) | 0.542 | 81.5 | 0.52 | 81.5 | 0.425 | 82.5 |

Cell killing activity assay suggests payload-linker combination is critical for developing potent antibody drug conjugates. Potent antibody drug conjugates exhibited subnanomolar potency with >75% cell killing. Antibody drug conjugates with MMAF payloads revealed higher cell killing and potency than antibody drug conjugates with MMAE payloads. The in vitro cell killing study suggests that anti-PSMA ADCs with MMAF payload exhibited an order of magnitude higher potency than anti-PSMA ADCs with MMAE payloads.

This study also demonstrate that the activity of the antibody drug conjugate also influenced by the type of linker. Antibody drug conjugates with cleavable linkers exhibited higher cell killing and potency compared to antibody drug conjugates with non-cleavable linker for the same type of payload. As depicted in Table 5, in vitro cell killing study show that anti-PSMA ADCs with either MMAE or MMAF payload exhibited an order of magnitude higher potency for cleavable linkers than non-cleavable linkers. This suggests that potent anti-PSMA ADCs can be generated by appropriate combination of cytotoxic payloads with linkers. Combination of MMAE payload with non-cleavable linker revealed poor potency and killing. Moreover, killing of target cells by the anti-PSMA antibody ADCs is accomplished by targeted delivery of cytotoxic agents by the anti-PSMA antibody. The targeted delivery of cytotoxic agents is facilitated by binding of the anti-PSMA antibody component of the antibody drug conjugate to the receptor or antigen, PSMA, expressed on the cell surface, which is internalized into the cell by the receptor. Studies with prostate cancer cell lines not expressing PSMA, such as PC-3, suggest that potent anti-PSMA ADCs do not exert any cell killing activity. PC-3 cell lines incubated with potent anti-PSMA ADCs for 96 hours were not killed. This suggests that the invented anti-PSMA ADCs are target specific. No bystander killing effect of the antibody drug conjugates was noted. Lack of bystander killing effect of the invented antibody drug conjugates is critical for eliminating non-specific off-target toxicities due to the toxin component, which is often observed in antibody drug conjugates containing MMAE as the cytotoxic payloads. Moreover, target specific activity of the invented anti-PSMA ADCs make these ADCs valuable for treating metastatic prostate cancer. The observation from these studies suggest that any cancerous lesion beyond the primary cancerous prostate tissue expressing PSMA can be treated with the invented anti-PSMA ADCs.

Moreover, cell killing activity of the anti-PSMA ADCs is dependent on the number of receptors expressed on the cell surface. Prostate cancer cell lines with receptor copy numbers >60000 can be killed efficiently by anti-PSMA ADCs of the invention. For example, in vitro cell killing study performed with anti-PSMA ADCs containing MMAF payload with non-cleavable linker showed killing of cell lines with receptor copy number >60000, Table 6, by immunohistochemistry (IHC) and Quantitative indirect immunofluorescence (QiFi) analysis.

TABLE 6

PSMA Expression and In Vitro Cytotoxicity Activity of anti-PSMA-ADC In Human Prostate Cancer Cell Lines

| PCa Cell Line | Tumor Type | PSMA Cell Surface Number (QiFi) | $IC_{50}$ (nM) | Emax (%) | PSMA IHC Score |
|---|---|---|---|---|---|
| C4-2 | Prostate | 84378 (±24440) | 1.498 | 86 | 3‡ |
| MDA-PCa-2B | Prostate | 67771 (±7636) | 0.436 | 62 | 3†† |
| VCap | Prostate | 13470 (±4278) | No activity | | 1†† |

TABLE 6-continued

PSMA Expression and In Vitro Cytotoxicity Activity of anti-PSMA-ADC In Human Prostate Cancer Cell Lines

| PCa Cell Line | Tumor Type | PSMA Cell Surface Number (QiFi) | $IC_{50}$ (nM) | Emax (%) | PSMA IHC Score |
|---|---|---|---|---|---|
| 22Rv1 | Prostate | 8572 (±2123) | No activity | | 1‡ |
| PC-3 | Prostate | 890 (±727) | No activity | | Negative |

‡Determined from in vivo tumor xenograft blocks;
†Not determined due to poor growth
††Determined from cell pellets The dependency of cell killing activity of the invented anti-PSMA ADCs on receptor copy number of PSMA is indicative of therapeutic benefit for treating prostate cancer. Receptor copy number of PSMA is usually high in cancerous prostate tissue compared to expression of PSMA in tissues with no cancer. This differential expression in PSMA receptor copy number between cancerous prostate tissue and normal tissues can facilitate reducing and/or eliminating target-related non-prostate tissue related toxicity. This analysis suggests that the anti-PSMA ADCs can exhibit low activity in tissues expressing low PSMA receptor copy numbers than in cancerous prostate tissue with high PSMA receptor copy number. Hence, the background toxicity of the antibody drug conjugate can be significantly lowered.

Example 6

Figure 2:
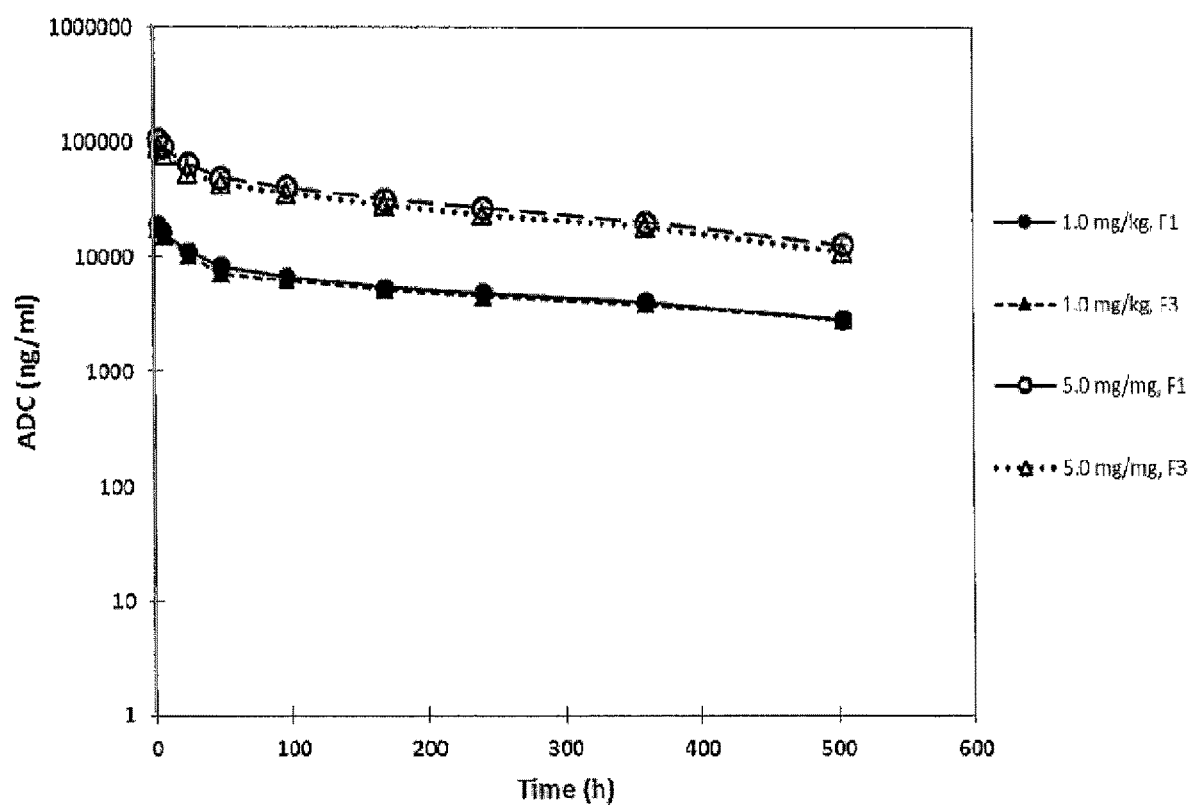
FIG. 2 depicts the pharmacokinetic studies conducted in rat with anti-PSMA ADC showing non-cleavable MMAF at various concentrations.

Pharmacokinetic (PK) Profile with Drug Payload-Linker-Systemic stability of the anti-PSMA ADCs herein, can be assessed by performing pharmacokinetic studies in both mice and rats where the antibody drug conjugates are administered as an intravenous (i.v) bolus. Pharmacokinetic evaluation suggests that the stability of the intact antibody drug conjugate depends on the stability of the linker. Studies performed in mice at single dose of 1 mg/kg suggests that anti-PSMA ADCs with MMAF payload linked by either non-cleavable or short cleavable (Val-Citruline-Acetyl) linker remains intact throughout the duration of the study. The half-life of the intact anti-PSMA ADCs with MMAF payload linked by either non-cleavable or short-cleavable is 10 days, FIG. 1, (top 2 panels). The systemic stability of the short cleavable linker is independent of the payload. The linker in the anti-PSMA ADC with MMAE payload linked by short cleavable linker also remains intact throughout the duration of the study with half-life of the intact antibody drug conjugate being as long as 10 days, FIG. 1, (bottom right panel). However, in contrast, the linker in the anti-PSMA ADC with MMAF payload linked by cleavable (Val-Citruline-PEGi) linker is cleaved early lowering the half-life of the intact antibody drug conjugate to approximately 4 days, FIG. 1, (bottom left panel). F1 represents detection of the antibody drug conjugate in the serum by antibody. F3 represents detection of the antibody drug conjugate in the serum by the toxin-payload linker Systemic stability of anti-PSMA ADC with non-cleavable MMAF was also evaluated in rat at doses 1 mg/kg and 5 mg/kg. The study revealed the antibody drug conjugate to be stable, with the linker and the cytotoxic agent remaining intact throughout the duration of the study, FIG. 2.

Figure 3:
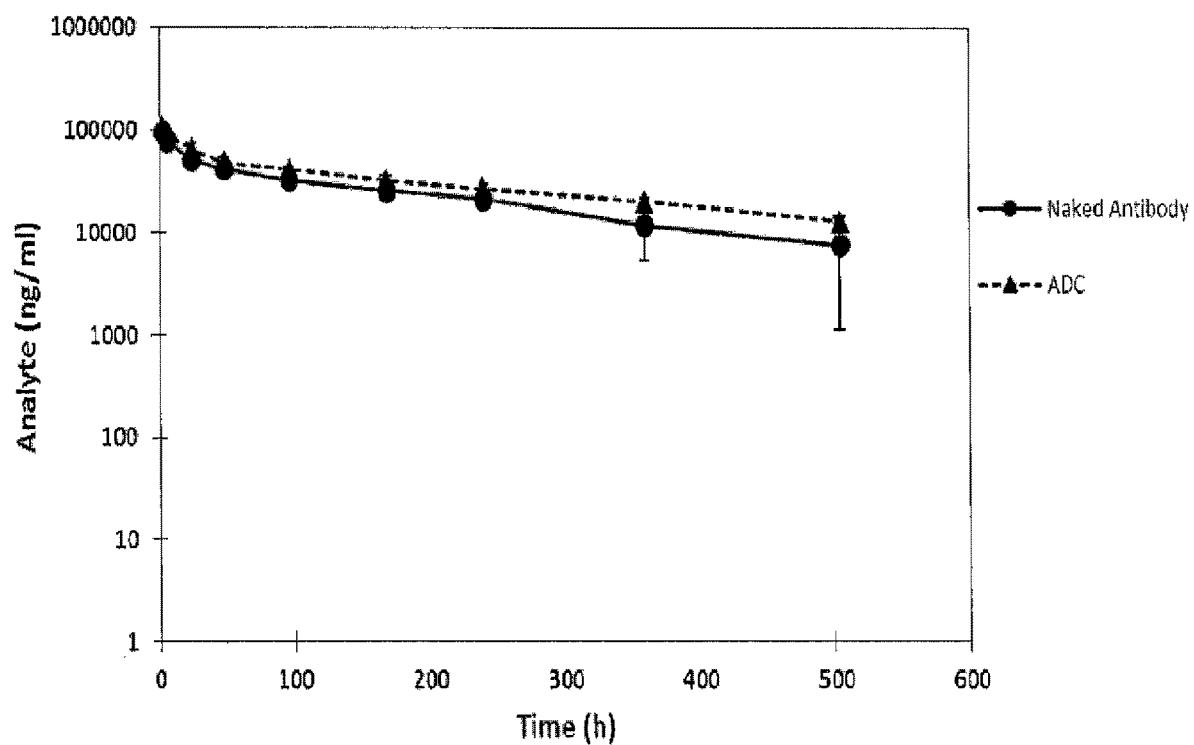
FIG. 3 depicts pharmacokinetic comparison of unconjugated anti-PSMA antibody (naked antibody) compared to ADCs using non-cleavable MMAF.

Studies were performed in rat to compare the pharmacokinetic profile of the anti-PSMA ADCs with non-cleavable MMAF and the anti-PSMA antibody, (denoted as naked antibody), with no cytotoxic agent. Evaluation of the pharmacokinetic profile suggests that the clearance of anti-PSMA ADC with non-cleavable MMAF is similar to anti- PSMA antibody, FIG. 3. This suggests that inherent stability of the antibody is unaffected by p-acetyl phenylalanine based site-specific conjugation and drug loading.

Stability of antibody drug conjugate is essential in lowering toxicity due to the cytotoxic agent. Preventing cleavage of the cytotoxic agent from the antibody drug conjugate while in systemic circulation is a critical way of lowering toxicity. The disclosed anti-PSMA ADCs with non-cleavable and short cleavable linkers are significantly stable in systemic circulation with the cytotoxic agent remaining attached to the antibody. This is significant as most antibody drug conjugates are unstable with drug payload falling off from the linker and/or the site of conjugation and thereby resulting in significant non-target related toxicity due to the cytotoxic agent. Therapeutic application of antibody drug conjugate is currently restricted due to such toxicity. Most antibody drug conjugates in clinical trials revealed dose limiting toxicities that could be ascribed to the cytotoxic agent. Because of such toxicities, therapeutic application of antibody drug conjugate has been limited and to date only four antibody drug conjugates have been approved for therapeutic applications. Treatment of prostate cancer with antibody drug conjugates targeting PSMA have proven challenging in the field to date due to severe toxicities and lack of therapeutic index. The pharmacokinetic data suggests that the invented anti-PSMA ADCs can overcome limitations from non-specific toxicity due to the cytotoxic agent by preventing the cleavage of the drug payload from the linker and/or site of conjugation by unique combination of stable conjugation chemistry with stable linker. The stable conjugation chemistry utilized in generating the novel anti-PSMA ADCs of the invention can be attained by formation of a ketoxime bond between an unnatural/non-natural amino acid, for example p-acetyl phenylalanine, incorporated in the antibody at specific locations and the drug-payload linker derivatized with a hydroxylamine group.

Example 7

In Vivo Efficacy Studies—Anti-tumor efficacy of the anti-PSMA ADCs, with non-cleavable and short cleavable MMAF, was tested in tumor xenograft model in mice engrafted with prostate cancer cell line. Metastatic castration resistant prostate cancer (mCRPC) relevant cell line, C4-2, was obtained from ATCC and expanded in vitro following ATCC instructions. C4-2 human carcinoma xenografts were grown in male immune-compromised mice with cells implanted subcutaneously. Mice were weighed and measured for tumor volume using an electronic caliper. Individual tumor volume was calculated as length×width×width/2. Mice with vascularized tumors (determined by appearance) averaging a volume of 500 mm$^3$ were randomized into treatment groups and were dosed intravenously per individual body weight. Anti-PSMA ADCs were administered at 0.1, 1, 5, and 10 mg/kg.

Figure 4A:
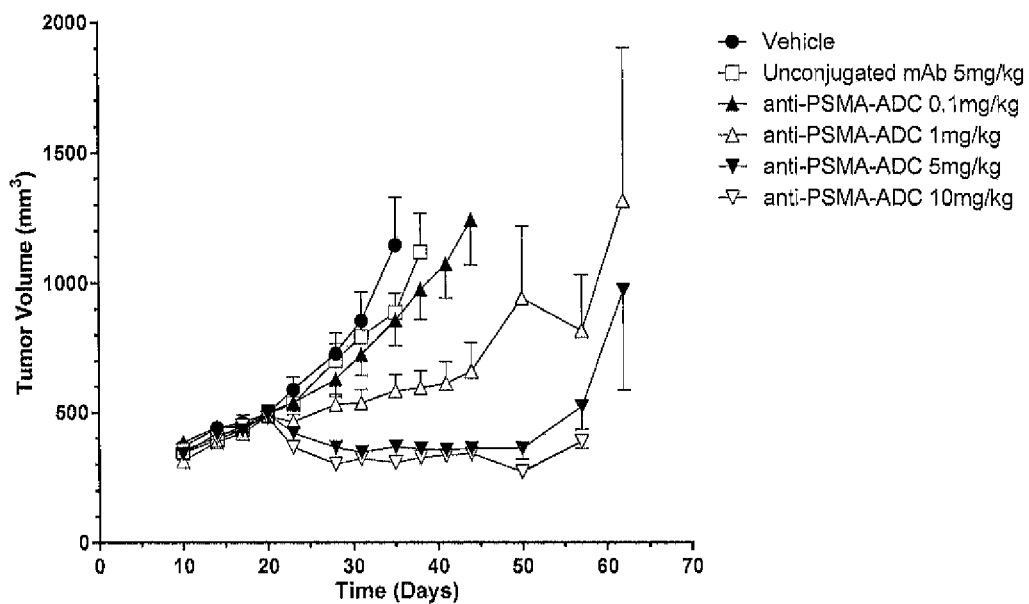
FIGS. 4A-4B depict single dose response in C4-2 xenograft prostate model on tumor growth (FIG. 4A) and body weight change (FIG. 4B) using anti-PSMA ADC non-cleavable MMAF at various dosages.
Figure 4B:
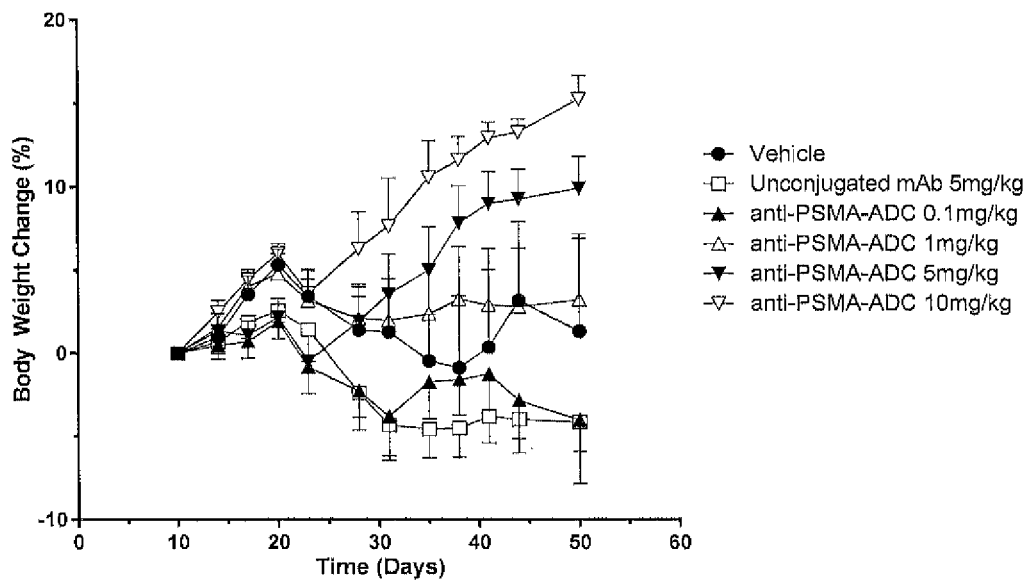
Figure 5A:
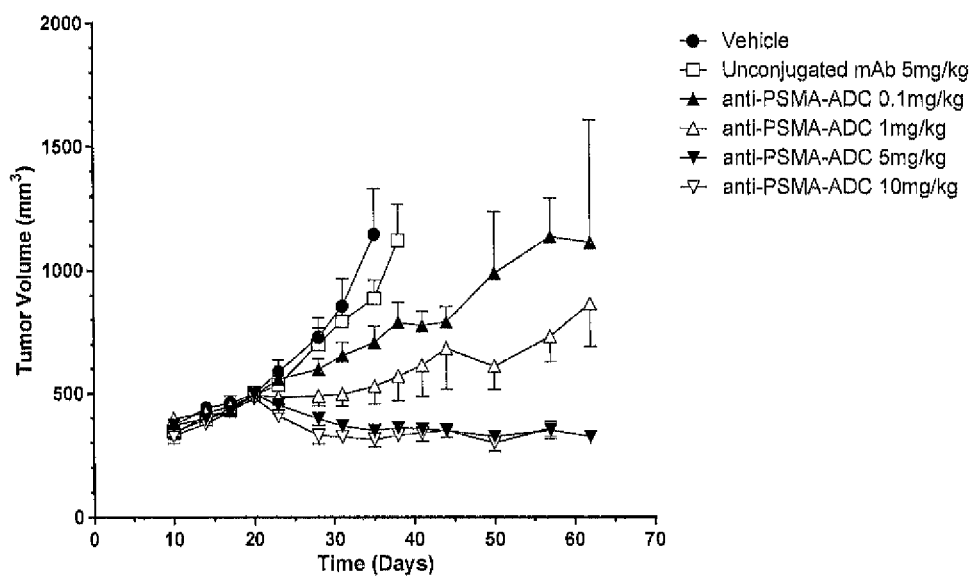
FIGS. 5A-5B depict single dose response in C4-2 xenograft prostate model on tumor growth (FIG. 5A) and body weight change (FIG. 5B) using anti-PSMA ADC short cleavable MMAF at various dosages.
Figure 5B:
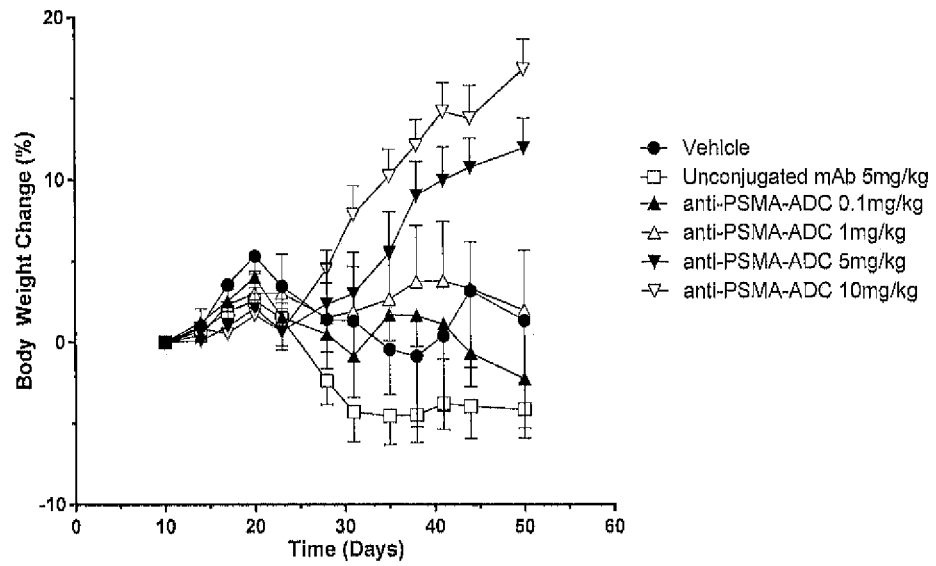

Studies suggest that anti-PSMA ADCs with both non-cleavable and short-cleavable MMAF were effective in preventing tumor growth. At 5 mg/kg and 10 mg/kg anti-PSMA ADCs were effective in inhibiting tumor growth for 37 days post dosing. At 1 mg/kg anti-PSMA ADCs were effective in tumor stasis till regrowth was observed after 35 days post-dosing. At dosage of 0.1 mg/kg, no significant differentiation from the controls was observed. Analysis of body weight show that treated animals also gained weight as normal, healthy mice implying no overt toxicity associated with anti-PSMA ADCs. FIGS. 4A and 4B depict tumor volume and body weight results representative of anti-PSMA ADCs of the invention comprising non-cleavable MMAF. FIGS. 5A and 5B depict tumor volume and body weight results representative of anti-PSMA ADCs of the invention comprising short-cleavable MMAF.

Example 8

Figure 6A:
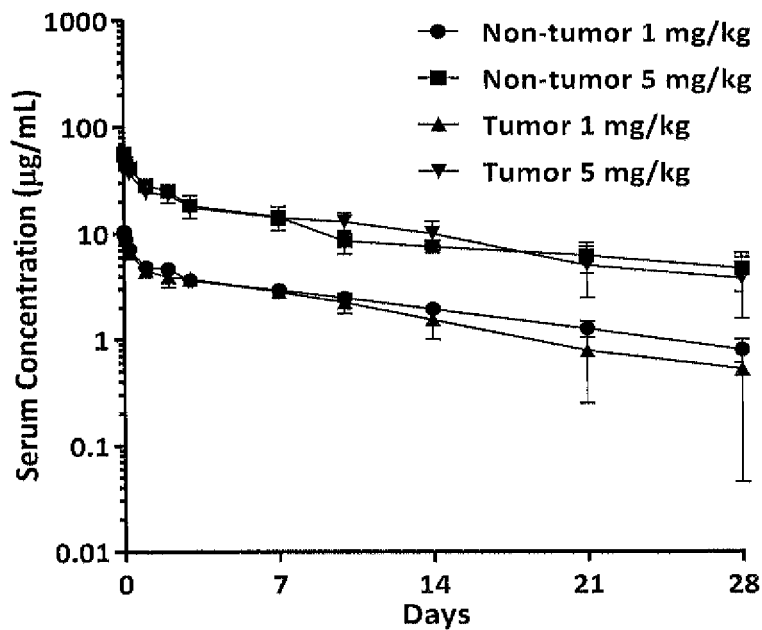
FIGS. 6A-6B depict the pharmacokinetic studies in tumor and non-tumor bearing mice (FIG. 6A) and Cynomolgus monkeys (FIG. 6B) following single dose of anti-PSMA ADC using non-cleavable MMAF.

Pharmacokinetic Studies with Non-Cleavable MMAF-Pharnacokinetics (PK) were assessed in tumor and non-tumor bearing mice following single dose of anti-PSMA ADC using a non-cleavable MMAF. The mice were injected via bolus intravenous injection with 1 mg/kg or 5 mg/kg of the non-cleavable MMAF ADC. Serum was collected and analyzed for the presence of the non-cleavable MMAF ADC. At both dose levels evaluated, 1 mg/kg and 5 mg/kg, similar PK profiles were observed for anti-PSMA ADC concentrations in non-tumor and tumor bearing mice (FIG. 6A).

Figure 6B:
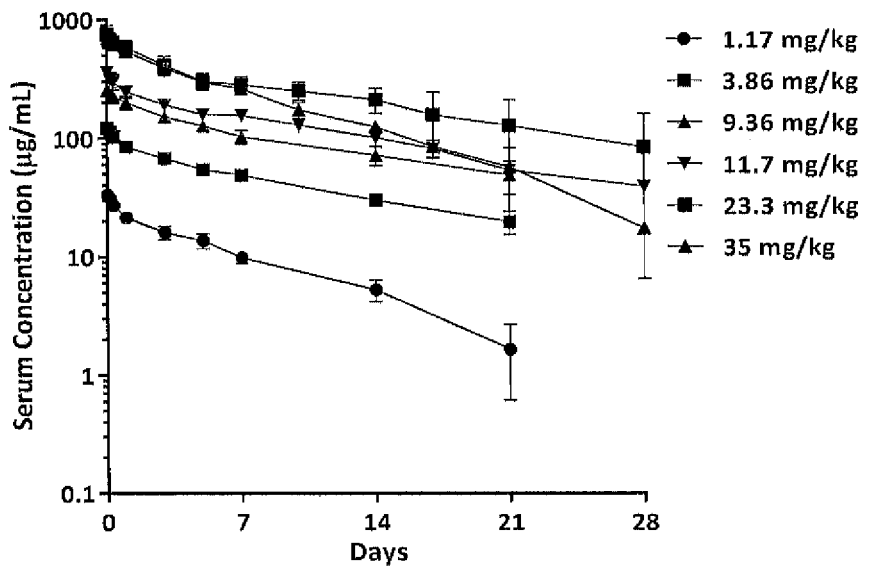

Pharmacokinetics (PK) were also assessed in Cynomolgus monkey following single dose administration of anti-PSMA ADC using a non-cleavable MMAF at various concentrations of 1.17 mg/kg, 3.86 mg/kg, 9.36 mg/kg, 11.7 mg/kg, 23.3 mg/kg and 35.0 mg/kg (FIG. 6B). The anti-PSMA ADCs were administered as an intravenous infusion, (the intended route of administration in the clinic), 15 to 20 minutes. Following dosing, samples were collected through 28 days. Bioanalysis for intact anti-PSMA ADC was performed using a qualified Meso Scale Discovery method. Overlapping PK profiles were observed for intact ADC and total antibody confirming that anti-PSMA ADCs of the present invention are extremely stable in systemic circulation. A non-linear increase in exposure was observed at lower doses, (1.17 mg/kg to 3.86 mg/kg), which could be attributed to the possible target mediated elimination. Further increase in dose resulted in a relatively linear increase in exposures with increase in dose. Clearance was slow, ranging from 0.118 mL/h/kg to 0.304 mL/h/kg, and volume of distribution was small, ranging from 44.2 mL/kg to 58.2 mL/kg. The resulting half-life was long ranging from 129 hours to 346 hours, with a general trend for increase in half-life with increase in dose. It is noted that extreme stability of anti-PSMA ADC in the systemic circulation minimizes off-target toxicity related to the release of free-payload from the ADC, promoting long half-life thereby enabling a patient compliant dosing regimen of once every 3 or 4 weeks.

Example 9

Anti-PSMA ADC Combination Therapy—The anti-PSMA ADCs of the present invention can be used in combination with any agent involved in treating, reducing, ameliorating, or preventing prostate cancer in a subject in need of such, including but not limited to hormone therapy or chemotherapy. For example, the hormone therapy enzalutamide has been demonstrated, in vitro, to increased expression of cell surface PSMA expression approximately 3-fold (Murga et al., Prostate 15; 75(3):242-54, 2015). Additionally, enzalutamide treated mice bearing human PDX prostate tumors showed increased inhibition of tumor growth when combined with a PSMA ADC with the auristatin payload, MMAE (DiPippo et al., Prostate 15; 76(3):325-34, 2016). Based on the increase in PSMA expression noted in the art, the inventors studied the in vivo effect of combination therapy using the invented anti-PSMA ADCs with the MMAF payload and enzalutamide.

Anti-tumor efficacy of the anti-PSMA ADCs of the invention in combination with hormone therapy enzalutamide was tested in tumor xenograft model in mice engrafted with prostate cancer cell line. Metastatic castration resistant prostate cancer (mCRPC) relevant cell line, C4-2, was obtained from ATCC and expanded in vitro following ATCC instructions. C4-2 human carcinoma xenografts were grown in male immune-compromised mice with cells implanted subcutaneously. A second model using male immunocompromised mice bearing patient derived xenograft (PDX) TM00298 (Jackson Laboratories, CA) prostate tumors was also studied.

Mice were weighed and measured for tumor volume using an electronic caliper. Individual tumor volume was calculated as length×width×width/2. Mice with vascularized tumors (determined by appearance) averaging a volume of 500 mm$^3$ were randomized into treatment groups and were dosed intravenously per individual body weight. Anti-PSMA ADCs were administered intravenously at 0.5, 1, and 3 mg/kg weekly for 4 weeks in the C4-2 model and at 1 and 3 mg/kg weekly for 4 weeks in the PDX model. In both prostate models, enzalutamide was administered orally daily at 10 mg/kg, for 28 days. In both prostate models, one group of mice were administered a combination therapy of 1 mg/kg anti-PSMA ADC plus 10 mg/kg enzalutamide, FIGS. 7 and 8. For the PDX model mice were also administered a combination therapy of 3 mg/kg anti-PSMA ADC plus 10 mg/kg enzalutamide, FIG. 8.

Figure 7A:
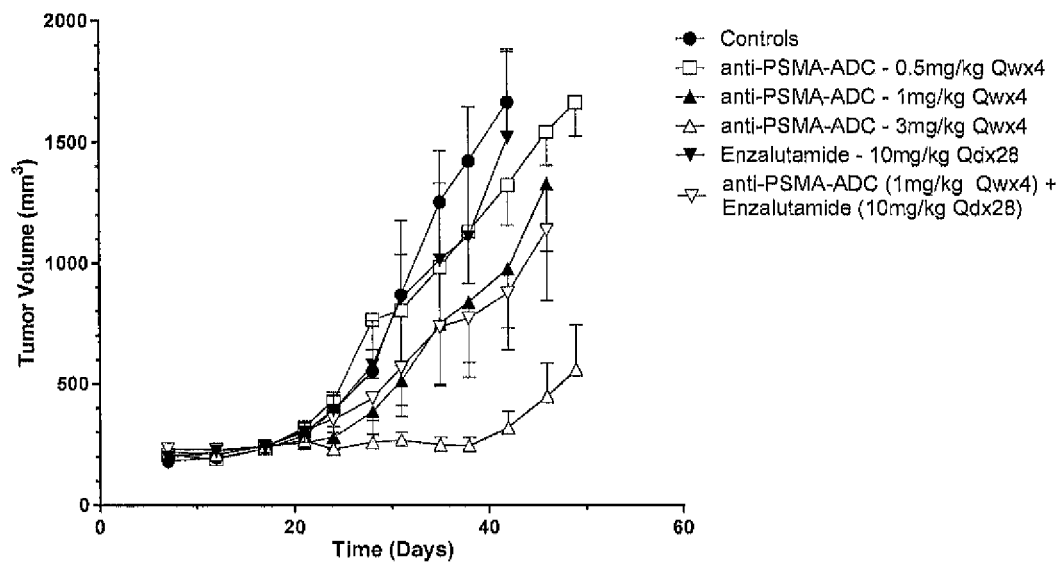
FIGS. 7A-7B depict repeat dose response in C4-2 xenograft prostate model on tumor growth (FIG. 7A) and body weight change (FIG. 7B) using anti-PSMA ADC non-cleavable MMAF and anti-PSMA ADC non-cleavable MMAF plus enzalutamide at various dosages.
Figure 7B:
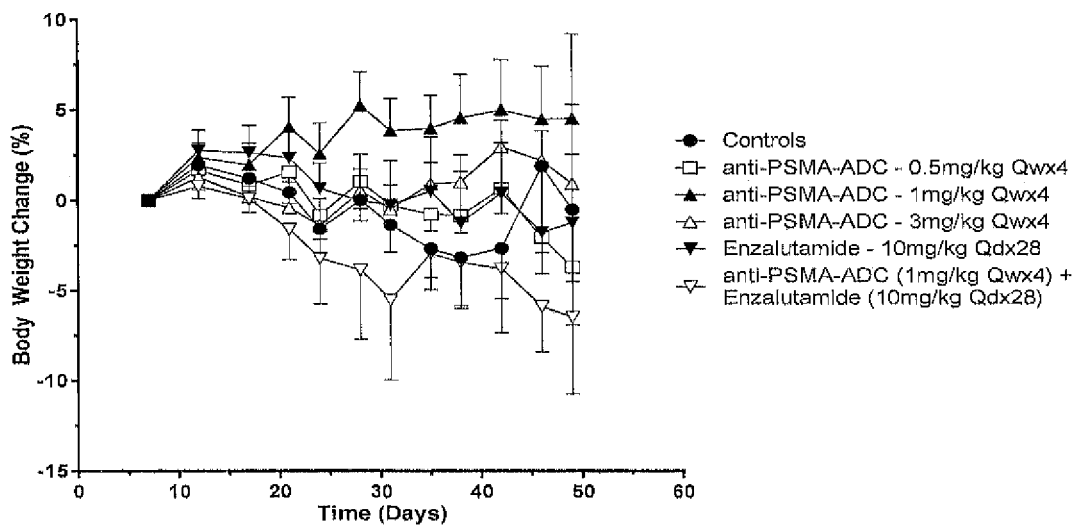
Figure 8A:
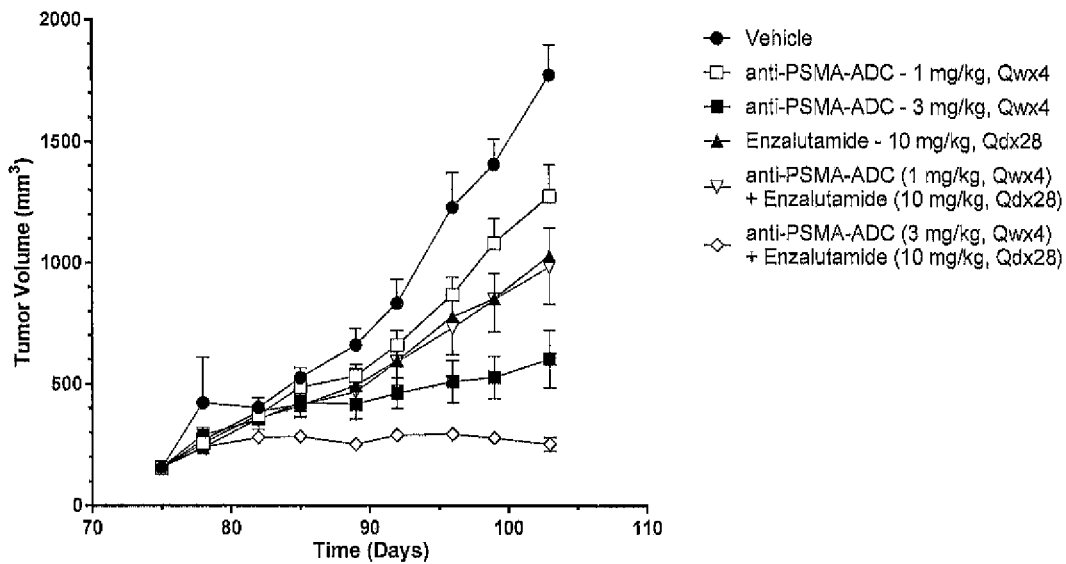
FIGS. 8A-8B depict repeat dose response in PDX prostate model on tumor growth (FIG. 8A) and body weight change (FIG. 8B) using anti-PSMA ADC non-cleavable MMAF and anti-PSMA ADC non-cleavable MMAF plus enzalutamide at various dosages.
Figure 8B:
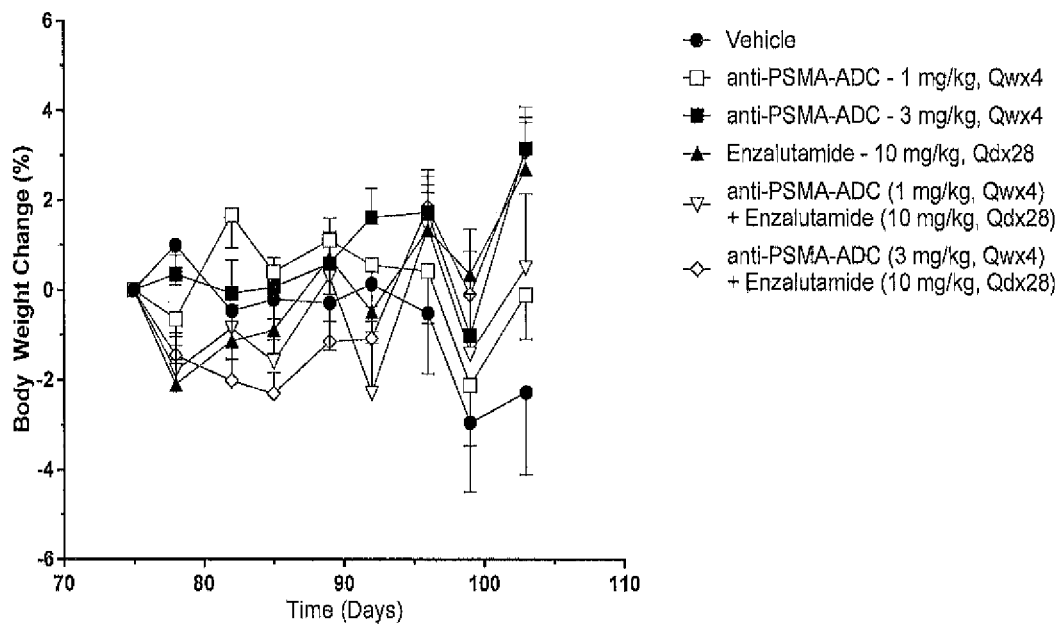

Anti-PSMA ADCs at 3 mg/kg and 1 mg/kg showed tumor inhibition is dose responsive in an enzalutamide resistant model. Complete inhibition was achieved at 3 mg/kg with 80% TGI (percent tumor growth inhibition). Partial response was observed at 1 mg/kg with 37% TGI. Analysis of body weight suggest that treated animals also gained weight as normal, healthy mice implying no overt toxicity associated with anti-PSMA ADCs. FIGS. 7A and 8A depict tumor volume and body weight (FIGS. 7B and 8B) results representative of anti-PSMA ADCs of the invention comprising non-cleavable MMAF.

This study demonstrated improved efficacy with anti-PSMA ADCs of the present invention in combination with enzalutamide. Enzalutamide, as a single agent, increased the level of cell surface PSMA in prostate cancer cells. The combination of anti-PSMA ADCs with enzalutamide showed greater % TGI than monotherapy. These studies suggest that anti-PSMA ADCs with both non-cleavable and short-cleavable MMAF were effective in preventing tumor growth with synergistic effect in the present of enzalutamide.

Example 10

Human Clinical Trial of the Safety and/or Efficacy of anti-PSMA antibody drug conjugate (ADC) for Prostate Cancer Therapy Objective: To compare the safety and phannacokinetics of administered composition comprising anti-PSMA ADC of the present invention.

Study Design: This study will be a Phase I, single- or multi-center, open-label, randomized dose escalation study followed by a Phase II study in prostate cancer patients. Patients should not have had exposure to PSMA derivative prior to the study entry. Patients must not have received treatment for their cancer within 2 weeks of beginning the trial. Treatments include the use of chemotherapy, hematopoietic growth factors, and biologic therapy such as monoclonal antibodies. Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive intravenously anti-PSMA ADC on once every 3 weeks dosing cycles. Doses of anti-PSMA ADC may be held or modified for toxicity based on assessments as outlined below. Treatment repeats every 3 weeks in the absence of unacceptable toxicity. Cohorts of 3-6 patients receive escalating doses of anti-PSMA ADC until the maximum tolerated dose (MTD) for anti-PSMA ADC is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive anti-PSMA ADC as in phase I at the MTD determined in phase I. Treatment repeats every 3 weeks for several cycles in the absence of disease progression or unacceptable toxicity. After completion of course of study therapy, patients who achieve a complete or partial response may receive additional doses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of anti-PSMA ADC. Venous blood samples (5 mL) for determination of serum concentrations are obtained at about 10 minutes prior to dosing and at approximately the following times after dosing: 0.5 and 4 hours, days 1, 2, 4, 7, 14, and 21. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and after study drug administration at 0.5 and 4 hours, days 1, 2, 4, 7, 14, and 21. Pharmacokinetic parameters are calculated by model independent methods using the latest version of Phoenix WinNonlin software. The following pharmacokinetics parameters are determined: peak serum concentration ($C_{max}$); time to peak serum concentration ($t_{max}$); area under the concentration-time curve (AUC) from time zero to the last blood sampling time ($AUC_{last}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle, with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J.

Natl. Cancer Inst. 92(3):205-16, 2000; on the worldwide web at http://ctep.cancer.gov/forms/TherasseRECISTJNCI.pdf). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

What is claimed:

1. An anti-prostate specific membrane antigen (anti-PSMA) antibody comprising a heavy chain sequence selected from the group consisting of SEQ ID NOs: 8, 10, 12 and 14 and a light chain sequence selected from the group consisting of SEQ ID NOs: 9, 11, 13 and 15.

2. The anti-PSMA antibody of claim 1, wherein the light chain sequence is SEQ ID NO: 9.

3. An anti-prostate specific membrane antigen (anti-PSMA) antibody comprising a heavy chain sequence selected from the group consisting of SEQ ID NOs: 8, 10, 12 and 14 and a light chain sequence selected from the group consisting of SEQ ID NOs: 9, 11, 13 and 15, wherein the heavy chain sequence comprises a non-naturally encoded amino acid.

4. The anti-PSMA antibody of claim 3, wherein the non-naturally encoded amino acid is para-acetyl phenylalanine, p-nitrophenylalanine, p-sulfotyrosine, p-carboxyphenyl alanine, o-nitrophenylalanine, m-nitrophenylalanine, p-boronyl phenylalanine, o-boronylphenylalanine, m-boronylphenylalanine, p-aminophenylalanine, o-aminophenylalanine, m-aminophenylalanine, p-acylphenylalanine, o-acylphenylalanine, m-acylphenylalanine, p-OMe phenylalanine, o-OMe phenylalanine, m-OMe phenylalanine, p-sulfophenylalanine, o-sulfophenylalanine, m-sulfophenylalanine, 5-nitro His, 3-nitro Tyr, 2-nitro Tyr, nitro substituted Leu, nitro substituted His, nitro substituted De, nitro substituted Trp, 2-nitro Trp, 4-nitro Trp, 5-nitro Trp, 6-nitro Trp, 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenyl alanine, p-acetyl-L-phenylalanine, a p-propargyl-phenylalanine, O-methyl-L-tyrosine, L-3-(2-naphthyl)alanine, 3-methylphenylalanine, O-4-allyl-L-tyrosine, 4-propyl-L-tyrosine, tri-O-acetyl-GlcNAcβ-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine or p-propargyloxy-phenylalanine.

5. The anti-PSMA antibody of claim 4, wherein the non-naturally encoded amino acid is p-acetyl-L-phenylalanine.

6. The anti-PSMA antibody of claim 3, wherein the non-naturally encoded amino acid is incorporated at position 114 according to Kabat numbering of the heavy chain sequence.

7. A method of treating a subject having a PSMA-expressing cancer cell or cancer comprising: administering to the subject an effective amount of an antibody drug conjugate to treat the PSMA-expressing cancer cell or cancer, wherein the antibody drug conjugate comprises the anti-PSMA antibody of claim 3 conjugated to a drug-linker via the non-naturally encoded amino acid; wherein the drug-linker has the following structure:

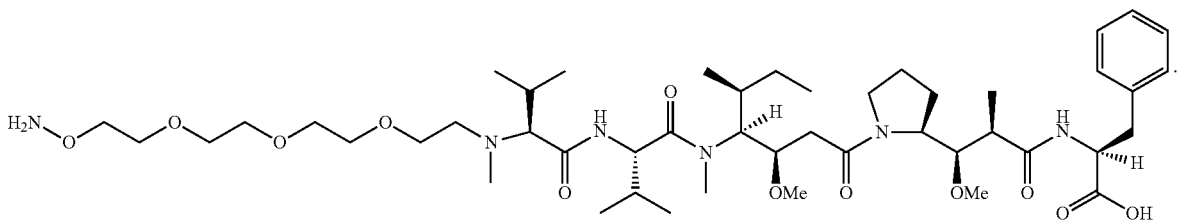 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCOCCOCCON)C(C)C]

8. The method of claim 7, further comprising providing to the subject a therapeutic agent.

9. The method of claim 8, wherein the therapeutic agent is a chemotherapeutic agent, hormonal agent, antitumor agent, immunostimulatory agent, immunomodulator, corticosteroid or combination thereof.

10. The method of claim 9, wherein the therapeutic agent is a hormonal agent, and wherein the hormonal agent is enzalutamide.

11. An antibody drug conjugate comprising a humanized anti-prostate specific membrane antigen (anti-PSMA) antibody conjugated to at least one drug-linker, wherein the at least one drug-linker comprises a cytotoxic agent;
wherein the anti-PSMA antibody comprises a heavy chain sequence selected from the group consisting of SEQ ID NOs: 8, 10, 12 and 14 and a light chain sequence selected from the group consisting of SEQ ID NOs: 9, 11, 13 and 15; and the conjugation occurs via a non-naturally encoded amino acid incorporated in the heavy chain sequence.

12. The antibody drug conjugate of claim 11, wherein the cytotoxic agent is a dolastatin, dolastatin derivative or analog thereof.

13. The antibody drug conjugate of claim 6, wherein the dolastatin, dolastatin derivative or analog thereof is monomethyl auristatin F or monomethyl auristatin E.

14. The antibody drug conjugate of claim 11, wherein the at least one drug-linker has the following structure:

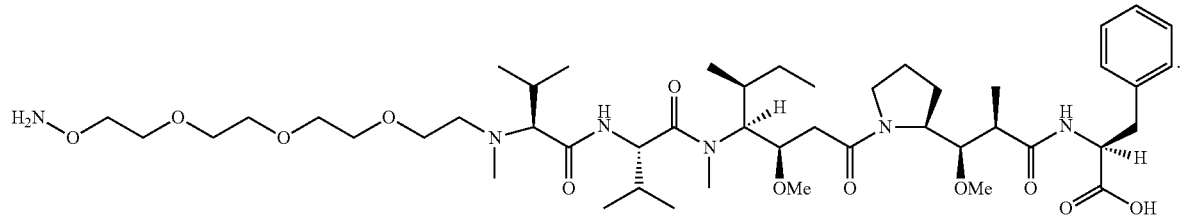 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCOCCOCCON)C(C)C]

15. A method of reducing or inhibiting tumor growth or progression in a PSMA-expressing cancer or cancer cell comprising contacting the PSMA-expressing cancer or cancer cell with an effective amount of the antibody drug conjugate of claim 11.

16. The method of claim 15, further comprising contacting the PSMA-expressing cancer or cancer cell with an effective amount of a therapeutic agent.

17. The method of claim 16, wherein the therapeutic agent is a chemotherapeutic agent, hormonal agent, antitumor agent, immunostimulatory agent, immunomodulator, corticosteroid or combination thereof.

18. The method of claim 17, wherein the hormonal agent is enzalutamide.

19. A pharmaceutical composition comprising the antibody drug conjugate of claim 11 and at least one pharmaceutically acceptable adjuvant, binder, buffer, carrier, diluent or excipient.

20. The pharmaceutical composition of claim 19 further comprising a chemotherapeutic agent, hormonal agent, antitumor agent, immunostimulatory agent, immunomodulator, corticosteroid or combination thereof.

21. The pharmaceutical composition of claim 20, wherein the pharmaceutical composition further comprises the hormonal agent, and wherein the hormonal agent is enzalutamide.

22. An antibody drug conjugate comprising an anti-prostate specific membrane antigen antibody (anti-PSMA antibody) conjugated to a drug-linker, wherein the conjugation occurs via a para-acetyl phenylalanine incorporated in the heavy chain sequence of the antibody, wherein the anti-PSMA antibody comprises the heavy chain sequence of SEQ ID NO: 8 and the light chain sequence of SEQ ID NO: 9,in which the para-acetyl phenylalanine is incorporated at heavy chain position A114 according to Kabat numbering, and wherein the drug-linker has the following structure:

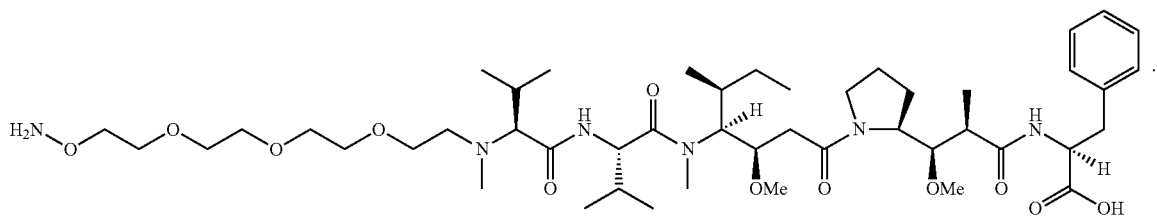 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCOCCOCCOCCON)C(C)C ; "."]

* * * * *

SEQUENCE LISTING

```
<160> NUMBER OF SEQ ID NOS: 17

<210> SEQ ID NO 1
<211> LENGTH: 115
<212> TYPE: PRT
<213> ORGANISM: Artificial Sequence
<220> FEATURE:
<223> OTHER INFORMATION: Humanized Heavy Chain Variable Region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Gln Arg Leu Glu Trp Met
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser
        115

<210> SEQ ID NO 2
<211> LENGTH: 110
<212> TYPE: PRT
<213> ORGANISM: Artificial Sequence
<220> FEATURE:
<223> OTHER INFORMATION: Humanized Light Chain Variable Region

<400> SEQUENCE: 2

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val
            100                 105                 110

<210> SEQ ID NO 3
<211> LENGTH: 110
<212> TYPE: PRT
<213> ORGANISM: Artificial Sequence
<220> FEATURE:
```

<223> OTHER INFORMATION: Humanized Light Chain Variable Region

<400> SEQUENCE: 3

| Asp | Ile | Gln | Leu | Thr | Gln | Ser | Pro | Ser | Phe | Leu | Ser | Ala | Ser | Val | Gly |
|---|---|---|---|---|---|---|---|---|---|---|---|---|---|---|---|
| 1 | | | | 5 | | | | | 10 | | | | | 15 | |

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val
                100                 105                 110

<210> SEQ ID NO 4
<211> LENGTH: 110
<212> TYPE: PRT
<213> ORGANISM: Artificial Sequence
<220> FEATURE:
<223> OTHER INFORMATION: Humanized Light Chain Variable Region

<400> SEQUENCE: 4

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val
                100                 105                 110

<210> SEQ ID NO 5
<211> LENGTH: 110
<212> TYPE: PRT
<213> ORGANISM: Artificial Sequence
<220> FEATURE:
<223> OTHER INFORMATION: Humanized Light Chain Variable Region

<400> SEQUENCE: 5

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Asn Leu Gln Pro 65                  70                  75                  80
Glu Asp Phe Ala Thr Tyr Tyr Cys Gln Gln Tyr Asn Ser Tyr Pro Leu
                         85                  90                  95

Thr Phe Gly Gly Gly Thr Lys Val Glu Ile Lys Arg Thr Val
                100                 105                 110

<210> SEQ ID NO 6
<211> LENGTH: 115
<212> TYPE: PRT
<213> ORGANISM: Artificial Sequence
<220> FEATURE:
<223> OTHER INFORMATION: Chimeric Heavy Chain Variable Region

<400> SEQUENCE: 6

Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
            35                  40                  45

Gly Asn Ile Asn Pro Asn Asn Gly Gly Thr Thr Tyr Asn Gln Lys Phe
        50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
                100                 105                 110

Val Ser Ser
        115

<210> SEQ ID NO 7
<211> LENGTH: 110
<212> TYPE: PRT
<213> ORGANISM: Artificial Sequence
<220> FEATURE:
<223> OTHER INFORMATION: Chimeric Light Chain Variable Region

<400> SEQUENCE: 7

Asp Ile Val Met Thr Gln Ser His Lys Phe Met Ser Thr Ser Val Gly
1               5                   10                  15

Asp Arg Val Ser Ile Ile Cys Lys Ala Ser Gln Asp Val Gly Thr Ala
                20                  25                  30

Val Asp Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Gln Gln Tyr Asn Ser Tyr Pro Leu
                85                  90                  95

Thr Phe Gly Ala Gly Thr Lys Val Glu Ile Lys Arg Thr Val
                100                 105                 110

<210> SEQ ID NO 8
<211> LENGTH: 444
<212> TYPE: PRT
<213> ORGANISM: Artificial Sequence
<220> FEATURE:

<223> OTHER INFORMATION: Humanized Anti-PSMA Variant - Heavy Chain

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Gln Arg Leu Glu Trp Met
        35                  40                  45

Gly Asn Ile Asn Pro Asn Asn Gly Gly Thr Thr Tyr Asn Gln Lys Phe
    50                  55                  60

Glu Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

-continued

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 9
<211> LENGTH: 214
<212> TYPE: PRT
<213> ORGANISM: Artificial Sequence
<220> FEATURE:
<223> OTHER INFORMATION: Humanized Anti-PSMA Variant - Light Chain

<400> SEQUENCE: 9

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 444
<212> TYPE: PRT
<213> ORGANISM: Artificial Sequence
<220> FEATURE:
<223> OTHER INFORMATION: Humanized Anti-PSMA Variant - Heavy Chain

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Gln Arg Leu Glu Trp Met
        35                  40                  45
```

```
Gly Asn Ile Asn Pro Asn Asn Gly Gly Thr Thr Tyr Asn Gln Lys Phe
     50                  55                  60

Glu Asp Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Leu Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 11
<211> LENGTH: 214
```

```
<212> TYPE: PRT
<213> ORGANISM: Artificial Sequence
<220> FEATURE:
<223> OTHER INFORMATION: Humanized Anti-PSMA Variant - Light Chain

<400> SEQUENCE: 11

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 444
<212> TYPE: PRT
<213> ORGANISM: Artificial Sequence
<220> FEATURE:
<223> OTHER INFORMATION: Humanized Anti-PSMA Variant - Heavy Chain

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Ile His Trp Val Arg Gln Ala Pro Gly Gln Arg Leu Glu Trp Met
        35                  40                  45

Gly Asn Ile Asn Pro Asn Asn Gly Gly Thr Thr Tyr Asn Gln Lys Phe
50                  55                  60

Glu Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Thr Leu Thr
            100                 105                 110
```

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 13
<211> LENGTH: 214
<212> TYPE: PRT
<213> ORGANISM: Artificial Sequence
<220> FEATURE:
<223> OTHER INFORMATION: Humanized Anti-PSMA Variant - Light Chain

<400> SEQUENCE: 13

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

```
Val Asp Trp Tyr Gln Gln Lys Pro Gly Lys Ala Pro Lys Leu Leu Ile
         35                  40                  45

Tyr Trp Ala Ser Thr Arg His Thr Gly Val Pro Asp Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
         130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
         210
```

```
<210> SEQ ID NO 14
<211> LENGTH: 444
<212> TYPE: PRT
<213> ORGANISM: Artificial Sequence
<220> FEATURE:
<223> OTHER INFORMATION: Humanized Anti-PSMA Variant - Heavy Chain

<400> SEQUENCE: 14

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Glu Tyr
             20                  25                  30

Thr Ile His Trp Val Arg Gln Ala Pro Gly Gln Arg Leu Glu Trp Met
         35                  40                  45

Gly Asn Ile Asn Pro Asn Asn Gly Gly Thr Thr Tyr Asn Gln Lys Phe
     50                  55                  60

Glu Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                 85                  90                  95

Ala Ala Gly Trp Asn Phe Asp Tyr Trp Gly Gln Gly Thr Thr Leu Thr
             100                 105                 110

Val Ser Ser Ala Ser Thr Lys Gly Pro Ser Val Phe Pro Leu Ala Pro
         115                 120                 125

Ser Ser Lys Ser Thr Ser Gly Gly Thr Ala Ala Leu Gly Cys Leu Val
         130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
             165                 170                 175
```

```
Leu Tyr Ser Leu Ser Ser Val Thr Val Pro Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 15
<211> LENGTH: 214
<212> TYPE: PRT
<213> ORGANISM: Artificial Sequence
<220> FEATURE:
<223> OTHER INFORMATION: Humanized Anti-PSMA Variant - Light Chain

<400> SEQUENCE: 15

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asp Val Gly Thr Ala
            20                  25                  30

Val Asp Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Tyr Asn Ser Tyr Pro Leu
                85                  90                  95
```

-continued

```
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 16
<211> LENGTH: 444
<212> TYPE: PRT
<213> ORGANISM: Artificial Sequence
<220> FEATURE:
<223> OTHER INFORMATION: Chimeric Anti-PSMA Antibody Variant - Heavy
      Chain

<400> SEQUENCE: 16

Glu Val Gln Leu Gln Gln Ser Gly Pro Glu Leu Val Lys Pro Gly Thr
1               5                   10                  15
Ser Val Arg Ile Ser Cys Lys Thr Ser Gly Tyr Thr Phe Thr Glu Tyr
                20                  25                  30
Thr Ile His Trp Val Lys Gln Ser His Gly Lys Ser Leu Glu Trp Ile
            35                  40                  45
Gly Asn Ile Asn Pro Asn Asn Gly Gly Thr Thr Tyr Asn Gln Lys Phe
        50                  55                  60
Glu Asp Lys Ala Thr Leu Thr Val Asp Lys Ser Ser Ser Thr Ala Tyr
65                  70                  75                  80
Met Glu Leu Arg Ser Leu Thr Ser Glu Asp Ser Ala Val Tyr Tyr Cys
                85                  90                  95
Ala Ala Gly Trp Asn Phe Asp Tyr Trp Gly Gln Gly Thr Thr Leu Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
```

```
                225                 230                 235                 240
        Phe Pro Pro Lys Pro Lys Asp Thr Leu Met Ile Ser Arg Thr Pro Glu
                        245                 250                 255

Val Thr Cys Val Val Val Asp Val Ser His Glu Asp Pro Glu Val Lys
                        260                 265                 270

Phe Asn Trp Tyr Val Asp Gly Val Glu Val His Asn Ala Lys Thr Lys
                        275                 280                 285

Pro Arg Glu Glu Gln Tyr Asn Ser Thr Tyr Arg Val Val Ser Val Leu
                        290                 295                 300

Thr Val Leu His Gln Asp Trp Leu Asn Gly Lys Glu Tyr Lys Cys Lys
        305                 310                 315                 320

Val Ser Asn Lys Ala Leu Pro Ala Pro Ile Glu Lys Thr Ile Ser Lys
                        325                 330                 335

Ala Lys Gly Gln Pro Arg Glu Pro Gln Val Tyr Thr Leu Pro Pro Ser
                        340                 345                 350

Arg Asp Glu Leu Thr Lys Asn Gln Val Ser Leu Thr Cys Leu Val Lys
                        355                 360                 365

Gly Phe Tyr Pro Ser Asp Ile Ala Val Glu Trp Glu Ser Asn Gly Gln
                        370                 375                 380

Pro Glu Asn Asn Tyr Lys Thr Thr Pro Pro Val Leu Asp Ser Asp Gly
        385                 390                 395                 400

Ser Phe Phe Leu Tyr Ser Lys Leu Thr Val Asp Lys Ser Arg Trp Gln
                        405                 410                 415

Gln Gly Asn Val Phe Ser Cys Ser Val Met His Glu Ala Leu His Asn
                        420                 425                 430

His Tyr Thr Gln Lys Ser Leu Ser Leu Ser Pro Gly
                        435                 440

<210> SEQ ID NO 17
<211> LENGTH: 190
<212> TYPE: PRT
<213> ORGANISM: Artificial Sequence
<220> FEATURE:
<223> OTHER INFORMATION: Chimeric Anti-PSMA Antibody Variant - Light
      Chain

<400> SEQUENCE: 17

Asp Ile Val Met Thr Gln Ser His Lys Phe Met Ser Thr Ser Val Gly
        1               5                   10                  15

Asp Arg Val Ser Ile Ile Cys Lys Ala Ser Gln Asp Val Gly Thr Ala
                        20                  25                  30

Val Asp Trp Tyr Gln Gln Lys Pro Gly Gln Ser Pro Lys Leu Leu Ile
                        35                  40                  45

Tyr Trp Ala Ser Thr Arg His Thr Gly Val Pro Asp Arg Phe Thr Gly
                        50                  55                  60

Ser Gly Ser Gly Thr Asp Phe Thr Leu Thr Ile Thr Asn Val Gln Ser
        65                  70                  75                  80

Glu Asp Leu Ala Asp Tyr Phe Cys Gln Gln Tyr Asn Ser Tyr Pro Leu
                        85                  90                  95

Thr Phe Gly Ala Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys
                180                 185                 190
```

UNITED STATES PATENT AND TRADEMARK OFFICE
CERTIFICATE OF CORRECTION

PATENT NO. : 12,059,473 B2  
APPLICATION NO. : 17/042838  
DATED : August 13, 2024  
INVENTOR(S) : Shivarupam Bhowmik Page 1 of 1

It is certified that error appears in the above-identified patent and that said Letters Patent is hereby corrected as shown below:

In the Specification

At Column 134, Line 11,
"DIQLTQSPSELSASVGDRVTTTCKASQDVGTAVDWYQQKPGKAPKLLIYWA" should read
--DIQLTQSPSFLSASVGDRVTITCKASQDVGTAVDWYQQKPGKAPKLLIYWA--.

In the Claims

In Claim 22, the following structure:

" 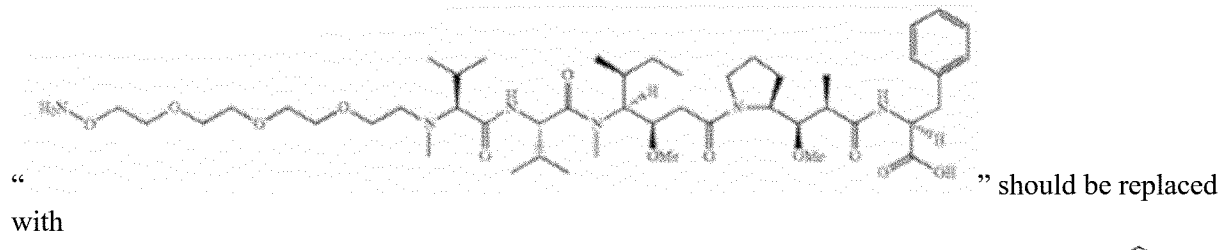 " should be replaced with

-- 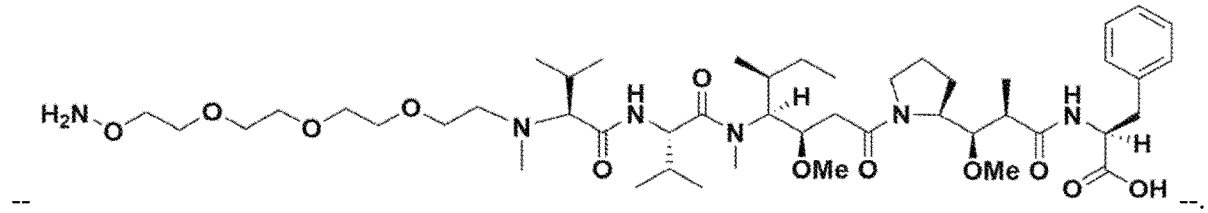 --.

Signed and Sealed this  
Seventh Day of October, 2025

John A. Squires  
*Director of the United States Patent and Trademark Office*